US010231648B2

(12) United States Patent
Plotnik-Peleg et al.

(10) Patent No.: US 10,231,648 B2
(45) Date of Patent: Mar. 19, 2019

(54) FREEZING OF GAIT (FOG), DETECTION, PREDICTION AND/OR TREATMENT

(71) Applicant: The Medical Research, Infrastructure and Health Services Fund of the Tel Aviv Medical Center, Tel-Aviv (IL)

(72) Inventors: Meir Plotnik-Peleg, Kfar-Saba (IL); Jeffrey M. Hausdorff, Hashmonaim (IL); Nir Giladi, Tel-Aviv (IL); Anat Mirelman, Ramat-Gan (IL)

(73) Assignee: The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 0 days.

(21) Appl. No.: 15/607,548

(22) Filed: May 29, 2017

(65) Prior Publication Data
US 2017/0258370 A1    Sep. 14, 2017

Related U.S. Application Data

(63) Continuation of application No. 14/350,569, filed as application No. PCT/IB2012/055454 on Oct. 9, 2012.
(Continued)

(51) Int. Cl.
*A61B 5/00* (2006.01)
*A61B 5/11* (2006.01)
(Continued)

(52) U.S. Cl.
CPC .......... *A61B 5/1104* (2013.01); *A61B 5/0476* (2013.01); *A61B 5/112* (2013.01);
(Continued)

(58) Field of Classification Search
CPC ... A61B 5/1104; A61B 5/1117; A61B 5/1118; A61B 5/112; A61B 5/0476; A61B 5/162;
(Continued)

(56) References Cited

U.S. PATENT DOCUMENTS 6,050,822 A    4/2000 Faughn
8,409,116 B2   4/2013 Wang et al.
(Continued)

FOREIGN PATENT DOCUMENTS

| WO | WO 2010/150260 | 12/2010 |
| WO | WO 2013/054257 | 4/2013 |
| WO | WO 2013/054258 | 4/2013 |

OTHER PUBLICATIONS

Applicant-Initiated Interview Summary dated Sep. 28, 2017 From the US Patent and Trademark Office Re. U.S. Appl. No. 14/350,569. (3 pages).
(Continued)

*Primary Examiner* — Max Hindenburg

(57) ABSTRACT

A method and system for provoking gait disorders, such as freezing of gait; usable, for example, for diagnosing and/or treatment thereof. In an exemplary embodiment of the invention, displays of situations calculated to cause freezing of gait are presented to a subject, optionally using virtual reality displays. Optionally or alternatively, incipit freezing of gait is identified using changes in gait parameters, and optionally used to guide attempts at causing freezing of gait. Optionally or alternatively, a portable device is provided which detects incipit freezing of gait and generates a corrective signal to the subject.

23 Claims, 24 Drawing Sheets

Related U.S. Application Data

(60) Provisional application No. 61/545,164, filed on Oct. 9, 2011, provisional application No. 61/545,161, filed on Oct. 9, 2011.

(51) Int. Cl.
    *A61B 5/0476* (2006.01)
    *A61B 5/16* (2006.01)
    *G06F 19/00* (2018.01)
    A61B 5/0205 (2006.01)
    A61B 5/026 (2006.01)
    A61B 5/0484 (2006.01)

(52) U.S. Cl.
    CPC ............ *A61B 5/1117* (2013.01); *A61B 5/162* (2013.01); *A61B 5/744* (2013.01); *G06F 19/00* (2013.01); *A61B 5/0205* (2013.01); *A61B 5/026* (2013.01); *A61B 5/04842* (2013.01); *A61B 5/1118* (2013.01); *A61B 5/7203* (2013.01); *A61B 5/7257* (2013.01); *A61B 2505/09* (2013.01)

(58) Field of Classification Search
    CPC ....... A61B 5/744; A61B 5/0205; A61B 5/026; A61B 5/7203; A61B 5/7257
    See application file for complete search history.

(56) References Cited

U.S. PATENT DOCUMENTS

| | | | |
|---|---|---|---|
| 8,744,587 | B2 | 6/2014 | Miesel et al. |
| 2006/0247104 | A1 | 11/2006 | Grabiner et al. |
| 2007/0129622 | A1 | 6/2007 | Bourget et al. |
| 2008/0162088 | A1 | 7/2008 | DeVaul et al. |
| 2008/0252445 | A1 | 10/2008 | Kolen |
| 2009/0124938 | A1 | 5/2009 | Brunner |
| 2009/0240170 | A1 | 9/2009 | Rowley et al. |
| 2010/0228144 | A1 | 9/2010 | Labat |
| 2014/0276130 | A1 | 9/2014 | Mirelman et al. |
| 2014/0303508 | A1 | 10/2014 | Plotnik-Peleg et al. |

OTHER PUBLICATIONS

Office Action dated Sep. 18, 2017 From the Israel Patent Office Re. Application No. 231996 and Its Translation Into English. (6 Pages).
Official Action dated Aug. 8, 2017 From the US Patent and Trademark Office Re. U.S. Appl. No. 14/350,567. (15 pages).
Official Action dated Jun. 8, 2017 From the US Patent and Trademark Office Re. U.S. Appl. No. 14/350,569. (7 pages).
Applicant-Initiated Interview Summary dated Nov. 30, 2017 From the US Patent and Trademark Office Re. U.S. Appl. No. 14/350,567. (2 pages).
Applicant-Initiated Interview Summary dated Jul. 5, 2017 From the US Patent and Trademark Office Re. U.S. Appl. No. 14/350,567. (3 pages).
International Preliminary Report on Patentability dated Apr. 24, 2014 From the International Bureau of WIPO Re. Application No. PCT/IB2012/055453.
International Search Report and the Written Opinion dated Feb. 28, 2013 From the International Search Authority Re. Application No. PCT/IB2012/055453.
International Search Report and the Written Opinion dated Feb. 28, 2013 From the International Search Authority Re. Application No. PCT/IB2012/055454.
Official Action dated Sep. 2, 2016 From the US Patent and Trademark Office Re. U.S. Appl. No. 14/350,569.
Official Action dated May 4, 2017 From the US Patent and Trademark Office Re. U.S. Appl. No. 14/350,567. (20 pages).
Official Action dated Oct. 6, 2016 From the US Patent and Trademark Office Re. U.S. Appl. No. 14/350,567.
Official Action dated Apr. 20, 2016 From the US Patent and Trademark Office Re. U.S. Appl. No. 14/350,569.
Restriction Official Action dated Jan. 25, 2016 From the US Patent and Trademark Office Re. U.S. Appl. No. 14/350,569.
Supplementary European Search Report and the European Search Opinion dated May 19, 2015 From the European Patent Office Re. Application No. 12839495.4.
AGS et al. "Guideline for the Prevention of Falls in Older Persons", Journal of the American Geriatrics Society, JAGS, 49(5): 664-672, May 2001.
Bachlin et al. "A Wearable System to Assist Walking of Parkinson's Disease", Methods of Information in Medicine, 49(1): 88-95, 2010.
Bakker et al. "Recent Advances in Functional Neuroimaging of Gait", Journal of Neural Transmission, 114(10): 1323-1331, Oct. 31, 2007.
Brichetto et al. "Evaluation of Physical Therapy in Parkinsonian Patients With Freezing of Gait: A Pilot Study", Clinical Rehabilitation, 20(1): 31-35, Jan. 2006.
Chee et al. "Gait Freezing in Parkinson's Disease and the Stride Length Sequence Effect Interaction", Brain, 132: 2151-2160, 2009.
Delbaere et al. "Development and Validation of Fall Risk Screening Tools for Use in Residential Aged Care Facilities", Medical Journal of Australia, 189(4): 193-196, Aug. 18, 2008.
Fasano et al. "Modulation of Gait Coordination by Subthalamic Stimulation Improves Freezing of Gait", Movement Disorders, 26(5): 844-851, Apr. 2011.
Frazzitta et al. "Rehabilitation Treatment of Gait in Patients With Parkinson's Disease With Freezing: A Comparison Between Two Physical Therapy Protocols Using Visual and Auditory Cues With or Without Treadmill Training", Movement Disorders, 24(8): 1139-1143, 2009.
Frenkel-Toledo et al. "Treadmill Walking as an External Pacemaker to Improve Gait Rhythm and Stability in Parkinson's Disease", Movement Disorders, 20(9): 1109-1114, 2005.
Galica et al. "Subsensory Vibrations to the Feet Reduce Gait Variability in Elderly Fallers", Gait & Posture, 30: 383-387, 2009.
Ganz et al. "Will My Patient Fall?", The Journal of the American Medical Association, 297(1), 77-86, Jan. 3, 2009.
Giladi et al. Freezing Phenomenon in Patients With Parkinsonian Syndromes, Movement Disorders, 12(3): 302-305, 1997.
Giladi et al. "Understanding and Treating Freezing of Gait in Parkinsonism, Proposed Working Definition, and Setting the Stage", Movement Disorders, 23(2): S423-S425, 2008.
Hanakawa et al. "Enhanced Lateral Premotor Activity During Paradoxical Gait in Parkinson's Disease", Annals of Neurology, XP055188096, 45(3): 329-336, Mar. 1, 1999, p. 329, r-h Col., Last Para—p. 333, r-h Col., Para 1, Figs.
Hausdorff et al. "Impaired Regulation of Stride Variability", Experimental Brain Research, 149(2): 187-194, Mar. 2003.
Hausdorff et al. "Rhythmic Auditory Stimulation Modulates Gait Variability in Parkinson's Disease", European Journal of Neuroscience, 26(8): 2369-2375, 2007.
Herman et al. "The Dynamic Gait Index in Healthy Older Adults: The Role of Stair Climbing, Fear of Falling and Gender", Gait & Posture, 29: 237-241, 2009.
Higgins "Advances in Neurology", 67: 314, 1996.
Holden "Virtual Environments for Motor Rehabilitation: Review", CyberPsychology and Behavior, 8(3): 187-219, Jun. 1, 2005.
Hong et al. "Rotating Treadmill Training Reduces Freezing in Parkinson Disease: Preliminary Observations", Parkinsonism & Related Disorders, 14(4): 359-363, May 2008.
Iansek et al. "The Sequence Effect and Gait Festination in Parkinson Disease: Contributors to Freezing of Gait?", Movement Disorders, 21(9): 1419-1424, 2006.
Jacobs et al. "Changes in the Activity of the Cerebral Cortex Relate to Postural Response Modification When Warned of a Perturbation", Clinical Neurophysiology, 119(6): 1431-1442, Jun. 30, 2008.
Jacobs et al. "Knee Trembling During Freezing of Gait Represents Multiple Anticipatory Postural Adjustments", Experimental Neurology, 215(2): 334-341, Feb. 2009.
Kammerlind et al. "Effects of Balance Training in Elderly People With Nonperipheral Vertigo and Unsteadiness", Clinical Rehabilitation, 15: 463-470, 2001.

(56) References Cited

OTHER PUBLICATIONS

Lim et al. "Effects of External Rhythmical Cueing on Gait in Patients With Parkinson's Disease: A Systematic Review", Clinical Rehabilitation, 19(7):695-713, Jul. 2005.
Liu-Ambrose et al. "Resistance and Agility Training Reduce Fall Risk in Women Aged 75 to 85 With Low Bone Mass: A 6-Month Randomized, Controlled Trial", Journal of the American Geriatrics Society, 52(5): 657-665, May 2004.
Lord "Aging and Falls: Causes and Prevention", Journal of Musculoskeletal and Neuronal Interaction, 7(4): 347, 2007.
Lord et al. "Choice Stepping Reaction Time: A Composite Measure of Falls Risk in Older People", Journal of Gerontology, 56A(10): M627-M632, 2001.
Lord et al. "Home Environment Risk Factors for Falls in Older People and the Efficacy of Home Modifications", Age and Ageing, 35(2): ii55-ii59, 2006.
Lseki et al. "Gait Disturbance Associated With White Matter Changes: A Gait Analysis and Blood Flow Study", Neuroimage, 49(2): 1659-1666, 2010.
Maidan et al. "Doeas Heart Rate Change With Freezing of Gait in Patients With Parkinson's Disease?", Parkinsonism and Related Disorders, XP026909427, 16(Suppl.1): S39-S40, #136, Feb. 1, 2010. Abstract No. 136, p. S39, r-h Col.-p. S40, 1-h Col.
Mansfield et al. "A Perturbation-Based Balance Training Program for Older Adults: Study Protocol for a Randomised Controlled Trial", BMC Geriatrics, 7(12): 1-14, May 31, 2007.
McAndrew et al. "Walking Variability During Continuous Pseudo-Random Oscillations of the Support Surface and Visual Field", Journal of Biomechanics, 43(8): 1470-1475, 2010.
Mehrholz et al. "Treadmill Training for Patients With Parkinson's Disease (Review)", The Cochrane Collaboration, The Cochrane Library, 1: 1-31, 2010.
Menz et al. "A Structural Equation Model Relating Impaired Sensorimotor Function, Fear of Falling and Gait Patterns in Older People", Gait & Posture, 25: 243-249, 2007.
Mirelma et al. "Virtual Reality for Gait Training: Can It Induce Motor Learning to Enhance Complex Walking and Reduce Fall Risk in Patients With Parkinson's Disease?", The Journals of Gerontology, Series A, Biological Sciences and Medical Sciences, XP055187968, 66A(2): 234-240, Feb. 28, 2011. p. 235, 1-h Col., Para 3-p. 236, 1-h Col., Para 2, Fig.1.
Nakamura et al. "Postural and Gait Disturbance Correlated with Decreased Frontal Cerebral Blood Flow in Alzheimer Disease", Alzheimer Disease and Associated Disorders 11(3): 132-139, Sep. 1, 1997.
Nieuwboer et al. "Abnormalities of the Spatiotemporal Characteristics of Gait at the Onset of Freezing in Parkinson's Disease", Movement Disorders, 16(6): 1066-1075, 2001.
Nieuwboer et al. "Electromyographic Profiles of Gait Prior to Onset of Freezing Episodes in Patients With Parkinsons's Disease", Brain, 127(7): 1650-1660, 2004.
Nieuwboer et al. "Reliability of the New Freezing of Gait Questionnaire: Agreement Between Patients With Parkinson's Disease and Their Carers", Gait & Posture, 30: 459-463, 2009.
Nutt et al. "Freezing of Gait: Moving Forward on a Mysterious Clinical Phenomenon", The Lancet Neurology, 10: 734-744, 2011.
Nyberg et al. "Development of a Virtual Reality System to Study Tendency of Falling Among Older People", Proceedings of the 5th International Conference on Disability, Virtual Reality and Associated Technologies, ICDVRAT 2004, Oxford, UK, Sep. 20-22, 2004, p. 315-320, Sep. 22, 2004.
Park et al. "Development of a VR-Based Treadmill Control Interface for Gait Assessment of Patients With Parkinson's Disease", 2011 IEEE International Conference on Rehabilitation Robotics, Rehab Week Zurich, ETH Zurich Science Sity, Switzerland, Jun. 29-Jul. 1, 2011, p. 1-5, Jul. 1, 2011.
Plotnik et al. "Bilateral Coordination of Walking and Freezing of Gait in Parkinson's Disease", Europeam Journal of Neuroscience, 27: 1999-2006, 2008.
Plotnik et al. "Is Freezing of Gait in Parkinson's Disease Related to Asymmetric Motor Function", Annals of Neurology, 57(5): 656-663, May 2005.
Plotnik et al. "The Role of Gait Rhythmicity and Bilateral Coordination of Stepping in the Pathophysiology of Freezing of Gait in Parkinson's Disease", Movement Disorders, 23(2): S444-S450, 2008.
Rochester et al. "Targeting Dopa-Sensitive and Dopa-Resistant Gait Dysfunction in Parkinson's Disease: Selective Responses to Internal and External Cues", Movement Disorders, 23(3): 430-435, 2011.
Rubinstein et al. "The Power of Cueing to Circumvent Dopamine Deficits: A Review of Physical Therapy Treatment of Gait Disturbances in Parkinson's Disease", Movement Disorders, 17(6): 1148-1160, 2002.
Schaafsma et al. "Characterization of Freezing of Gait Subtypes and the Response of Each to Levodopa in Parkinson's Disease", European Journal of Neurology, 10: 391-398, 2003.
Snijders et al. "Clinimetrics of Freezing of Gait", Movement Disorders, 23(2): S468-S474, 2008.
Snijders et al. "Cycling for Freezing of Gait", The New England Journal of Medicine, 362: e46, Apr. 1, 2010.
Spildooren et al. "Freezing of Gait in Parkinson's Disease:The Impact of Dual-Tasking and Turning", Movement Disorders, 25(15): 2563-2570, 2010.
St George et al. "Sleep Quality and Falls in Older People Living in Self-and Assisted-Care Villages", Gerontology, 55: 162-168, 2009.
Thurman et al. Practice Parameter: Assessing Patients in a Neurology Practice for Risk of Falls (An Evidence-Based Review): Report of the Quality Standards Subcommittee of the American Academy of Neurology, Neurology, 70: 473-479, 2008.
Verghese et al. "Validity of Divided Attention Tasks in Predicting Falls in Older Individuals: A Preliminary Study", Journal of the American Geriatrics Society, 50(9): 1572-1576, Sep. 2002.
Visser et al. "The Clinical Utility of Posturography", Clinical Neurophysiology, 119: 2424-2436, 2008.
Voukelatos et al. "A Randomized, Controlled Trial of tai chi for the Prevention of Falls: the Central Sydney tai chi Trial", Journal of the American Geriatrics Society, 55(8): 1185-1191, 2007.
Walker et al. "Virtual Reality-Enhanced Partial Body Weight-Supported Treadmill Training Poststroke: Feasibility and Effectiveness in 6 Subjects", Archives of Physical Medicine and Rehabilitation, 91(1): 115-122, Jan. 2010.
Whitney et al. "Streamlining Assessment and Intervention in a Falls Clinic Using the Timed Up and Go Test and Physiological Profile Assessments", Age and Ageing, 34: 567-571, 2005.
Yang et al. "Vitruality Reality-Based Training Improves Community Ambulation in Individuals With Stroke: A Randomized Controlled Trial", Gait & Posture, XP022940963, 28(2): 201-206, Aug. 1, 2008. p. 202, r-h col., Para 1-p. 203, 1-h Col., Para 2.
Ziegler et al. "A New Rating Instrument to Assess Festination and Freezing Gait in Parkinsonian Patients", Movement Disorders, 25(8): 1012-1018, 2010.
Official Action Dated May 17, 2018 From the US Patent and Trademark Office Re. U.S. Appl. No. 14/350,567. (32 pages)
Chen et al. "Stepping Over Obstacles: Dividing Attention Impairs Performance of Old More Than Young Adults", The Journals of Gerontology Series A: Biological Sciences and Medical Sciences, 51A(3): M116-M122, May 1, 1996.
Fung et al. "A Treadmill and Motion Coupled Virtual Reality System for Gait Training Post-Stroke.", CyberPsychology & Behavior, 9(2): 157-162, Published Online Apr. 26, 2006.
Rand et al. "Virtual Reality Rehabilitation for All: Vivid GX Versus Sony PlayStation II EyeToy", 5th International Conference on Disability, Virtual Environments and Assoc. Technologies, pp. 87-94, Sep. 2004.
Weerdesteyn et al. "Gait Adjustments in Response to an Obstacle are Faster Than Voluntary Reactions", Human Movement Science, 23(3-4): 351-363, Oct. 2004.
Office Action dated May 31, 2018 From the Israel Patent Office Re. Application No. 231996 and Its Translation Into English. (4 Pages).
Official Action dated Oct. 18, 2018 From the US Patent and Trademark Office Re. U.S. Appl. No. 14/350,567. (25 pages).

(56) References Cited

OTHER PUBLICATIONS

Requisition by the Examiner dated Jul. 30, 2018 From the Innovation, Science and Economic Development Canada, Canadian Intellectual Property Office Re. Application No. 2,851,443. (7 Pages).

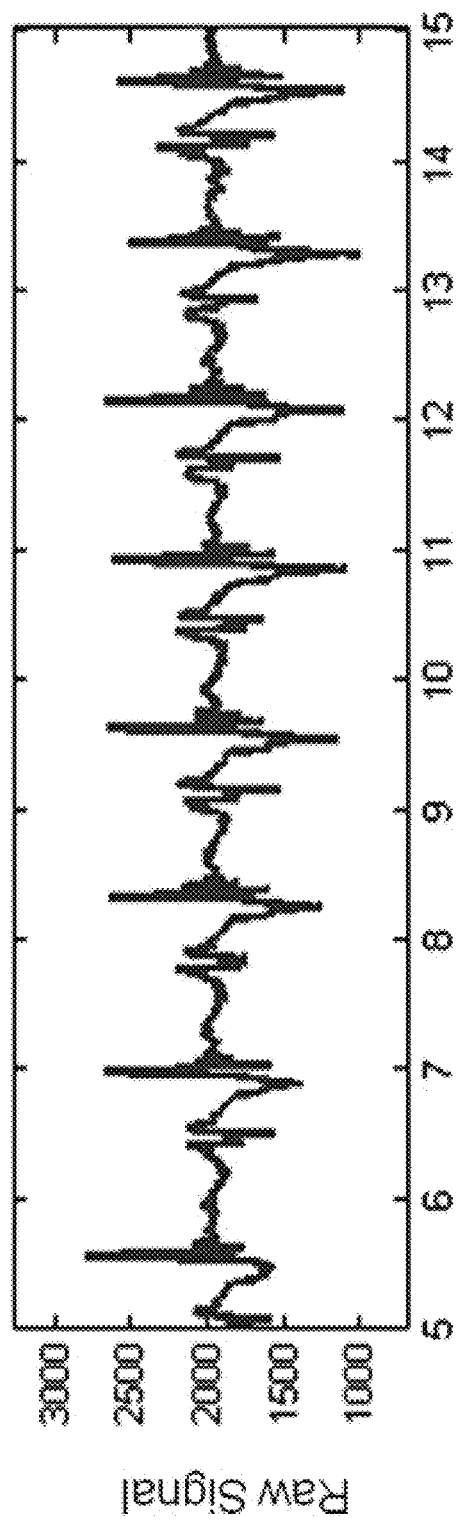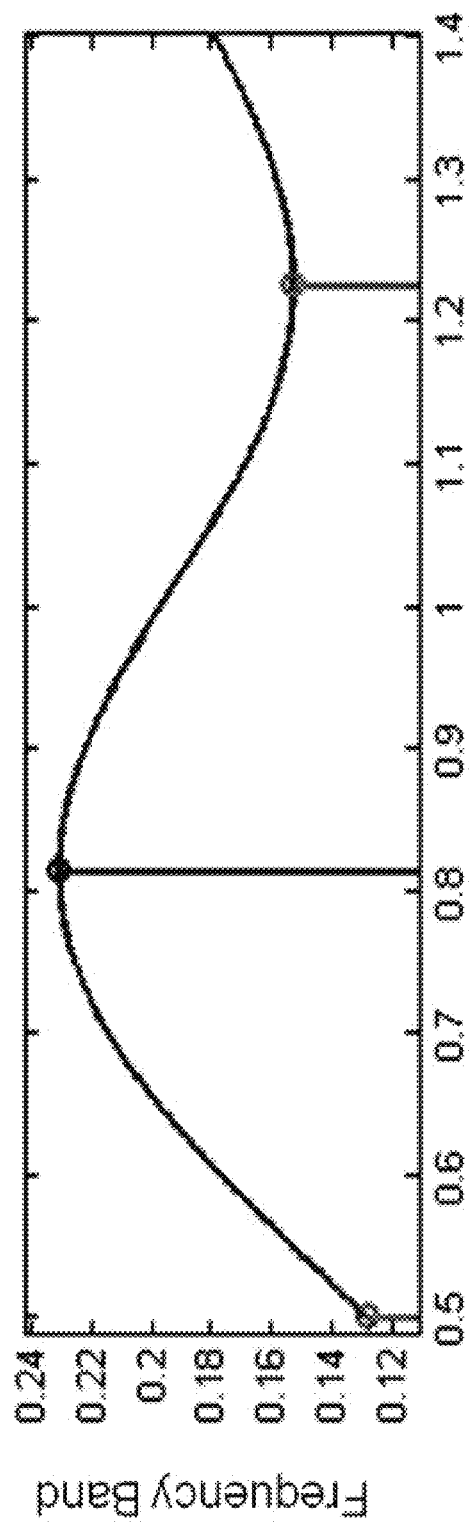
FIG. 7

Table 1: FOG quantification and scoring

| Score | Level | Description |
|---|---|---|
| 0 | No FOG | |
| 1 | Mild FOG severity | Rare freezing, with high complexity tasks or environments. Gait dynamics within normal range |
| 2 | Moderate FOG severity | Occasional freezing could be in low complex environments, while attention is distracted, or as a result of provocation. Gait dynamics are slightly abnormal. |
| 3 | Severe FOG | Frequent freezing episodes, on low level provocation, simple environments and cognitive challenges. High gait variability and asymmetry. |

FIG. 14

Table 2: patients characteristics

| Subject number | Age (y) | Gender | Age at disease onset (y) | Disease duration (y) | UPDRS total | UPDRS motor | Falls (per year) | FOG Q score | MOCA | Gait speed (m/s) |
|---|---|---|---|---|---|---|---|---|---|---|
| 1 | 64 | M | 59 | 5 | 42 | 23 | 2 | 13 | 25 | 1.3 |
| 2 | 73 | M | 58 | 15 | 67 | 45 | 5 | 28 | 23 | 1.2 |
| 3 | 55 | M | 38 | 17 | 54 | 28 | 4 | 22 | 24 | 1.2 |
| 4 | 63 | M | 59 | 4 | 63 | 23 | 20 | 19 | 23 | 1 |
| Mean±SD | 63.7±7.3 | 100% | 53.5±10.3 | 10.2±6.7 | 61.3±6.6 | 32±11.5 | 9.6±8.9 | 23±4.5 | 23.3±0.5 | 1.17±0.1 |

FIG. 15E

| Table 3: Measures of consistency | | | | |
|---|---|---|---|---|
| Patient | Amplitude (prs) | Width (prs) | CV (%) | PCI (%) |
| 1 | 0.31 ± 0.03 | 2.87 ± 0.40 | 1.65% | 5.69% |
| 2 | 0.21 ± 0.01 | 1.01 ± 0.6 | 1.82% | 5.94% |
| 3 | 0.21 ± 0.05 | 2.4 ± 0.7 | 5.33 % | 6.48% |
| 4 | 0.10 ± 0.001 | 3.2 ± 0.8 | 6.38 % | 7.53% |
| Control | 0.44 ± 0.02 | 0.95 ± 0.005 | 0.84 % | 1.4% |
| | (higher values reflect more consistency) | (lower values reflect less consistency) | (lower values reflect greater rhythmicity) | (lower values reflect more left-right consistency) |

FIG. 16

| Table 4: Patient 1 –test parameters | | | | | | |
|---|---|---|---|---|---|---|
| | Trial 1 – difficult | Trial 2- moderate | Trial 3- environment | Trial 4- FOG challenges | Trial 5- cognitive | Total |
| Gait speed | 1.30 | 1.30 | 1.30 | 1.30 | 1.30 | 1.30 |
| TM speed | 1.10 | 1.10 | 1.10 | 1.10 | 1.10 | 1.10 |
| FOG detection | 10.00 | 7.00 | 10.00 | 0.00 | 1.00 | 28.00 |
| FOG detected by researcher | 4.00 | 5.00 | 4.00 | 0.00 | 1.00 | 14.00 |
| FOG on video | 2.00 | 2.00 | 3.00 | 0.00 | 1.00 | 8.00 |
| FOG during provocation | 1-tunnel | 0 | 2 (bridge and gate) | 0 | 0 | 3 |
| obstacles passed | 22.00 | 24.00 | 33.00 | 0.00 | 12.00 | 91.00 |
| obstacles failed | 31.00 | 27.00 | 21.00 | 0.00 | 39.00 | 118.00 |
| hurdles | 17.00 | 20.00 | 14.00 | 0.00 | 27.00 | 78.00 |
| puddles | 14.00 | 7.00 | 7.00 | 0.00 | 12.00 | 40.00 |
| Cost environment | // | // | 3.14 | 2.86 | // | 0.28 |
| Cost DT | // | // | // | 2.86 | 3.33 | 0.47 |
| Width of dominant frq. | // | // | // | 2.84 | // | 2.84 |
| Symmetry ratio | | | | | | 99.00 |
| PCI | | | | | | 5.67% |
| FOG severity score | | | | | | 2.0 |

FIG. 17

| Table 5: Patient 2 – test parameters | | | | | | |
|---|---|---|---|---|---|---|
| | Trial 1 – difficult | Trial 2 – moderate | Trial 3 – environment | Trial 4 – FOG challenges | Trial 5 – cognitive | Total |
| Gait speed | 1.2 | 1.2 | 1.2 | 1.2 | 1.2 | 1.2 |
| TM speed | 1.0 | 1.0 | 1.0 | 1.0 | 1.0 | 1.0 |
| FOG detection | 4.0 | 6.0 | 6.0 | 0.0 | 4.0 | 20.0 |
| FOG detected by researcher | 0.0 | 2.0 | 3.0 | 0.0 | 2.0 | 7.0 |
| FOG on video | 0.0 | 2.0 | 2.0 | 0.0 | 2.0 | 6.0 |
| FOG during provocation | 0 | 1-tunnel | 2 (bridge and gate) | 0 | 2 (bridge and gate) | 5 |
| Obstacles passed | 3.0 | 6.0 | 0.0 | 0.0 | 3.0 | 12.0 |
| Obstacles failed | 14.0 | 22.0 | 21.0 | 0.0 | 19.0 | 76.0 |
| Hurdles | 10.0 | 14.0 | 11.0 | 0.0 | 10.0 | 45.0 |
| Puddles | 4.0 | 8.0 | 10.0 | 0.0 | 9.0 | 31.0 |
| Cost environments | // | // | 0.7 | 1.0 | // | -0.3 |
| Cost DT | // | // | // | 1.0 | 1.3 | 0.3 |
| Width of dominant frq | // | // | // | 1.0 | // | 1.0 |
| Symmetry ratio | | | | | | 98.0 |
| PCI | | | | | | 5.94% |
| FOG severity score | | | | | | 2.0 |

FIG. 18

| Table 6: Patient 3 test parameters | | | | | | |
|---|---|---|---|---|---|---|
| | Trial 1 – difficult | Trial 2- moderate | Trial 3- environment | Trial 4- FOG challenges | Trial 5- Cognitive | Total |
| Gait speed | 1.2 | 1.2 | 1.2 | 1.2 | 1.2 | 1.2 |
| TM speed | 1.0 | 1.0 | 1.0 | 1.0 | 1.0 | 1.0 |
| FOG detection | 4 | 1 | 0 | 1 | 5 | 11.0 |
| FOG detected by researcher | 2 | 0 | 0 | 0 | 5 | 7.0 |
| FOG on video | 2 | 0 | 0 | 0 | 3 | 5.0 |
| FOG during provocation | 2 (bridge and tunnel) | 1-tunnel | 0 | 0 | 3 (bridge and gate) | 6.0 |
| obstacles passed | 2 | 8 | 6 | 0 | 7 | 23.0 |
| obstacles failed | 22 | 11 | 17 | 0 | 27 | 77.0 |
| hurdles | 12 | 7 | 11 | 0 | 17 | 47.0 |
| puddles | 10 | 6 | 6 | 0 | 10 | 32.0 |
| Cost environment | // | // | 1.8 | 2.4 | // | -0.6 |
| Cost DT | // | // | // | 2.4 | 0.8 | -0.6 |
| Width of dominant frq | // | | | 2.4 | // | 2.4 |
| Symmetry ratio | | | | | | 33.0 |
| PCI | | | | | | 6.48 |
| FOG severity score | | | | | | 3.0 |

FIG. 19

| Table 7: Patient 4 test parameters | | | | | | |
|---|---|---|---|---|---|---|
| | Trial 1 – difficult | Trial 2- moderate | Trial 3- environment | Trial 4- FOG challenges | Trial 5- cognitive | Total |
| Gait speed | 1.2 | 1.2 | 1.2 | 1.2 | 1.2 | 1.2 |
| TM speed | 1.0 | 1.0 | 1.0 | 1.0 | 1.0 | 1.0 |
| FOG detection | 5 | 3 | 5 | 2 | 3 | 18.0 |
| FOG detected by researcher | 5 | 3 | 4 | 2 | 3 | 17.0 |
| FOG on video | 5 | 1 | 4 | 2 | 3 | 15.0 |
| FOG during provocation | 1-tunnel | 2-tunnel and bridge | Obstacles only | 0 | Obstacles | 3 |
| obstacles passed | 4 | 6 | 5 | 0 | 2 | 17.0 |
| obstacles failed | 18 | 19 | 13 | 0 | 14 | 64.0 |
| hurdles | 10 | 10 | 10 | 0 | 6 | 36.0 |
| puddles | 8 | 9 | 3 | 0 | 8 | 28.0 |
| Cost environments | // | // | 1.6 | 2.5 | // | -0.9 |
| Cost DT | // | // | // | 2.5 | 1.5 | -1.0 |
| Width of dominant frq | // | | | 2.5 | // | 2.5 |
| Symmetry ratio | | | | | | 64.0 |
| PCI | | | | | | 7.58% |
| FOG severity score | | | | | | 3.0 |

FIG. 20

FREEZING OF GAIT (FOG), DETECTION, PREDICTION AND/OR TREATMENT

RELATED APPLICATIONS

This application is a continuation of U.S. patent application Ser. No. 14/350,569 filed on Apr. 9, 2014, which is a National Phase of PCT Patent Application No. PCT/IB2012/055454 having International Filing Date of Oct. 9, 2012, which is related to co-filed PCT Patent Application No. PCT/IB2012/055453, titled "VIRTUAL REALITY FOR MOVEMENT DISORDER DIAGNOSIS AND/OR TREATMENT", the contents of which are incorporated herein by reference in their entirety, and also related to using virtual reality displays for diagnosing and/or treating gait disorders, for example by provoking gait disorder appearance and/or for training. Such systems may be used in the context of the present application, as well.

This application is a continuation of U.S. patent application Ser. No. 14/350,569 filed on Apr. 9, 2014, which is a National Phase of PCT Patent Application No. PCT/IB2012/055454 having International Filing Date of Oct. 9, 2012, which claims the benefit of priority under 35 USC 119(e) of U.S. Provisional Patent Application Nos. 61/545,161 and 61/545,164 both filed on Oct. 9, 2011. The contents of the above applications are all incorporated by reference as if fully set forth herein in their entirety.

FIELD AND BACKGROUND OF THE INVENTION

The present invention, in some embodiments thereof, relates to methods and/or apparatus for detecting and/or treating gait disorders, in particular episodic gait disorders, more particularly, but not exclusively, freezing of gait disorders, whether associated with Parkinson's disease or not.

Freezing of gait (FOG) is a paroxysmal gait disturbance, a sudden, transient and unpredictable interruption of walking. FOG typically manifests as a sudden and transient inability to move. The patient attempts to move forward, inexplicably however, he/she is unable to. Patients report that their feet are "glued to the ground". FOG is a debilitating phenomenon that significantly reduces functional independence and often leads to wheelchair use.

The population which suffers mostly from FOG are subjects with Parkinson's disease (PD). FOG is common in subjects with advanced Parkinson's disease (PD), however one should bear in mind that FOG is a symptom complex that occurs in several disorders which also often involve cognitive impairment, e.g., progressive supranuclear palsy, multiple system atrophy, corticobasal degeneration, dementia with Lewy Bodies and higher level gait disorders. Manifestation of FOG is variable within and across subjects, yet a few subtypes have been described. These include, for example, freezing that occurs at the start of walking (i.e., gait initiation), during turns, when passing tight quarters and also during simple walking in an open runway. FOG has a grave impact on quality of life as it is largely associated with falls, interferes with daily living functions, and causes reduced activity and self-imposed social isolation.

The pathophysiology behind the symptom is not clear. A number of theories have been proposed mainly in reference to patients with PD. Briefly, the breakup of regular gait that results in a subject who is virtually 'frozen' in one place lacking the ability to produce effective progression, is hypothesized to stem from deterioration of certain gait features, (or inability to start the operation of these gait features in case FOG occurs at the start of walking) to an extent that gait cannot be regulated. Gait features that were implicated with FOG are gait rhythmicity, left-right stepping coordination, step length scaling, gait symmetry and dynamic control of postural stability. Each of these gait features is compromised even during the functional periods of locomotion preformed by PD patients that suffer from FOG (PD+FOG), and their background impaired condition is related to the pathological condition of the brain in PD. For example, bilateral coordination of gait is impaired in PD, possibly due to the un-even neuronal loss seen on both sides of the brain in this neurodegenerative disease. Major dopaminergic depletion in the Basal Ganglia, a brain region that normally facilitates movement scaling, is most likely behind the step scaling problem in this disease. It was also hypothesized that additional pathological conditions overlap with these gait impairments to distinguish those PD patients who will suffer from freezing from those who will not. For example, reduced cognitive capacities, in particular in the executive function domains, were associated with and believed to contribute to freezing in PD.

Methods for diagnosing and treating FOG are quite limited. Often patients who report many freezing incidents during their daily routine fail to exhibit even one under examination at the neurologist's office, most likely due to psychological effects. Therefore the effectiveness of proposed treatments is evaluated only in a limited manner. Even among patients who do present with FOG in the clinic, it is difficult to quantify the magnitude of the problem. This limits the ability to evaluate the effectiveness of any treatments attempts.

Subjective assessment is currently used to determine the severity of freezing. Several questionnaires are in common use in clinical practice that assess if freezing occurs, how often and under which circumstances. These quaternaries sometimes obscure the correct clinical pictures since sometimes patients change their reports between consecutive visits that are separated by only a short period of time. Actually, this problem led to the creation of a questionnaire in which spouses and caregivers both provide information. Recently, mobility sensors were suggested alternative for the assessment of the FOG burden. Current treatments are based on pharmacological treatments. Recently some have suggested using surgical implantation of stimulating electrodes to specific parts of the brain, however, this is not widely accepted, is quite invasive, and the evidence for its efficacy is not yet strong.

FOG is generally not well addressed by current treatment approaches. Immediate, small, short-term improvements in FOG have been demonstrated in a handful of studies. Many of these focus on the use of visual or auditory cues to facilitate movement and reduce FOG. There is evidence that PD+FOG may respond differently to cues than PD-FOG and that appropriate cues can, while present, result in improved velocity and stride length and reduced FOG. A large randomized trial examining the effects of cueing on FOG demonstrated slight improvements in FOG (5.5% reduction) but little retention of benefit six weeks after training. The effects of a comprehensive physical therapy program that included cueing on FOG, demonstrating improvements in FOG immediately following a 6-week intervention but a return to baseline levels of FOG one month later. Preliminary work on turning, e.g., when the subject turns left, right or in a circle, suggests that rotating treadmill training may have a dramatic effect on FOG when the subjects walk in normal daily conditions after the intervention.

To date, methods for diagnosing and treating FOG are quite limited. Often patients who report many freezing episodes during their daily routine fail to exhibit them under testing or examination conditions such as at the neurologist office. Therefore the effectiveness of prescribed treatments is evaluated only in a limited manner. Even among patients who do present with FOG in the clinic, it is difficult to quantify the magnitude of the problem as it is episodic. In addition, due, in part, to the variable nature of the appearance of the symptom, standardized treatment approaches are not effective.

REFERENCE LIST RELATED (ALSO) TO MECHANISMS OF FREEZING OF GAIT

1. Nutt J G, Bloem B R, Giladi N, Hallett M, Horak F B, Nieuwboer A. Freezing of gait: moving forward on a mysterious clinical phenomenon. Lancet Neurol. 2011; 10(8):734-44.
2. Plotnik M, Hausdorff J M. The role of gait rhythmicity and bilateral coordination of stepping in the pathophysiology of freezing of gait in Parkinson's disease. Mov Disord. 2008; 23 Suppl 2:S444-S450.
3. Hausdorff J M, Schaafsma J D, Balash Y, Bartels A L, Gurevich T, Giladi N. Impaired regulation of stride variability in Parkinson's disease subjects with freezing of gait. Exp. Brain Res. 2003; 149(2):187-94.
4. Plotnik M, Giladi N, Hausdorff J M. Bilateral Coordination of Walking and Freezing of Gait in Parkinson's Disease. Eur. J. Neurosci. 2008; 27(8):1999-2006.
5. Plotnik M, Giladi N, Balash Y, Peretz C, Hausdorff J M. Is freezing of gait in Parkinson's disease related to asymmetric motor function? Ann. Neurol. 2005; 57(5): 656-63.
6. Jacobs J V, Nutt J G, Carlson-Kuhta P, Stephens M, Horak F B. Knee trembling during freezing of gait represents multiple anticipatory postural adjustments. Exp. Neurol. 2009; 215(2):334-41.
7. Chee R, Murphy A, Danoudis M, Georgiou-Karistianis N, Iansek R. Gait freezing in Parkinson's disease and the stride length sequence effect interaction. Brain 2009; 132(Pt 8):2151-60.
8. Iansek R, Huxham F, McGinley J. The sequence effect and gait festination in Parkinson disease: Contributors to freezing of gait? Mov Disord. 2006; 21(9):1419-24.
9. Nieuwboer A, Dom R, De Weerdt W, Desloovere K, Fieuws S, Broens-Kaucsik E. Abnormalities of the spatiotemporal characteristics of gait at the onset of freezing in Parkinson's disease. Mov Disord. 2001; 16(6):1066-75.
10. Nieuwboer A, Dom R, De Weerdt W, Desloovere K, Janssens L, Stijn V. Electromyographic profiles of gait prior to onset of freezing episodes in patients with Parkinson's disease. Brain 2004; 127(Pt 7):1650-60.
11. Spildooren J, Vercruysse S, Desloovere K, Vandenberghe W, Kerckhofs E, Nieuwboer A. Freezing of gait in Parkinson's disease: the impact of dual-tasking and turning. Mov Disord. 2010; 25(15):2563-70.
12. Fahn S. The freezing phenomenon in Parkinsonism. Negative motor phenomenon. 1995; 67:53-63.

REFERENCE LIST RELATED (ALSO) TO TREATMENT OF FREEZING OF GAIT

1. Fasano A, Herzog J, Seifert E, Stolze H, Falk D, Reese R et al. Modulation of gait coordination by subthalamic stimulation improves freezing of gait. Mov Disord. 2011; 26(5):844-51.
2. Mehrholz J, Friis R, Kugler J, Twork S, Storch A, Pohl M. Treadmill training for patients with Parkinson's disease Cochrane Database Syst Rev. 2010: 20; (1):CD007830.
3. Hong M, Earhart G M. Rotating treadmill training reduces freezing in Parkinson disease: preliminary observations. Parkinsonism. Relat Disord. 2008; 14(4):359-63.
4. Lim I, van Wegen E, de Goede C, Deutekom M, Nieuwboer A, Willems A et al. Effects of external rhythmical cueing on gait in patients with Parkinson's disease: a systematic review. Clin. Rehabil. 2005; 19(7):695-713.
5. Bachlin M, Plotnik M, Roggen D, Giladi N, Hausdorff J M, Troster G. A wearable system to assist walking of Parkinson s disease patients. Methods Inf. Med. 2010; 49(1):88-95.
6. Giladi N, Nieuwboer, A. Understanding and treating freezing of gait in Parkinsonism, proposed working definition, and setting the stage. Movement Disorders. 2008; 23(Suppl. 2):S423-S5.
7. Snijders A H, Bloem B R. Images in clinical medicine. Cycling for freezing of gait. N Engl J Med. 2010 April; 362(13):e46.
8. Brichetto G, Pelosin, E., Marchese, R., Abbruzzese, G. Evaluation of physical therapy in parkinsonian patients with freezing of gait: a pilot study. Clinical Rehab. 2006; 20:31-5.
9. Frazzitta G, Maestri R, Uccellini D, Bertotti G, Abelli P. Rehabilitation treatment of gait in patients with Parkinson's disease with freezing: a comparison between two physical therapy protocols using visual and auditory cues with or without treadmill training. Mov Disord. 2009 June; 24(8):1139-43.
10. Lim I, van Wegen E, de Goede C, Deutekom M, Nieuwboer A, Willems A et al. "Effects of external rhythmical cueing on gait in patients with Parkinson's disease: a systematic review". Clin. Rehabil. 2005; 19(7): 695-713.
11. J M Hausdorff, J Lowenthal, T Herman, L Gruendlinger, C Peretz, N Giladi. "Rhythmic auditory stimulation modulates gait variability in Parkinson's disease". Eur J Neurosci. 2007: 26:2369-2375.
12. S. Frenkel-Toledo, N. Giladi, C. Peretz T. Herman, L. Gruendlinger, J. M. Hausdorff. "Treadmill walking as a pacemaker to improve gait rhythm and stability in Parkinson's disease". Mov Disord 2005; 20:1109-1114.
13. T. Rubenstein, N. Giladi, J. M. Hausdorff. "The power of cueing circumvent dopamine deficits: A brief review of physical therapy treatment of gait disturbances in Parkinson's disease". Mov Disord, Vol. 17, pp. 1148-1160, 2002.
14. "Targeting dopa-sensitive and dopa-resistant gait dysfunction in Parkinson's disease: selective responses to internal and external cues". Rochester L, Baker K, Nieuwboer A, Burn D. Mov Disord. 2011 Feb. 15; 26(3):430-5. doi: 10.1002/mds.23450. Epub 2010 Dec. 13.

REFERENCE LIST RELATED (ALSO) TO ASSESSMENT OF FREEZING OF GAIT

1. Schaafsma J D, Balash Y, Gurevich T, Bartels A L, Hausdorff J M, Giladi N. Characterization of freezing of gait subtypes and the response of each to levodopa in Parkinson's disease. Eur. J Neurol 2003; 10(4):391-8.
2. Snijders A H, Nijkrake M J, Bakker M, Munneke M, Wind C, Bloem B R. Clinimetrics of freezing of gait. Mov Disord. 2008; 23 Suppl 2:S468-S474.

3. Moore S T, Macdougall H G, Ondo W G. Ambulatory monitoring of freezing of gait in Parkinson's disease. J. Neurosci. Methods 2008; 167(2):340-8.
4. Giladi N, Kao, R., and Fahn, S. Freezing phenomenon in patients with Parkinsonian Syndromes. MovDisord. 1997; 12:302-5.
5. Ziegler K, Schroeteler F, Ceballos-Baumann A O, Fietzek U M. A new rating instrument to assess festination and freezing gait in Parkinsonian patients. Mov Disord. 2010 June; 25(8):1012-8.
6. Bachlin M, Plotnik M, Roggen D, Maidan I, Hausdorff J M, Giladi N et al. Wearable assistant for Parkinson's disease patients with the freezing of gait symptom. IEEE Trans. Inf. Technol. Biomed. 2010; 14(2):436-46.
7. Giladi N, Shabtai H, Simon E S, Biran S, Tal J, Korczyn A D. Construction of freezing of gait questionnaire for patients with Parkinsonism. Parkinsonism Relat Disord. 2000 Jul. 1; 6(3):165-170.
8. Nieuwboer A, Rochester L, Herman T, Vandenberghe W, Emil G E, Thomaes T, Giladi N. Reliability of the new freezing of gait questionnaire: agreement between patients with Parkinson's disease and their carers. Gait Posture. 2009 November; 30(4):459-63. Epub 2009 Aug. 5.
9. Moore S T, Macdougall H G, Ondo W G. "Ambulatory monitoring of freezing of gait in Parkinson's disease". J. Neurosci. Methods 2008; 167(2):340-8.
10. J. M. Hausdorff, J. Balash, N. Giladi "Time series analysis of leg movements during freezing of gait in Parkinson's disease: akinesia, rhyme or reason?" Physica A: Stat Mechanics & Appl 2003; 321: 565-570.
11. Exp Neurol. 2009 February; 215(2):334-41. Knee trembling during freezing of gait represents multiple anticipatory postural adjustments. Jacobs J V, Nutt J G, Carlson-Kuhta P, Stephens M, Horak F B.

SUMMARY OF THE INVENTION

The present invention is related to diagnosis and/or treatment of episodic gait disorders, for example freezing of gait (FOG), for example, by provoking freezing of gait and/or measuring changes in gait due to such provoking. Optionally or alternatively, measurements of gait are used to identify an increased risk for imminent FOG and preventive action is optionally taken.

There is provided in accordance with an exemplary embodiment of the invention, a method of assessing FOG (Freezing of Gait), comprising:

providing a stimulus designed to increase a likelihood of FOG in some subjects, to a subject; and monitoring the effect of the stimulus on the subject.

In an exemplary embodiment of the invention, the method comprises identifying near-FOG situations based on said monitoring. Optionally or alternatively, the method comprises identifying FOG situations based on said monitoring. Optionally or alternatively, the method comprises repeating said providing in response to said monitoring. Optionally, said repeating is adjusted to provide a desired rate or amount of FOG or near-FOG situations.

In an exemplary embodiment of the invention, the method comprises testing an efficacy of a treatment by repeating said providing and said monitoring after said treatment is provided to the subject. Optionally, the method comprises selecting a treatment based on relative efficacy of different treatments tried.

In an exemplary embodiment of the invention, comprises provoking using virtual reality. Optionally, said display includes one or more narrowings of a pathway.

In an exemplary embodiment of the invention, providing comprises encouraging one or more of turning, rhythmic movement and gait length change.

In an exemplary embodiment of the invention, monitoring comprises measuring one or more gait characteristic.

In an exemplary embodiment of the invention, the method is applied as a standard test for FOG.

In an exemplary embodiment of the invention, the method comprises selecting a treatment based on said monitoring.

In an exemplary embodiment of the invention, the method comprises generating a FOG burden for said subject based on said monitoring.

There is provided in accordance with an exemplary embodiment of the invention, a method to train for FOG, comprising:

providing a plurality of stimuli selected to increase a likelihood of FOG in a particular subject, to that subject. Optionally, the method comprises selecting said situations by a standardized testing using a VR system. Optionally or alternatively, said providing is at a patient's location of daily activities and during such activities.

There is provided in accordance with an exemplary embodiment of the invention, a method of treating FOG, comprising:

automatically identifying an increased likelihood of an upcoming FOG event in a patient; and providing a cue to said patient in a manner which prevents and/or assist in overcoming said FOG event.

There is provided in accordance with an exemplary embodiment of the invention, a system for FOG assessment and/or training, comprising:

(a) a VR display system;

(b) a controller programmed to provide on said VR display system one or more scenes designed to encourage FOG. Optionally, the system comprises one or more physiological and/or movement sensors which provide feedback to said controller and which said controller uses to vary a display in connection with modifying a FOG likelihood.

There is provided in accordance with an exemplary embodiment of the invention, a system for assisting with FOG, comprising:

(a) a movement sensor;

(b) an output;

(c) a controller configured to process a signal from said sensor to detect an increase in likelihood of FOG and generate a signal on said output in response thereto. Optionally, said system is designed to be worn and wherein said output signal is suitable to prevent and/or assist in overcoming FOG. Optionally or alternatively, said controller is programmed to providing a training in FOG avoidance to a subject.

There is provided in accordance with an exemplary embodiment of the invention a method of measuring FOG (Freezing of Gait), comprising:

providing a stimulus designed to increase a likelihood of FOG in some subjects, to a subject; and monitoring the effect of the stimulus on the subject. Optionally, the method comprises identifying near-FOG situations based on said monitoring.

In an exemplary embodiment of the invention, the method comprises identifying FOG situations based on said monitoring. Optionally, the method comprises calculating a FOG Index (FI) based on a ratio between the power in gait frequencies and power in FOG frequencies.

Optionally or alternatively, the method comprises calculating a FOG Index (FI) based on a k-means method.

In an exemplary embodiment of the invention, the method comprises adapting said identifying to said subject.

In an exemplary embodiment of the invention, the method comprises identifying FOG based on a combination of two or more of acceleration, gyroscope, other movement sensors, EMG, APAs, heart rate and/or cerebral signals.

In an exemplary embodiment of the invention, the method comprises cuing said subject with FOG averting stimuli during said monitoring.

In an exemplary embodiment of the invention, said monitoring comprises monitoring on a locomotion system.

In an exemplary embodiment of the invention, the method comprises repeating said providing in response to said monitoring. Optionally, said repeating is modified in response to said monitoring in a closed control loop. Optionally, said repeating is adjusted to provide a desired rate or amount of FOG or near-FOG situations.

In an exemplary embodiment of the invention, the method comprises testing an efficacy of a treatment by repeating said providing and said monitoring after said treatment is provided to the subject. Optionally, the method comprises selecting a treatment based on relative efficacy of different treatments tried.

In an exemplary embodiment of the invention, providing comprises provoking using virtual reality. Optionally, said display includes one or more narrowings of a pathway.

In an exemplary embodiment of the invention, providing comprises encouraging one or more of turning, rhythmic movement and gait length change.

In an exemplary embodiment of the invention, monitoring comprises measuring one or more gait characteristic.

In an exemplary embodiment of the invention, the method is applied as a standard test for FOG.

In an exemplary embodiment of the invention, the method comprises selecting a treatment based on said monitoring.

In an exemplary embodiment of the invention, the method comprises generating a FOG burden for said subject based on said monitoring.

In an exemplary embodiment of the invention, monitoring comprises detecting a sub-clinical FOG state.

In an exemplary embodiment of the invention, monitoring comprises monitoring a change in blood flow in the brain.

In an exemplary embodiment of the invention, the method comprises quantifying a future risk of FOG based on said monitoring.

In an exemplary embodiment of the invention, the method comprises quantifying a number and degree of FOG events during said monitoring.

There is provided in accordance with an exemplary embodiment of the invention a method to train for FOG, comprising:

providing a plurality of stimuli selected to increase a likelihood of FOG in a particular subject subjects, to that subject. In an exemplary embodiment of the invention, the method comprises selecting said situations by a standardized testing using a VR system. Optionally or alternatively, said providing is at a patient's location of daily activities and during such activities.

There is provided in accordance with an exemplary embodiment of the invention a method of treating FOG, comprising:

automatically identifying an increased likelihood of an upcoming FOG event in a patient; and providing a cue to said patient in a manner which may prevent and/or assist in overcoming said FOG event.

There is provided in accordance with an exemplary embodiment of the invention a system for FOG assessment and/or training, comprising:

(a) a VR display system;

(b) a controller programmed to provide on said VR display system one or more scenes designed to encourage FOG.

In an exemplary embodiment of the invention, the system comprises one or more physiological and/or movement sensors which provide feedback to said controller and which said controller uses to vary a display in connection with modifying a FOG likelihood. Optionally or alternatively, said controller provides an obstacle for a subject to respond to. Optionally or alternatively, said controller provides a cognitive load for a subject to respond to. Optionally or alternatively, said controller provides an environmental feature for a subject to respond to. Optionally or alternatively, said controller provides a perceptual load for a subject to respond to.

There is provided in accordance with an exemplary embodiment of the invention a system for assisting with FOG, comprising:

(a) a sensor;

(b) an output;

(c) a controller configured to process a signal from said sensor to detect an increase in likelihood of FOG and generate a signal on said output in response thereto. Optionally, said system is designed to be worn and wherein said output signal is suitable to prevent and/or assist in overcoming FOG.

In an exemplary embodiment of the invention, said controller is programmed to providing a training in FOG avoidance to a subject.

In an exemplary embodiment of the invention, said sensor generates an indication of blood flow change in the brain.

In an exemplary embodiment of the invention, said sensor generates an indication of acceleration of a body part.

In an exemplary embodiment of the invention, said controller determines the existence of a sub-clinical FOG state.

There is provided in accordance with an exemplary embodiment of the invention a method of measuring gait characteristics of a subject, comprising:

collecting signals from at least one sensor making a physiological measurement of the subject; and processing said signal to detect a sub-clinical state of FOG.

In an exemplary embodiment of the invention, the method comprises calculating a future risk of FOG in said subject based, at least in part, on said detected state.

In an exemplary embodiment of the invention, said detected state is not visually detectable by observation of said subject.

There is provided in accordance with an exemplary embodiment of the invention a method of measuring gait characteristics a subject, comprising:

detecting a change in blood flow to a brain region in a subject at least planning locomotion; and determining a FOG or sub-clinical FOG state based, at least in part, on said detected change.

In an exemplary embodiment of the invention, said change comprises a reduction in blood flow to frontal lobes of said subject. Optionally or alternatively, said determining comprises also using acceleration data of at least one limb of said subject. Optionally or alternatively, said detecting comprises using an fNIRS sensor. Optionally or alternatively, said detecting comprises using an EEG sensor.

There is provided in accordance with an exemplary embodiment of the invention a method of quantifying FOG, comprising calculating a FOG Index (FI) based on a physiological measure that is combined with at least one background measure of FOG propensity. Optionally, said background measure comprises a reaction to an obstacle. Optionally or alternatively, said background measure comprises a cost of a cognitive load. Optionally or alternatively, said background measure comprises a cost of an environmental feature. Optionally or alternatively, said background measure comprises a cost of a perceptual load. Optionally or alternatively, said physiological measure includes an APA (anticipatory postural adjustment).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings and graphics. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 7 shows the raw acceleration signal and spectral density of the frequency band of gait of a patient (patient 4) over 10 seconds during the no-obstacle trial, in an example in accordance with an exemplary embodiment of the invention;

FIG. 14 is a table 1 showing FOG quantification and scoring, in accordance with an exemplary embodiment of the invention;

FIG. 15E is a table 2 showing patient characteristics as used for an example in accordance with some embodiments of the invention;

FIG. 16 is a table 3 showing measures of consistency of patients as used for an example in accordance with some embodiments of the invention;

FIG. 17 is a table 4 showing test parameters of patient 1, as used for an example in accordance with some embodiments of the invention;

FIG. 18 is a table 5 showing test parameters of patient 2, as used for an example in accordance with some embodiments of the invention;

FIG. 19 is a table 6 showing test parameters of patient 3, as used for an example in accordance with some embodiments of the invention; and FIG. 20 is a table 7 showing test parameters of patient 4, as used for an example in accordance with some embodiments of the invention.

DESCRIPTION OF SPECIFIC EMBODIMENTS OF THE INVENTION

Figure 1:
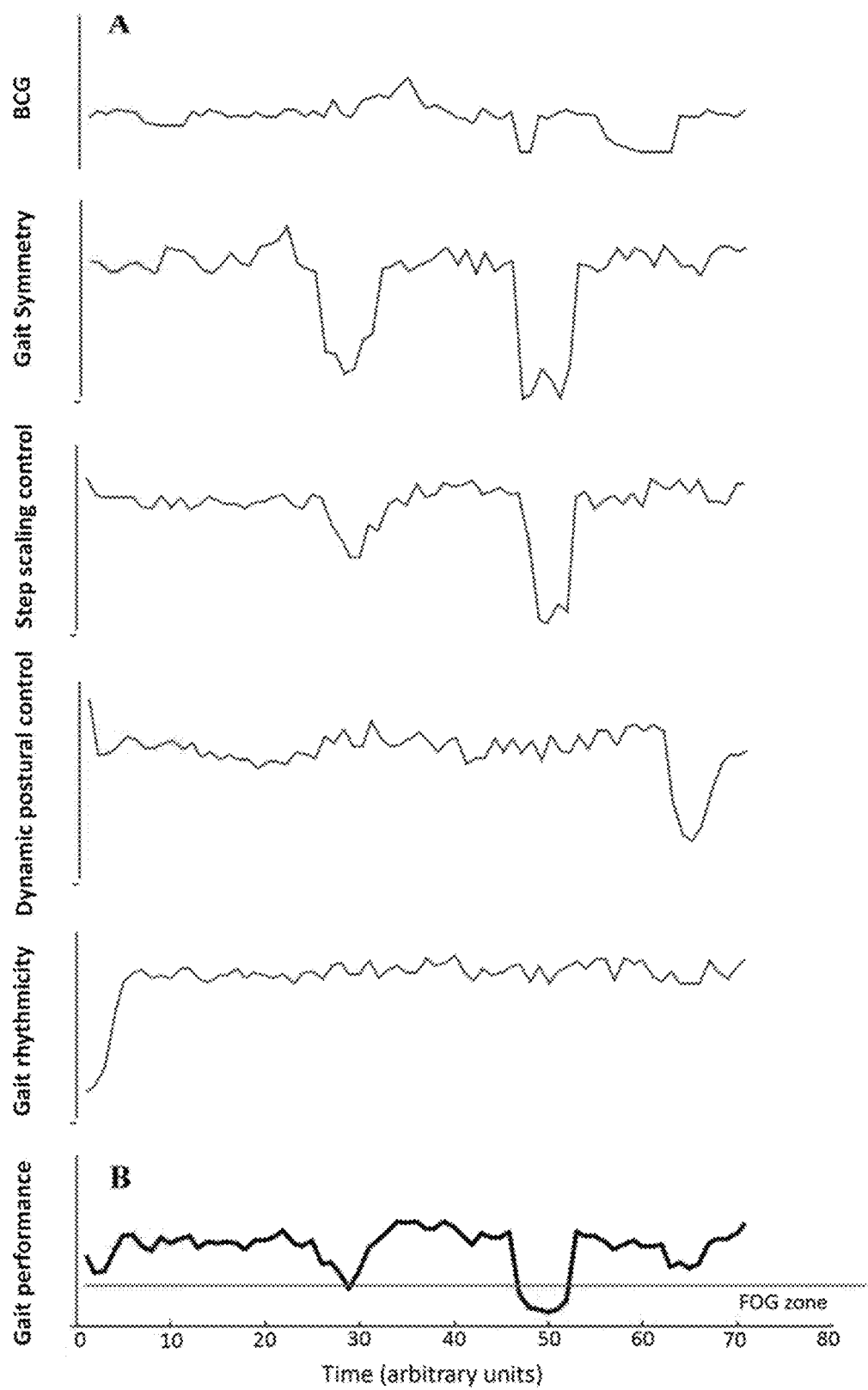
FIG. 1 is a set of graphs schematically showing freezing of gait and gait features deterioration, as used in accordance with some embodiments of the invention.

The present invention, in some embodiments thereof, is related to diagnosis and/or treatment of episodic gait disorders, for example freezing of gait (FOG), for example, by provoking freezing of gait and/or measuring changes in gait and/or cranial blood flow due to such provoking. Optionally or alternatively, measurements of gait are used to identify an increased risk for imminent FOG and preventive action is optionally taken.

Overview

In an exemplary embodiment of the invention, a system is provided which uses a novel modality that will expose patients to FOG-invoking situations, in a well-controlled and safe environment, quantify the severity and specific pattern of FOG for each person, and then optionally provide treatment according to these needs. Optionally, treatment will be based on allowing the patient to adapt, using implicit motor learning, and, eventually, more appropriately deal with the circumstances that would otherwise lead to FOG. While focusing on FOG, systems and methods as described herein may also be used for other gait disorders.

In an exemplary embodiment of the invention, what is provided is a FOG stress test based on physiological measures and to quantify these FOG episodes to assess its characteristics. In an exemplary embodiment of the invention, the stress test can be used to selectively stress various components of the patient's totality, to determine which and how much, each contributes to FOG. For example, a cognitive ability may be stress and/or a perceptual ability may be stressed. In an exemplary embodiment of the invention, the stress test can provoke a higher frequency of FOG (and/or pre-FOG) events (e.g., per step) than normally detected, for example, by a factor of 2, 10, 50, 100, 200, 100 or intermediate or larger factors.

In an exemplary embodiment of the invention, the system can provide one or both of identification of an on-going FOG event and/or predicting the occurrence of a visible manifestation of FOG. Optionally, these are provided even on a locomotion device, such as a treadmill, which provides cuing.

An aspect of some embodiments of the invention relates to systems and/or methods that integrate online locomotion stimulating and monitoring technologies, for, inter alia, diagnosing and/or treating FOG.

In an exemplary embodiment of the invention, such a system can automatically identify walking patterns of an individual; introduce controlled freezing provoking situations (e.g., as a 'freezing stress test'); and/or evaluate the response of the subject to the freezing stress test, optionally by providing a score and/or identifying the dominancy of subtypes of freezing. In particular, one or more of the following subtypes may be identified: 'start hesitation', 'turning hesitation', 'narrow passage freezing', 'open runway freezing' and 'reaching destination freezing'. In an exemplary embodiment of the invention, an orthogonal definition of sub-types relates to scope: short, long and sub-freezes, where sub freezes can be specific, for example, to any of the above situations, but not be visual and/or not functionally affect patient. In this context, a freezing episode that lasts less than 0.5 seconds, for example, may have only a minimal impact and may not be felt by the subject, maybe considered a sub-freeze. An episode of up to, for example, 3 seconds may be a short freeze and longer episodes may be long freezes. Other time thresholds may be used as well. In an exemplary embodiment of the invention, it is presumed that sub-freezes are pre-cursors of longer and more disabling freezing events.

In an exemplary embodiment of the invention, a repertoire of one or more treatments based on strategy learning suitable for the individual, related to the specific evaluation, are provided. For example, if the stress test reveals that the patient is prone to freezing specifically when he/she approaches a narrow passage, the virtual reality training program may include many scenarios and scenes in which the width of the path is manipulated. As another example, if the assessment reveals that the patient is especially prone to freezing when he or she is required to attend to another task while walking, then the training may include sessions designed to implicitly teach the patient to walk while dual tasking. For example, if the stress test reveals that the patient is prone to freezing when he/she is required to dual task and navigate around obstacles, these elements may be featured in the training program. In an exemplary embodiment of the invention, for example, via a gradual and tuned exposure to these freezing provoking elements, in a safe environment, the training may act like a vaccine, empowering the patient to, for example implicitly, learn to appropriately deal with these situations, sometimes by way of cognitive and/or motor compensation, for example, based on the application of motor learning principles.

In an exemplary embodiment of the invention, such a stress test is based on both of presentation of situations and measuring the effect of such stress on one or more physiological, motor, behavioral and/or cognitive measures. Exemplary types of stress that may encourage provocation of freezing include, for example: a) Stimulating challenge on bilateral coordination of gait by using split belt treadmill with 2 belts running in unequal velocities or requiring the left and right legs to act out of phase by providing obstacles b) increasing the frequency of stop and start of walking to provoke start hesitation freezing, c) imposing walking in reduced step length, to provoke freezing occurring when stride length is reduced, d) increase cognitive load and/or divert attention, e.g., by performing a simultaneous cognitive task while walking; the load optionally being increased when a pre-FOG or FOG situation is detected; this can be achieved, for example, by adding distracters into the VR scene, and/or increasing their intensity, level of detail, distraction ability and/or frequency, and/or by asking the patient to perform increasingly difficult tasks while walking in the VR scene, e.g., first count forward, then count backwards by is, then serial 3 subtractions, then serial 7 subtractions, e) introducing challenging walking tasks such as obstacle negotiation in limited time to create mental stress and/or f) forcing gait in changing pace conditions to impose gait dysrhythmicty that is associated with freezing. Levels of provocation can range, for example, from no provocation of one or more types to combining provocations from different types, thus potentially creating continuum scale of challenge.

In an exemplary embodiment of the invention, the frequency of provocation and/or overlap in time of provocations can be varied as well. The number of FOG episodes (level of success) and their duration may then serve as a measurable score for the level of freezing severity. For example, these parameters may be weighted based on the level and/or degree of provocation. For example, if someone experiences many freezing episodes even when there are no provocations, no cognitive loading and no distracters, these episodes will receive a relatively high weight. In contrast, if someone only has a few freezing episodes when he/she is exposed to the most challenging conditions of the stress test, the weight of these episodes in the scoring may be relatively small.

An aspect of some embodiments of the invention relates to measuring FOG susceptibility by providing controlled provocations. In an exemplary embodiment of the invention, accurate and/or quantitative diagnosis of FOG is provided. In an exemplary embodiment of the invention, adaptations and/or developments in mobility patterns with respect to FOG, are determined, based on physiological measures. Optionally or alternatively, the occurrence and/or frequency of occurrence and/or triggers for occurrence of FOG episodes among people who suffer from the symptom are at least estimated.

In an exemplary embodiment of the invention, a "FOG load" is defined per subject, which relates to how much a given situation (e.g., including triggers) increases a likelihood of a FOG episode and/or otherwise adversely affect gait.

An aspect of some embodiments of the invention relates to controllably placing of a subject in circumstances that provoke FOG, where the degree of provocation is measurable and adjustable. Optionally, this provides the ability to sensitively and/or accurately monitor changes in FOG over time and/or in response to treatments. Provocations can include for example one or more of the examples listed above and/or: a) Stimulating challenge on bilateral coordination of gait by using split belt treadmill with 2 belts running in unequal velocities b) increasing the frequency of stop and start of walking to provoke start hesitation freezing, c) imposing walking in reduced step length, to provoke freezing occurring when stride length is reduced, d) performing simultaneous cognitive task while walking to divert attention, e) introducing challenging walking task such as obstacle negotiation in limited time to create mental stress, and/or f) forcing gait in changing pace conditions to impose gait dysrhythmicty that is associated with freezing. Levels of provocation can range from no provocation of one or more types to combined provocations from different types, thus creating continuum scale of challenge. The number of FOG episodes and their duration, optionally in combination with the level and degree of provocation, may serve as a measurable score for the level of freezing severity.

It is a particular feature of some embodiments of the invention, that FOG situation are deliberately triggered so as to provide sufficient examples in a laboratory (or other) situation, for testing and/or treatment. Optionally, one or more near-FOG situations are caused, such situations optionally being identified by their effect on gait and/or cognitive behavior, e.g., one or more of bilateral coordination deteriorates, and/or gait rhythmicity, and/or gait asymmetry, and/or gait asymmetry, and/or performance in dual tasking conditions.

An aspect of some embodiments of the invention relates to a system and/or method for reducing propensity toward FOG via appropriate motor learning and/or exposure to FOG-invoking situations. Optionally, such situations are provided in a well-controlled environment that allows the patient to adapt, over time, and eventually to more appropriately deal with the circumstances that would otherwise lead to FOG. For example a patient who is particularly prone to 'start hesitation' type of freezing, will be exposed to many 'start walking' conditions, the system that monitors his/her behavior will identify if the provocation is indeed leading to FOG, and if yes, an external cuing will be used to teach the subject to avoid the episode. It is believed that intensive repetitions of such trainings will cause the nervous system to identify these near FOG situations and to generate the motor response that was generated during the training periods in a proactive manner, before FOG occurs. The results shown in FIGS. 12 and 13 support this possibility.

In an exemplary embodiment of the invention, a training program includes continuous measurement of patient status and thus allows, for example, adjusting a training program to address a patient's abilities and/or progress.

In an exemplary embodiment of the invention, training is provided during daily living conditions and/or at home. For example, a patient may be provoked into FOG, for example, after some warning, while carrying out an activity such as walking and turning, one of the more common provocations, in his house.

An aspect of some embodiments of the invention relates to a system and/or method for providing warning on an incipient FOG and/or ongoing event. Optionally, such a system is worn by a patient and/or is located in a place of activity, such as a home.

In an exemplary embodiment of the invention, such a system, in addition to or alternatively to providing warnings, provides signals or cues to help prevent and/or break out of a FOG situation. This could be in the form of vibratory or auditory cues or electrical stimulation to a limb or other part of the body.

In an exemplary embodiment of the invention, such a system, in addition to or alternatively to warnings and/or cuing, is used to provide a training program to maintain and reinforce training benefits during daily living conditions, outside of any laboratory based training sessions.

In some exemplary embodiments of the invention, a treatment system is provided. Using the information provided, for example, by the system, after a baseline assessment, the system can automatically (e.g., or manually by an operator or therapist) create individually-tailored training programs to train the motor system of the subject, for example, to adapt motor strategies that distance a subject from the physiological circumstances that lead to FOG (e.g., see FIG. 3). For example, if the evaluation highlights that a subject has mainly problems with gait asymmetry, the focus of the treatment will be on motor learning that will result in modifying the gait pattern to become more coordinated, optionally in part, via repeated and measured asymmetrical challenges (e.g., more obstacles on the left side than the ride side) In another example, If it is determined that adding a cognitive load is needed then it will use the VR simulation to provide training that is rich with cognitive stimulus tasks such as visual spatial processing, attention, planning and executive function. Gradual exposure to these challenges enables accommodation and allows the patient to learn how to grapple with these situation; over time, the challenges will become more difficult, and the learning can continue, for example, until it achieved the desired result, even in the more challenging conditions. The gradual process may allow the patient to slowly expand his/her capabilities, encourages engagement of the subject in the process, and minimizes discouragement and frustration; the end result is possibly a greater opportunity for motor learning. In alternative embodiments, a non-gradual approach is used.

An aspect of some embodiments of the invention relates to detection of sub-clinical FOG states and events, for example, events which are not amenable to identification by eye and/or events which the subject is not himself aware of.

In an exemplary embodiment of the invention, such sub-clinical states are identified, at least in part, based on a change in cerebral processing, for example, as evidenced by changes in blood flow to the brain, for example, as evidenced by flow of blood from frontal lobes (e.g., over a time of 0.3, 1, 3, 5, 10 seconds or intermediate or other lengths of time) and/or flow of blood to motor and/or pre-motor regions (e.g., for same times). Optionally or alternatively, sub-clinical states are detected based on motion analysis, for example subtle trembling (e.g., detected as increase in power in high frequencies) of a limb, even if there is no change in actual gait periodicity and/or length.

In an exemplary embodiment of the invention, a single walking event, for example, between 1 and 30 seconds long, or for example, between 3 and 10 seconds long is identifiable (e.g., based on system settings) as FOG, pre-FOG and/or sub-clinical FOG.

In an exemplary embodiment of the invention, risk for upcoming FOG events, e.g., in next hour, day, week, month, year and/or integer multiples thereof and/or intermediate periods is assessed based on the analysis. In an exemplary embodiment of the invention, such analysis and prediction may be provided even if no visible FOG events are detected, only sub-0-clinical events.

An aspect of some embodiments of the invention relates to detection of FOG, near-FOG and/or sub-clinical FOG events and/or classifying (e.g., automatically and/or manually) said detected gait abnormalities, based on changes in cerebral processing, for example, based on changes or indication of changes in flow. For example, reduced flow to the temporal lobes and/or increased flow to motor or pre-motor areas may indicate FOG of certain types. Increased flow to temporal lobes may indicate a cognitive difficulty in gait, for example, due to an obstacle. Increased flow to the frontal lobes may reflect an attempt at utilizing cognitive function and attention to compensate for impaired "motor" mechanisms.

Potential benefits of some embodiments of the invention include one or more of enabling accurate diagnosis of FOG propensity, while quantifying the severity of FOG and identifying the circumstances that most likely lead to FOG in the specific patient; providing treatment that will be personalized and tailored for the patient's needs; and time. For example, within 20 minutes (5 trials of 4 minute walks each), one can assess and diagnose FOG and quantify the gait and FOG features and therefore can assist with providing the most appropriate personalized care that will address the patients needs.

An aspect of some embodiments of the invention relates to a FOG propensity score based not only on number and/or duration of FOG events. In an exemplary embodiment of the invention, the score is based on sub-clinical events. Optionally or alternatively, the score is based on a reaction to environmental load. Optionally or alternatively, the score is based on a reaction to a cognitive load, for example, dual task and/or attention tasks. Optionally or alternatively, the score is based on a perceptual load (e.g., lighting conditions). Optionally or alternatively, the score is based on the response to an obstacle and/or specific obstacle properties. Optionally or alternatively, the score is based on one or more background gait qualities.

In an exemplary embodiment of the invention, the score depends on detection of APAs which may indicate a patient's preparation for a challenge and/or gait disorder.

In an exemplary embodiment of the invention, the score is a linear sum of considerations, each weighted, for example, according to patient characteristics, for example, based on a library of control subjects. Other forms of score formula may be used as well.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Some Example Classifications

Some embodiments of the invention are based on the realization that the pathophysiology of FOG may be distinct from that which leads to other parkinsonian symptoms. For example, no correlation was found between the frequency of FOG episodes and other motor symptoms of PD (e.g., rigidity, bradykinesia), while FOG frequency was inversely correlated with tremor severity. This underscores the fact that FOG is possibly a result of pathophysiology that has yet to be fully explained. FOG has received increasing recognition as a debilitating feature of PD. Several studies suggest that FOG affects between 20-60% of PD patients. Because mobility is so important to quality of life and functional independence, it is not surprising that gait disturbances and freezing in PD often lead to wheelchair use and nursing home admissions.

In an exemplary embodiment of the invention, the mechanism underlying a particular case of FOG is optionally determined. In an exemplary embodiment of the invention, the levels by which the subjects suffer from different subtypes of freezing are determined: in particular, one or more of 'start hesitation', 'turning hesitation', 'narrow passage freezing', 'open runway freezing' and/or 'reaching destination freezing'. Optionally, based on such determination, therapeutic and preventative measures for FOG are defined. In an exemplary embodiment of the invention, when a patient is diagnosed, the degree of susceptibility to each type of FOG is separately measured and a vector indicating the relative susceptibility optionally created.

In an exemplary embodiment of the invention, a system is provided which reveals distinct physiological processes that occur during walking prior to the appearance of FOG, and/or on identifying the relative and/or absolute role of a potential triggers, e.g., shifts of attention, that can exacerbate gait and cause FOG. Once these processes are identified and/or quantified, therapeutic measures can be designed and optionally tested in follow-up studies.

In one example, for a patient where bilateral coordination is a problem, interventions that focus on bilateral coordination may promote resiliency to FOG triggers.

In an exemplary embodiment of the invention, measurements of patients are used to provide information to add to the body of knowledge on the cognitive capacity in advanced PD during the "Off" state of the medication cycle and its role in gait and FOG. Optionally, this information is used for providing diagnosis and/or treatment for such conditions.

Several studies have examined the mechanisms that might underlie FOG. Unique but not uniform patterns of EMG were seen in patients with FOG just prior to freezing. In an exemplary embodiment of the invention, it is assumed that rhythmic contractions of leg muscles beyond a certain rate might contribute to FOG. In an exemplary embodiment of the invention, the timing of EMG activity of the tibialis anterior and gastrocnemius muscles is checked and if found to be abnormal may be considered a warning sign of imminent FOG in a subject.

In an exemplary embodiment of the invention, from a phenomenological perspective, one or more of the following features which may be found in FOG patients (especially secondary to PD) are measured and/or monitored, especially in response to various provocations: Impairments in step length scaling, reduced dynamic control of postural stability, increased gait asymmetry, poor bilateral coordination of gait and rhythmicity.

In an exemplary embodiment of the invention, a test includes uncoupled pedaling of a patient, which may indicate a relationship between bilateral coordination of gait (BCG) and FOG in PD. In such pedaling, using a stationary bicycle with the left pedal mechanically uncoupled from the right pedal, although the relative phase (between the legs) was locked at approximately 180 degrees in healthy elderly and some of the people with PD, PD patients who suffer from FOG (PD+FOG) exhibited relative phase drift monotonously from 0 to 360 degrees, or an irregularly modulated phase generation. The existence, amount and/or other parameters of such drift may be used as an indicator for FOG and especially for an imminent FOG episode, for example, in response to a provocation.

It is hypothesized that uneven control of "coupled oscillators" (meaning the paddling action of each leg serves as oscillator) may result in such disarrayed phase generation. Unlike in the case of uncoupled bicycle or in gait, the coordination of left-right cycling movements poses less challenge to the central nervous system (CNS) since the mechanical coupling between the pedals facilitates the anti-phased left-right pattern. The possibility that impaired cerebral control of bilateral coordination is associated with freezing, e.g., in a particular patient, can gain further support if left-right coordination of alternating hand movements is impaired in a particular subject as compared to patients who do not suffer from FOG (PD-FOG) and/or suffer other types of FOG.

Another indicator which is optionally used is radius of turn. In some types of FOG patients, a turning arc is increased as compared to PD-FOG, possibly reducing the level of asymmetry involved in the task and easing the burden on coordination. Such a change in angle and/or effect of angle on cognitive tasks, walking speed and/or other measurable signals, may be used to indicate a FOG burden, in accordance with some embodiments of the invention. In an exemplary embodiment of the invention, based on this test and others as indicated above, a multi-dimensional score will be generated. In one example, among the dimensions quantified are severity of 'start hesitation', 'turning hesitation', 'narrow passage freezing', 'open runway freezing' and 'reaching destination freezing', additional optional types of dimensions are the freezing response to provocation related to pathophysiologies associated with freezing, e.g., the freezing response to uncoordinated, and/or, asymmetric, and/or disrhythmic and/or scaled down and/or stability challenged gait. In addition, the magnitude of the freezing episode (both legs or one and duration) is optionally included in the score.

In an exemplary embodiment of the invention, the system uses a simulating-monitoring integration, optionally coupled using a closed loop. In an exemplary embodiment of the invention, the stimulating part is mainly composed from virtual reality (VR) technologies (e.g., a head mounted display or goggles or a projection on a considerable part of a room in which a subject is located or even a screen) that introduce freezing provoking situations, for example as part of an ongoing scene. Optionally or alternatively, non-VR technologies are used, for example, standing displays.

In an exemplary embodiment of the invention, sensors (e.g., mobility sensors, accelerometers), for example, mounted on the subject's body and/or off of the subject's body (e.g., cameras) will generate measurements. Optionally, the measurements are processed to predict and detect online (e.g., within 0-10 seconds from occurrence and/or with a lead time of between 360 and 3 seconds, for example, between 5 and 10 seconds lead time) the occurrence of FOG. Optionally or alternatively, processing is used to assess the gait pattern, quantify its qualities and/or feed this information to the VR system to adjust the virtual environment in which the subject is functioning. For example, adjustment can include providing a more provocative situations and/or different situations (e.g., using a table of potential FOG triggers and/or a training and/or a testing program).

Optionally or alternatively, miniaturized physiological sensors (e.g., ECG, skin conductance, fNIRS, EMG) or non-miniaturized and/or wireless and/or wired sensors are used to provide information about physical and/or mental stress.

In an exemplary embodiment of the invention, following a 'freezing stress test', optionally a standard set of situations and/or protocols, the system will be able to quantify properly the freezing burden and its individual characteristics for each subject.

Figure 3:
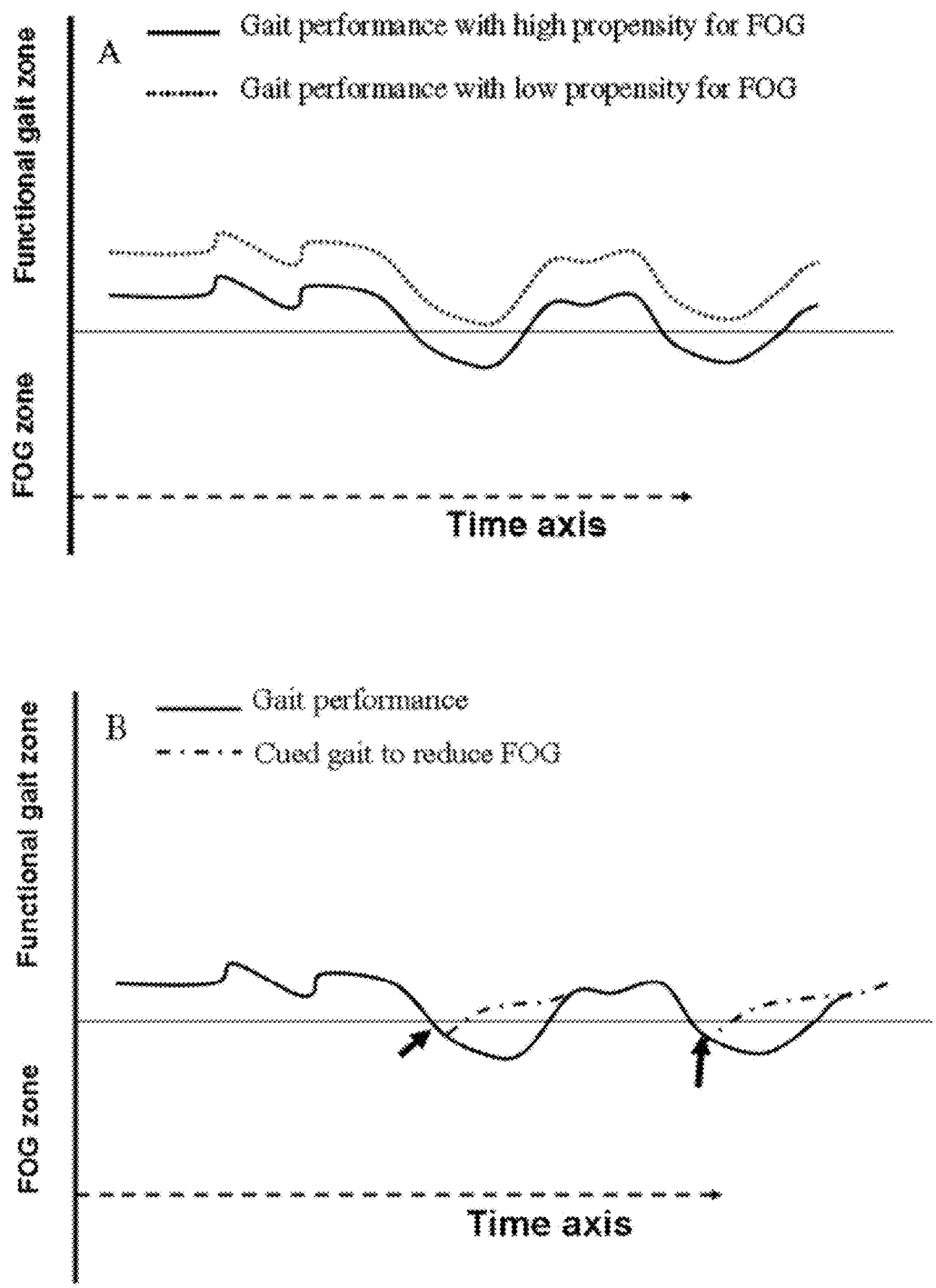
FIG. 3 is a set of charts illustrating intervening to improve overall gait performance and to reduce the FOG burden, in accordance with some embodiments of the invention.

In an exemplary embodiment of the invention, after diagnosing, the system (or a different system) will create individually-tailored training programs, for example, for training the motor system of the subject to adapt motor strategies that distance them from the physiological circumstances that lead to FOG. For example, if the evaluation highlights that a subject has significant problems with bilateral coordination (BCG being a measure of bilateral coordination of gait) and gait asymmetry, the focus of the treatment can be on motor learning that will result in modifying the gait pattern to become more coordinated. Likewise, if rhythm generation problems are identified, then the treatment may focus on rhythmicity improvements. These concepts are illustrated in FIG. 1. A potential to improve this and reduced the propensity to FOG is illustrated in FIG. 3.

FIG. 1, section A shows quality of performance of gait features associated with FOG (thin lines in top 5 traces) may vary over time (hypothetical data). Similarly the level of interaction between these gait features may vary with time and/or in response to different circumstances or provocations. BCG—Bilateral coordination of gait.

FIG. 1 section B illustrates how the combination of the performances of the individual gait features may dictate whether FOG will occur or whether functional walking will be maintained. If the overall performance deteriorates below a certain threshold (horizontal line), then gait freezes (FOG zone). Deterioration in the overall gait performance can be an expression of malfunction of single gait feature associated with FOG or of multiple features. In some cases, the deterioration of one gait feature can cause the deterioration of one or more gait features as portrayed in FIG. 1(A).

As another example, if a subject is prone to freezing due to poor gait performance when his/her attention is shifted to deal with simultaneous cognitive demands, then training strategies will be directed to assist in prioritizing between gait and mental tasks and/or to improve the simultaneous performance. In another example, if a subject is prone to freezing when dealing with challenges that cause him/her to be mentally stressed, then such situations will be introduced during training periods, for example by virtual reality technique, to improve the coping of the subject in such situations.

Exemplary Diagnosis System

In an exemplary embodiment of the invention, a sub-unit of a system composed of mobility and physiological sensors and from online feedback apparatus (e.g., earphones) will serve as a 'field assistive and monitoring device' that will be programmed by a 'parent controller' to online predict and detect the gait pattern, physiological conditions and FOG propensity and/or will provide corrective adjustments via the feedback apparatus to modify motor patterns. The information gathered by the 'field assistive and monitoring device' will optionally be fed to the 'parent controller' by remote access (e.g., internet, mobile phone) and adjustments to the assistive algorithms and to the feedback regime will be done based on all data gathered so far. The concept of 'assistive device' may be complementary, at least in part, to the 'training device'. While the latter addresses desirable sustainable modifications in the function of the motor system with regards to gait, an assistive device is to address gait difficulties in an ad-hoc fashion. Both, however are optionally based on the information gathered from the diagnostic element of the technology and may also be provided together in a single system.

Figure 2A:
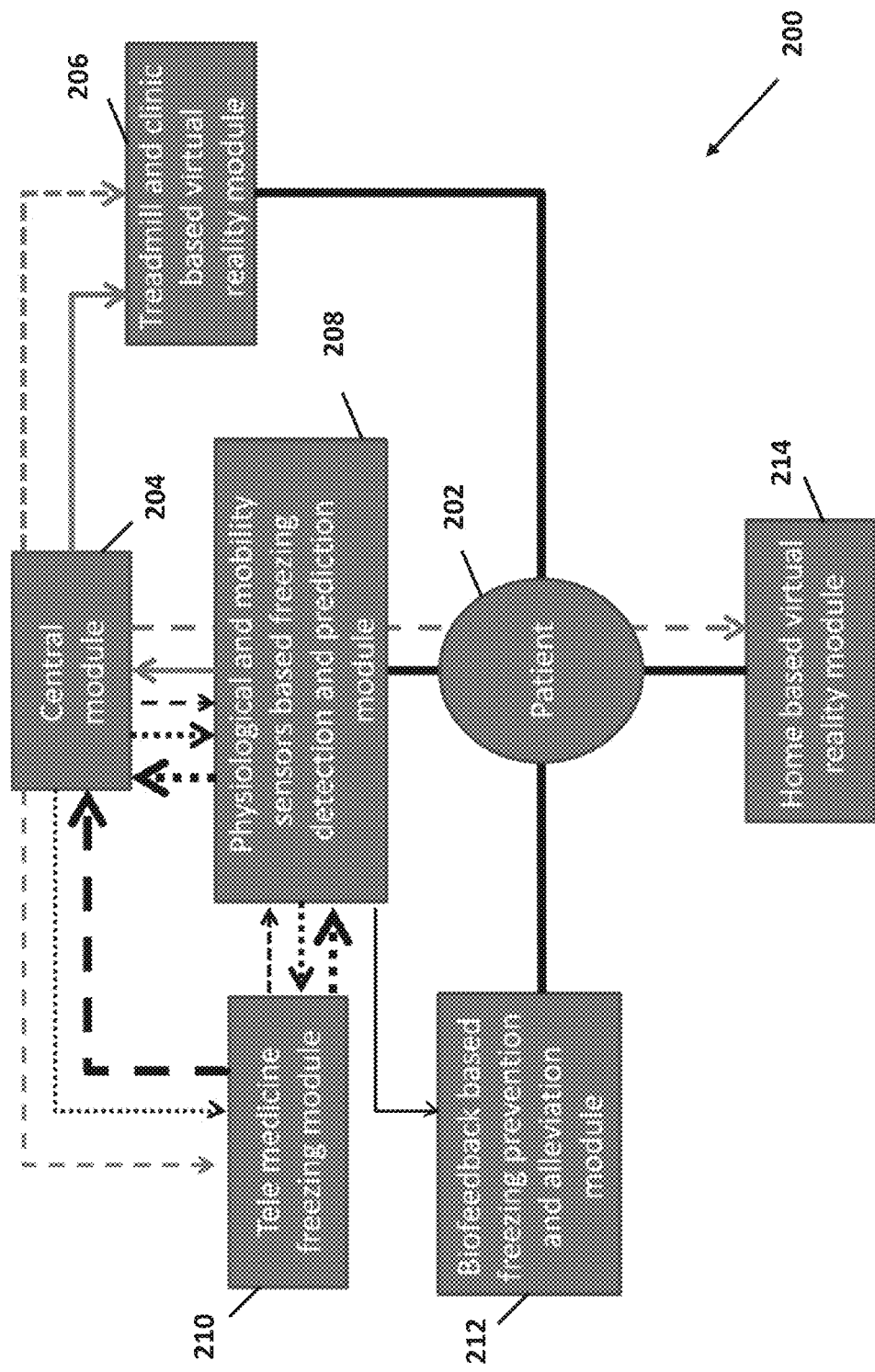
FIG. 2A is a schematic drawing of a FOG detection and/or treatment system in accordance with some embodiments of the invention.

FIG. 2A illustrates some potential modules of a system 200 for use on a patient 202, one or more of which modules may be provided (e.g., being optional), in accordance with an exemplary embodiment of the invention.

(a) Central module (CM) 204—a main controller of the system (e.g., a computer, smartphone or other processing device, optionally mobile), located locally or remotely relative to other parts of system and/or distributed as several spaced apart systems, which optionally has interface with additional modules, local and/or remote, with computational capabilities.

(b) Treadmill and clinic based virtual reality module (TCVRM) 206—placed in the clinic, but optionally at home or at a public location such as an old-age home or day care center and provides virtual reality protocols. Techniques of virtual reality can vary, for example portable goggles with virtual visual input or an LCD screen, for example. Optionally or alternatively, sound and vibratory feedback may be provided. Movement mechanism other than treadmills can be used, for example, bicycles or stepping in place.

(c) Physiological and mobility sensors based freezing detection and prediction module (PMFDPM) 208—will optionally be used to assess the level of freezing burden achieved in response to the freezing provoking protocol. Optionally, this module is based on body wearable sensors (e.g., accelerometers, heart rate sensors, sweat sensors and/or brain blood flow sensors) and/or from information gained by the cameras or movement sensors (e.g., Kinect), which are optionally included in the TCVRM (e.g., which may be used to determine subject motion).

(d) Tele medicine freezing module (TMFM) 210—enables communication between CM and modules that function outside the clinical site, for example, by internet and/or mobile phone infrastructure, in real time (e.g., within 10 or 3 seconds or less) and/or optionally by reports.

(e) Biofeedback based freezing prevention and alleviation module (BBPAM) 212—a sub-system that provides sensory input as a feedback to the evaluation of performance, for training or for assisting (i.e., wearable assistive mechanism) purposes. In an exemplary embodiment of the invention, this module when acting as an assistive device, will generate external cueing whenever the PMFDPM will detect or predict the occurrence of freezing, so the subject can utilize the sensory input to avoid freezing. For example, if the sensory signal includes rhythmic auditory stimulation the subject will pace, coordinate, and/or enlarge his steps to the rhythm. This module when acting as a trainer, can, for example, provide the sensory input only during training sessions during which the subject will be exposed to freezing provoking conditions, and the feedback generated by the module will be used to train the subjects to the correct response (e.g., pace, coordinate, and/or enlarge the steps), with the purpose that following the training these responses will become natural whenever the physiological conditions approach FOG episode. An example such sub-system is described in FIG. 2B, below.

(f) Home based virtual reality module (HBVRM) 214—optionally provides virtual reality protocols at home and/or other non-clinic settings. In some embodiments, a warning device is provided which is worn by a patient and/or located in his home, detects a potential FOG situation and helps the patient avoid and/or overcome such situation. Optionally, such a device includes at least one sensor, a processing unit and a stimulus generating unit. Optionally or alternatively, such a device is used for training during daily activities, e.g., to increase a subjects sensitivity to problematic situations and/or to intentionally provoke such situations (e.g., by encouraging rhythmic movements), when the patient is forewarned. In an exemplary embodiment of the invention, the HBVRM can communicate with CM (e.g., via the TMFM) to receive basic data regarding the clinical condition of the subject. Based on that, the HBVRM can optionally define the daily at-home training program and/or will evaluate progress. For example, based on the knowledge from the CM that a subject suffers from impaired bilateral coordination, the HBVRM (or other module) can produce training tasks that require improvement of coordination, by for example, instructions to turn in place, e.g., by displaying on the home computer screen and/or on the home TV set, VR settings that requires coordination. At any point during the training, the HBVRM can provoke semi stress test to identify the response of the subject to the training.

In FIG. 2A, solid black lines indicate the modules that are interfacing directly with the subject 202; grey and/or dashed lines and arrows—each set of arrows in a specific shading represent a potential scenario for the use of the invention.

In an exemplary embodiment of the invention, one or more of the following algorithms/methods are implemented in the system:

a. Stress test algorithm. In an exemplary embodiment of the invention, this algorithm will start routine loading (at the beginning no loading of freezing provocation triggers will be introduced) of the freezing burden on the tested subject covering some or all types of freezing: e.g., 'start hesitation', 'turning hesitation', 'narrow passage freezing', 'open runway freezing' and/or 'reaching destination freezing'. In response to this initial testing the freezing burden is optionally increased and/or decreased as needed in any of the subtypes mentioned, to identify what is the freezing propensity in each of the subtypes. Various physiological bracketing and search methods may be used. One or more of freezing incidences per freezing provocation, spontaneous freezing episodes, and durations of all invoked or spontaneous freezing episodes, may serve as measures for freezing burden, as well as the quantification of gait qualities associated with freezing, e.g., rhythmicity, symmetry, bilateral coordination, step scaling and dynamic postural control.

b. Freezing detection and prediction algorithm. For example, based on an algorithm known as K-Means, the system can process, in real-time, the sensor data to characterize the level of propensity of FOG at any given time. A short training session may be provided in which an operator will feed in timing of the actual FOG episodes occurrences, and these data will be used by the system to define the individual characteristics of the mobility, and/or physiological (e.g., skin conductance data) data associated with FOG. Another algorithm based on ratio between energies in different frequency domains (the 'freezing index algorithm') of the mobility signal may be used instead of or in parallel to the K-Means algorithm. A weighing algorithm may be used to determine the relative weight in FOG prediction and/or detection each of these algorithms. Optionally or alternatively, pattern matching, Hebian neural networks computational schemes and/or machine learning can be used by the PMFDPM to identify patterns and/or match and/or calculate responses. In another method, wavelet analysis is used to identify patterns relating to or indicating FOG of one type or more or in general.

c. Cadence calculating algorithm. Optionally, to provide a cueing signal at the appropriate rhythm, in real time, a cadence determining algorithm is optionally used (e.g., based on a spectral analysis of the movements). Based on the mobility signal the number of steps per unit time will be calculated and the thus the cadence. This algorithm is optionally implemented in the BBPAM.

d. Training difficulty and training specifications algorithm. In an exemplary embodiment of the invention, this is a self iterative algorithm that starts with a specific anti freezing training program, e.g., expose the subject in laboratory and/or at home to gait tasks that may invoke freezing and providing automated training instructions (e.g., vocal and/or external stimulation). Interweaved within the training sessions, there are optionally one or more test sessions that will sample gait and freezing performance, compare the results to the defined quantifiable goals of the training (e.g., also a priori loaded to the system), assess progress with respect to time from start of training, and/or make decisions as for how to continue the intervention, e.g., the intensity of training and/or the exposure to different subtypes of freezing. Standard training planning methods may be used.

Exemplary Usage

There are currently gaps in the ability to diagnose the FOG symptom. Quantification is not standardized and involves cumbersome settings that are suitable for research but not for routine clinical use. Current treatments have limited impact. In an exemplary embodiment of the invention, the proposed system and/or method, in some embodiments thereof, may solve the problems of objective and/or quantifiable assessment of the FOG symptom. The second problem associated with the FOG symptom is that treatments are not effective due, in part, to the variable nature of the appearance of the symptom. In some embodiments, this problem is addressed by the system being adjustable based on the current physiological measures, and thus allows flexible training and/or assistive components. The unpredictable nature of the occurrence of the FOG episodes poses a problem related to the ability to avoid an episode alltogether, and/or to prepare for potential consequence of an episode (e.g., fall). In an exemplary embodiment of the invention, there is provided predictability of FOG episodes and/or pre-episode warning so that the approaching episode can be avoided.

Some exemplary usage prophetic scenarios are now described.

Scenario 1: Freezing of gait stress test (designated by dashed grey arrows in FIG. 2A)—central module (CM) will command a Treadmill and clinic based Virtual reality Module (TCVRM) in order to accompany locomotion while being immersed in 'reality' that is likely to provoke freezing of gait episodes (recall FIG. 1, that situations with challenging coordination, e.g., turning, and challenging stability, rhythmicty and/or reducing step length, may be likely to shift the subject into the freezing zone). Provocation of reduced step length can be achieved by, for example, by lowering the belt velocity in the treadmill, and/or providing visual cues, e.g., projecting lines on the floor, indicating the size of the required step length and/or by using virtual obstacles that require a large or small step over. The subject will achieve locomotion by walking on a treadmill or walking within a room. The subject will be immersed into the dictated VR by means of screens or special VR goggles. A physiological and mobility sensors based freezing detection and prediction module (PMFDPM) is optionally used to assess the level of freezing burden achieved in response to the freezing provoking protocol. This module may be based, for example, on body wearable sensors (e.g., accelerometers or brain sensors) and/or use from information gained by the TCVRM cameras. Optionally, the PMFDPM will determine the level of FOG burden achieved by the protocol. Optionally, the output of the PMFDPM will be fed into the CM which in turn will modify the protocol according to preset criteria. At the finish of several iterations one or more of the following may be achieved: 1) A clinical FOG score, for example, the number of freezing episodes occurring per provocation of freezing, number of spontaneous freezing episodes, and the duration of the freezing episodes; 2) An individual FOG profile, i.e., which situations are related to what level of propensity for freezing. For example, a profile may include calculations of the gait features associated with FOG, e.g., are deteriorating prior to each occurrence, e.g., rhythmicity, symmetry, bilateral coordination, step scaling and/or dynamic postural control.

Scenario 2: Prognostic daily monitoring of the freezing of gait symptom (designated by dashed black arrows in FIG. 2A). Scenario 2a—passive clinical data collection: The CM will embed the information about the FOG profile of an individual to the computational unit within the PMFDPM. The subject will perform his/her daily living carrying the PMFDPM (e.g., see FIG. 2B). The computational unit, based on the individual FOG profile will assess the level of FOG burden, and in addition will assess the performance of the gait features associated with FOG. This will provide a comprehensive picture about the clinical FOG conditions throughout the day, including, optionally, in response to interfering factors such as medication consumption or interventions. This information is optionally fed back to the CM via a tele medicine freezing module (TMFM) which can utilize, for example, internet or mobile phone infrastructure to pass clinical evaluations to the CM for the record and use of the health professionals treating the subject. Optionally, data can be also transferred by connecting directly the PMFDPM with the CM (rectangle shaped dashed black arrows for both options). Scenario 2b—active data collection: in addition to what is detailed in the passive clinical data collection, the CM and TMFM can be used to instruct the subject to perform short dictated locomotion protocol while the PMFDPM is analyzing the responses and transferring the information to the CM (via the TMFM). Optional tuning of on line detection and prediction parameters of FOG is optionally done from the CM to the PMFDPM (lower most rectangle shaped dashed black line).

Scenario 3: Intervention type I: Biofeedback based daily living assistive therapy to prevent freezing of gait (designated by thin black arrows in FIG. 2A). CM, for example, directly to the PMFDPM, or indirectly via the TMFM, provides parameters for computational algorithm working in real time for detecting and predicting the occurrence of freezing episode. This loading is done in a preparatory stage and designated in dashed lines in the figure the sensors are used to predict a FOG episode and the information from the sensors are sent to the control unit. Once such an episode is predicted or detected the PMFDPM provides a signal to biofeedback based freezing prevention and alleviation module (BBPAM), which in turn provides sensory feedback (e.g., auditory) to the subject, who utilizes this cueing to avoid or shorten the freezing episode. In this sense this is a closed loop module that can provide a biofeedback alarm to the patient even before a FOG occurs to alert him to change their pattern of movement and utilize movement strategies to avoid the occurrence. The system could also provide a feedback (e.g., a different sound) when a FOG has already occurred. This signal may be used as a cue to allow for the patient to recover from the FOG and continue walking.

A variety of types of feedback may be used, for example, based on the responsiveness of the subject. For example, rhythmic auditory stimulation helps the subject to pace, coordinate and scale his/her stepping and thus avoid stopping and/or shortening. Similarly, tactile stimulation may be used. Another possibility is vocal warning (similar to those used in Global Positioning Systems) and/or tactile vibrations in the foot, and/or pattern projection on the floor, for facilitating gait.

As mentioned above, a freezing detection and/or prediction algorithm can use several approaches, for example an algorithm known as K-Means, will process, in real-time, the incoming sensors data to characterize the level of propensity of FOG at any given time. Optionally, a short training session is used in which an operator will feed in timing of the actual FOG episodes occurrences, and these data will be used by the system to define the individual characteristics of the mobility, and/or physiological (e.g., skin conductance data) data associated with FOG. Another algorithm based on ratio between energies in different frequency domains (the 'freezing index algorithm') of the mobility signal may be used in parallel to the K-Means algorithm. A third algorithm may weigh what is the relative weight in FOG prediction and/or detection of each of these algorithms. Optionally or alternatively, one or more of pattern matching, Hebian neural networks computational schemes and machine learning may be implemented in the PMFDPM.

Scenario 4: Intervention type II: Biofeedback-based motor learning to ameliorate freezing of gait (designated by the thin black arrows in FIG. 2A. CM, directly to the PMFDPM, or indirectly via the TMFM, provides parameters for computational algorithm working in real time for detecting and/or predicting the occurrence of freezing episode. This loading is optionally done in a preparatory stage and designated with thin black dashed lines in the figure. This information is optionally utilized to run physiotherapy intervention program.

For this intervention, the gait pattern is optionally monitored continuously by the PMFDPM and the risk of an approaching FOG episode may be assessed in real-time based on the loaded algorithm. For example, patients may be challenged to walk at home or in the physiotherapy clinic, in situations that typically cause FOG (e.g., turns, tight circles, e.g., personalized for that patient). In the clinics the TCVRM will also be used for this purpose. At home conditions, a home based virtual reality module (HBVRM) is optionally used also for this purpose. Both the TCVRM and HBVRM are optionally programmed by the CM, which will optionally base its programming on feedback from the PMFDPM. When the gait patterns starts to deteriorate towards FOG, external cueing is optionally invoked by the BBPAM to restore a more normal gait pattern. This concept is illustrated in FIG. 3, and may be used in other embodiments described herein, as well. Desirably, after intensive such intervention the central nervous system will learn to automatically avert FOG (even without external cueing), and will maintain this capability by long term retention.

FIG. 3 section A illustrates improving gait performance in general, for example, by maintaining a sustained effective therapeutic effect on multiple gait features associated with FOG (recall FIG. 1), which is a target for therapy that will likely reduce the FOG burden. In general, one way of reducing the likelihood of FOG is to move the overall gait performance further away from the 'failure' threshold (horizontal line separating the 'functional zone' from the 'FOG zone'). FIG. 3 section B illustrates online intervention which may reduce the duration of FOG episodes using an assistive device format (scenario 3 type I) or an intensive training format (scenario 4 type II). The black arrows reflect two instances where FOG might normally occur when during daily living in a subject prone to freezing. A biofeedback device is optionally used to provide external sensorial cue to prevent the 'sinking' into the FOG zone, namely gait performance so deteriorated that functional gait is no longer possible. As mentioned above, a variety of types of feedback may be used based on the responsiveness of the subject. For example, rhythmic auditory stimulation helps the subject to pace, coordinate and scale his/her stepping and thus avoiding and/or shortening. Optionally or alternatively, rhythmic/periodic tactile stimulation may be used for such a result. Another possibility is vocal warning (e.g., similar to those used in Global Positioning Systems) and/or tactile vibrations in the foot, and/or pattern projection on the floor, all of which may be effective in facilitating gait under various conditions. For example, methods as described in any of the following are optionally used:

Lim I, van Wegen E, de Goede C, Deutekom M, Nieuwboer A, Willems A et al. "Effects of external rhythmical cueing on gait in patients with Parkinson's disease: a systematic review". Clin. Rehabil. 2005; 19(7):695-713.

J M Hausdorff, J Lowenthal, T Herman, L Gruendlinger, C Peretz, N Giladi. "Rhythmic auditory stimulation modulates gait variability in Parkinson's disease". Eur J Neurosci. 2007: 26:2369-2375.

S. Frenkel-Toledo, N. Giladi, C. Peretz T. Herman, L. Gruendlinger, J. M. Hausdorff. "Treadmill walking as a pacemaker to improve gait rhythm and stability in Parkinson's disease". Mov Disord 2005; 20:1109-1114.

T. Rubenstein, N. Giladi, J. M. Hausdorff. "The power of cueing circumvent dopamine deficits: A brief review of physical therapy treatment of gait disturbances in Parkinson's disease". Mov Disord, Vol. 17, pp. 1148-1160, 2002.

"Targeting dopa-sensitive and dopa-resistant gait dysfunction in Parkinson's disease: selective responses to internal and external cues". Rochester L, Baker K, Nieuwboer A, Burn D. Mov Disord. 2011 Feb. 15; 26(3):430-5. doi: 10.1002/mds.23450. Epub 2010 Dec. 13.

In an exemplary embodiment of the invention, when various treatments and/or cues are available, different ones may be tested on a patient and whichever treatment and/or cue performs best, is selected for treating the patient.

Figure 2B:
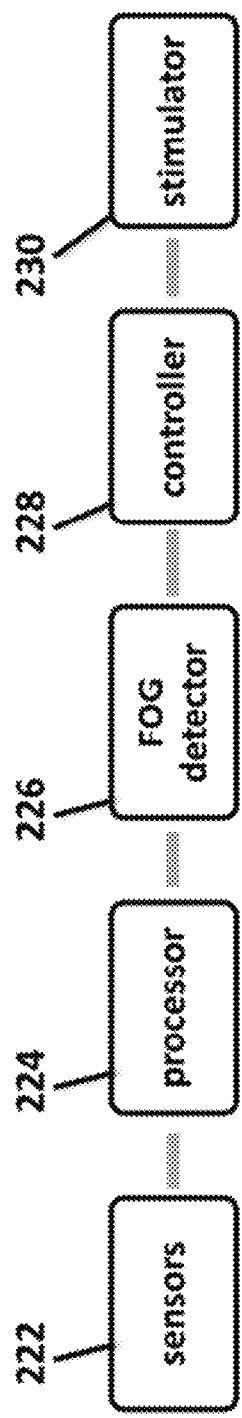
FIG. 2B is a schematic drawing of a FOG detection and/or treatment unit in accordance with some embodiments of the invention.

FIG. 2B is a schematic block diagram of a patient device 220, for example, suitable for implantation or wearing while ambulatory. Optionally, at least part of the functionality of device 220, for example processing, communication and/or acceleration measurement, is provided by a cellular telephone and/or by a sensor unit in wireless communication (e.g., Bluetooth) with the cellular telephone.

In an exemplary embodiment of the invention, device 220 includes one or more sensors, for example, as described herein, whose output is processed by a processor 224. A FOG (or other gait abnormality) detector, for example, embodied as one or more software modules executed by the processor, may detect, for example, expected or on-going FOG, sub-clinical FOG and/or pre-FOG states. In response, processor 224 may instruct controller 228 to cause one or more stimulators 230 (e.g., sound or vibration output devices) to stimulate the patient to overcome and/or prevent and/or otherwise ameliorate the FOG. After sensing that a freezing event is approaching, the sensor could alter the gait rhythm, suggest that the person speed up or slow, or even suggest that he/she sit down. This could be achieved via, for example, an electrical, auditory (sound and/or speech) and/or vibratory stimulus. In an exemplary embodiment of the invention, device is a light weight wearable sensor that will be worn by the subject at all times. The location of body attachment may depending on a patient's preferred stimulus; for example if the patient prefers an auditory stimulus then the device may be worn on a belt (e.g., include a clip) with an attached ear piece, if the patient prefers tactile stimulus, he can wear the device on the shin of his leg or in a necklace or bracelet. Optionally, the device is in two or more parts, communicating wirelessly and/or by wire, for example, one part being a sensor and optionally a processor and another part being a stimulator and optionally a processor.

In an exemplary embodiment of the invention, an implant provides a signal to an external component to cue the subject. Optionally, the implant also applies a treatment, for example, electrical stimulation (e.g., DBS). Detection and/or prediction of a gait abnormality is optionally provided by the implant, optionally using internal and/or using external sensors.

Anticipatory Postural Adjustment

In an exemplary embodiment of the invention, it is expected that a subject makes anticipatory postural adjustments (APAs), for example, changes in center of gravity (COG) and center of pressure (COP). Optionally, such APAs are detected, for example, using cameras and/or movement sensors and used, for example instead of or in addition to other physiological measures, to predict and/or identify gait abnormalities such as FOG.

In an exemplary embodiment of the invention, an APA is measured by quantifying the COP and/or by measures of trunk movements using accelerometers and/or gyroscopes carried on the belt or other positions that allow for estimation of the COP and/or COG. By challenging the subject in the VR system, it may be possible to detect early, mild and/or subclinical APA disturbances which may also optionally be used as markers for FOG. As noted herein, early detection allows to implement an early and potentially protective interventional approach to delay, reduce and/or prevent FOG and/or other functional disorders.

In an exemplary embodiment of the invention, APA detection is used for driving a cueing system for treatment of FOG and/or other gait disorders.

In an exemplary embodiment of the invention, APA detection is used as a marker for the usefulness of interventional programs with drugs, deep brain stimulation or physical rehabilitation methods.

In an exemplary embodiment of the invention, APAs are used to predict FOG, for example, before turns, when starting to walk and/or even during "open runway", usual walking.

In an exemplary embodiment of the invention, APAs are used as a target of training, for example, after training, larger APAs may be expected for some patients.

In an exemplary embodiment of the invention, APAs are used to diagnose a patient, for example, by seeing if and how APAs change and/or are delayed as a function of the type or other parameter of challenge used.

In an exemplary embodiment of the invention, VR simulations are modified in real-time to cause a desired APA (e.g., a certain COP). Optionally, the simulation is modified (e.g., various scenarios tried, intensity changed) until a desired APA is detected and/or failure is decided.

The abstract of Exp Neurol. 2009 February; 215(2):334-41. Knee trembling during freezing of gait represents multiple anticipatory postural adjustments. Jacobs J V, Nutt J G, Carlson-Kuhta P, Stephens M, Horak F B reads as follows: Freezing of gait (FoG) is an episodic, brief inability to step that delays gait initiation or interrupts ongoing gait. FoG is often associated with an alternating shaking of the knees, clinically referred to as knee trembling or trembling in place. The pathophysiology of FoG and of the concomitant trembling knees is unknown; impaired postural adjustment in preparation for stepping is one hypothesis. We examined anticipatory postural adjustments (APAs) prior to protective steps induced by a forward loss of balance in 10 Parkinson's disease (PD) subjects with marked FoG and in 10 control subjects. The amplitude and timing of the APAs were determined from changes in the vertical ground-reaction forces recorded by a force plate under each foot and were confirmed by electromyographic recordings of bilateral medial gastrocnemius, tibialis anterior and tensor fascia latae muscles. Protective steps were accomplished with a single APA followed by a step for control subjects, whereas PD subjects frequently exhibited multiple, alternating APAs coexistent with the knee trembling commonly observed during FoG as well as delayed, inadequate or no stepping. These multiple APAs were not delayed in onset and were of similar or larger amplitude than the single APAs exhibited by the control subjects. These observations suggest that multiple APAs produce the knee trembling commonly associated with FoG and that FoG associated with a forward loss of balance is caused by an inability to couple a normal APA to the stepping motor pattern.

In an exemplary embodiment of the invention, APAs are measured using a force platform and/or using center-of-pressure dynamics (e.g., force sensitive insoles or the accelerometers described above, which can reflect movement of the body's center-of-mass, which will reflect also the APA).

The inventors have also discovered that, based on a study 29 patients with Parkinson's disease (PD), freezing of gait episodes during turns are marked by multiple failed postural adjustments. These postural adjustments are typically seen as Anticipatory Postural Adjustment at gait initiation (e.g., before the person starts to walk). However, using measures of Center of Pressure (COP) Dynamics, they can also be quantified during turning and/or during straight line walking.

The obstacles placed in front of the subject generally also require a form of an APA (e.g., shifting of the center of gravity from one foot to the other to allow for sufficient clearance of the virtual obstacle). By challenging the subjects with these virtual obstacles (e.g., of different lengths and/or heights), the APAs/COP in response (e.g., before and/or during) can be measured. Possibly, in a healthy subject, the APA size will be related to the size/height of the obstacle. Optionally or alternatively, if/how these APAs change during FOG is measured. This can give another measure of FOG pre-disposition and possibly further enhance the ability to grade FOG severity, to predict, and/or to measure the response therapy.

In an exemplary embodiment of the invention, APAs are treated as are other measures, such as BCG. For example, APA is included as one of the weighted features in the scoring for FOG.

It is noted that in some embodiments, the APAs are measured on the ground (e.g., if patient is walking on ground towards a very large screen and/or wearing goggles) and in other embodiments APAs are measured on motion devices, such as treadmills and/or bicycles.

In an example of on ground VR display, a patient follows a standard lab course, such s walking along a corridor, and goggles are used to inject obstacles into the course and/or provide other loads as described herein.

Exemplary Methods

Figure 2C:
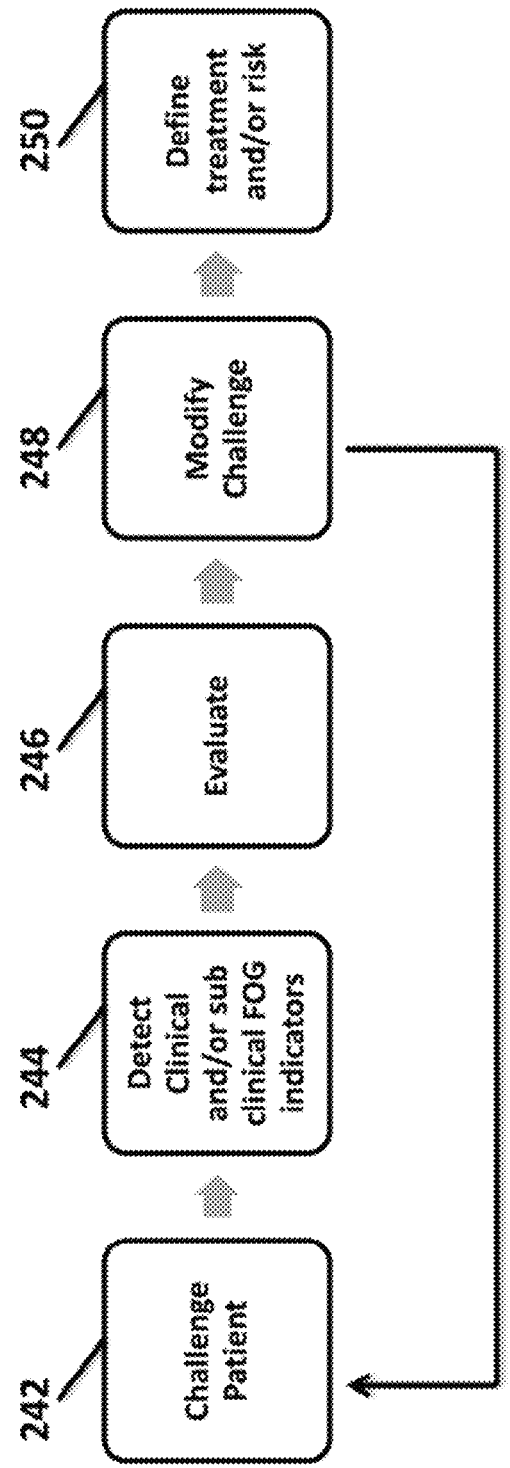
FIG. 2C is a flowchart of a method of diagnosing a FOG status of a patient in accordance with some exemplary embodiments of the invention.

FIG. 2C is a schematic flowchart 240 of a method of applying the methods described herein, in accordance with some embodiments of the invention.

At 242 a patient is challenged, for example based on the methods as described herein and/or based on a previous diagnosis.

At 244, one or more clinical and/or sub-clinical indications of manifestations of FOG are detected, or, alternatively, not detected.

At 246, the indications are evaluated, for example, by comparing to a table of standardized results.

At 248 the challenges are optionally modified, for example, to ensure a sufficient amount and/or quality of data is collected and/or to collect data about different types and/or sub-types of gait disorders. Challenging 242 is optionally repeated.

At 250, a treatment plan and/or a risk is optionally determined, based on the above evaluation(s).

Figure 2D:
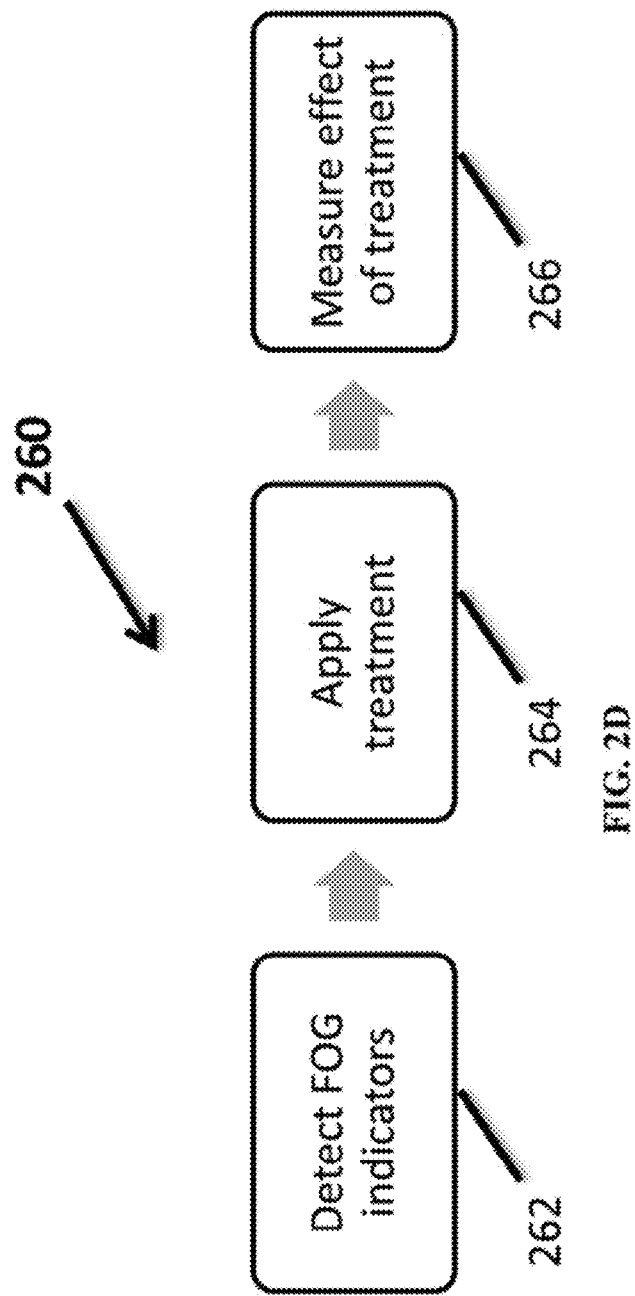
FIG. 2D is a flowchart of a method of treating a FOG disorder and/or event of a patient in accordance with some exemplary embodiments of the invention.

FIG. 2D is a schematic flowchart 260 of a method of treatment, optionally carried out by one or more of the devices described herein or manually, in accordance with an exemplary embodiment of the invention.

At 262, one or more FOG indicators are detected, for example, using accelerometers or other motion detectors or using a fNIRS sensor or other sensor to detect indications correlated with changes in blood flow to the brain.

In an exemplary embodiment of the invention, EEG or other means are used instead of or in addition to fNIRS to assess changes in cerebral activity. A potential advantage of using both EEG and fNIRS is that EEG has better temporal resolution and fNIRS has better spatial resolution.

In an exemplary embodiment of the invention, EEG can be used to measure brain electrical activity at rest and/or to measure (e.g., after filtering) brain activity during actions such as walking in the whole brain or in specific regions. Optionally, EEG is used to detect minimal changes in brain activity secondary to focal activation and/or depression of neuronal discharge. Based on the observations of decreased blood flow to the frontal lobe during FOG, it is expected that there will be focal frontal slowing or as called in EEG terms, theta or delta activity over the frontal lobe. Abnormal EEG activity can also be characterized by hyper or hypo synchronization of brain electrical activity in a specific area. EEG activity has been shown to be able to detect not just the movement potential but also the preparatory potential that comes before the actual movement is executed, which may support the use of EEG for prediction and detection of an actual event.

In an exemplary embodiment of the invention, continuous scalp EEG monitoring during walking, for example, by the Oxford ambulatory EEG monitoring system, is used to differentiate between normal stepping and FOG or pre-FOG state by change in background EEG activity over the frontal lobe bilaterally. In an exemplary embodiment of the invention, in the 1-3 seconds prior to the FOG itself and/or during the actual freezing episode, slowing of the background activity will be detected by automated frequency analysis system which is already present in the Oxford system. The system will be able to learn (e.g., using machine learning methods as known in the art) the normal locomotion of the subject treated and recognize the FOG as a significant change from the regular background. Similar detection may be applied for falls and/or other gait abnormalities.

In an exemplary embodiment of the invention, EEG measurement is used to specifically detect increase or decrease of activity in frontal lobes and/or motor regions, for example, based on changes in intensity (e.g., at certain frequency bands).

A potential advantage of EEG is its integration into an ambulatory and/or implanted device.

At 264 a treatment is applied, for example, cueing, as described above, or TMS stimulation, in response to the detection. In an exemplary embodiment of the invention, the application is within 0.1, 0.5, 1, 5, 10 or intermediate or greater number of seconds. Optionally, the treatment is timed to the predicted onset of the gait disorder, rather than to its prediction and/or detection time.

At 266 the effect of treatment is measured, for example, over a period of 1, 10, 100, 100 or intermediate or greater number of seconds. In response, the treatment and/or treatment parameters are changed. Optionally, the system learns which treatment is more effective for which set of measured indication values. For example, if asymmetry or poor rhythmicity or narrow passageways are frequent causes of the FOG in this patient, the training program may be adjusted to teach the patient to deal with this provocations.

In an exemplary embodiment of the invention, TMS (Trans Cranial Magnetic Stimulation) and/or other interventional means, such as biofeedback, is used to modify cerebral activity and/or blood flow in the brain. In an exemplary embodiment of the invention, when a decrease in blood flow to a frontal region is detected, TMS is applied (e.g., to the frontal lobe) to increase this flow. This may allow executive function to assist in overcoming FOG, reduce the likelihood that FOG or other gait abnormalities will occur.

In an exemplary embodiment of the invention, when an increase in blood flow to a motor region is discovered (e.g., by an fNIRS sensor), TMS may be applied to the frontal regions, for example, to further increase blood flow, for example, in patients in need thereof.

In an exemplary embodiment of the invention, the VR system will be used to synchronize the detecting and stimulating systems, fine tuning the frequency and strength of the TMS signal and/or for teaching and practicing the whole detecting-stimulating system with the patient before sending him home. Optionally or alternatively, the system is used to determine if such treatment can be assistive (e.g., by synchronizing TMS application with challenges, possibly with a delay there between).

Optionally or alternatively, TMS is applied based on predicted detection of FOG or other gait abnormality, additionally or alternatively to detection of cerebral changes, optionally in anticipation thereof.

In an exemplary embodiment of the invention, after treatment by TMS and/or training, it may be expected to find changes in blood flow patterns during pre-FOG and/or FOG states (or other gait abnormalities), even if there is no or small improvement in the abnormality. Optionally, this is used as a target for training. Desirably, the frequency of events will be reduced and/or difficulty in provoking such increased. In other embodiments, TMS is integrated into a worn device, such as a cap and the patient can be "treated" when needed.

Exemplary Implementation and Experiments

In this section, various practical implementations as a system are described, including results from utilizing these implementations for diagnosing and/or treating people in accordance with some embodiments of the invention. It should be noted that the teachings herein are not limited to the specific system tested and may be used with other embodiments of the invention.

Exemplary System Architecture

In this exemplary embodiment, the system is designed to integrate both online locomotion stimulating techniques and monitoring technologies. The system automatically identifies the walking patterns of the individual, introduces freezing provoking situations (a kind of 'freezing stress test') in a controlled environment, quantifies and characterizes the freezing episode, and assesses the best repertoire of treatment suitable for the individual.

Figure 4A:
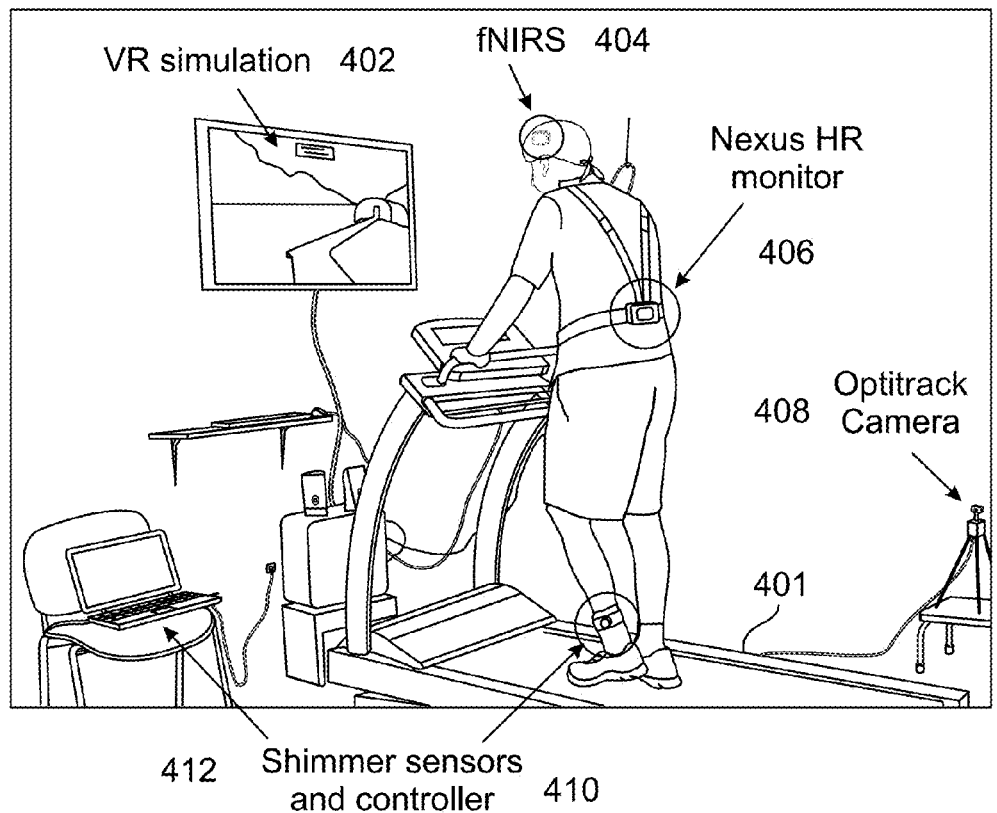
FIG. 4A is an image showing an implementation set up in accordance with some embodiments of the invention.

FIG. 4A is a picture of such a system. This 'all in one' system is comprised of a treadmill 401, a virtual reality (VR) simulation 402 (here shown on a display, rather than, as an alternative, goggles), and accelerometers 410. The patients walk on treadmill 401 while immersed in the VR environment 402. Small passive markers are optionally attached to the patient's shoes or other parts of the patient's body or clothing, optionally using a harness, and act as the interface or gateway to the VR system (e.g., via a camera 408 or other position and/or orientation tracking system). In an alternative embodiment a marker-less tracking system is used. Using two optitrack cameras 410, the movements of the feet are detected and inserted into the VR simulation using an avatar (e.g., as shoes on the screen) that accurately reflect the movement of the feet in reaction to the VR scene. Optionally, the patient wears a safety harness. Optionally or alternatively, the patient wears a heart rate monitor 406. Optionally, the subject wears fNIRS sensors 404 (e.g. covered by a head cap) and/or ECG sensors. These cerebral sensors are optionally used for physiologic monitoring and/or validation purposes. A controller 412 is optionally used to control and/or read sensors 410 and/or provide input to VR environment 402.

Figure 4B:
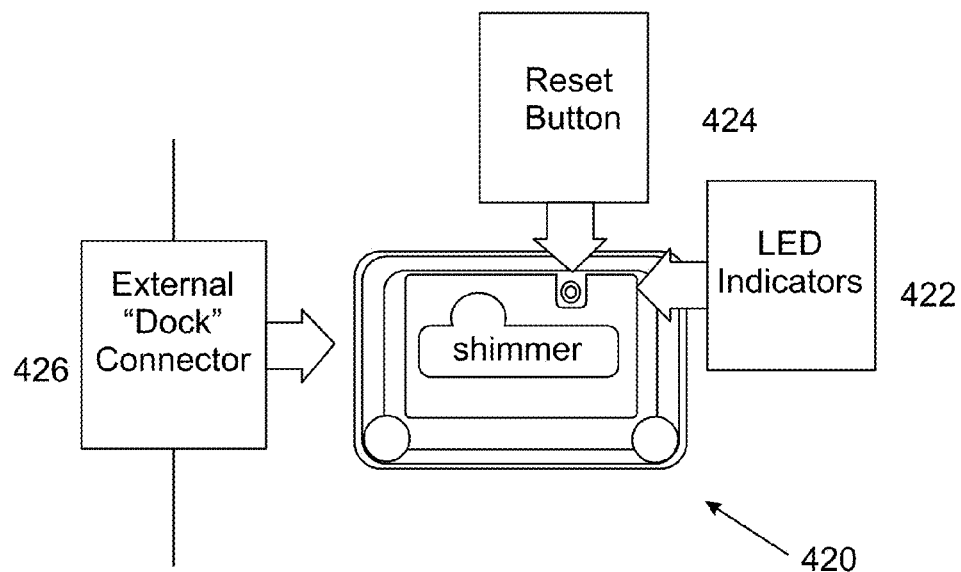
FIG. 4B illustrates a shimmer sensor used in accordance with some embodiments of the invention.

Optionally, accelerometer and/or gyroscope body-worn sensors as shown in FIG. 4B are attached to, for example, the ankles of the patient to help detect FOG episodes. Exemplary Shimmer sensors 420 are provided by www(dot)shimmer-research(dot)com. The sensors contain 3-axis accelerometers and 3-axis MEMs Gyro that record data at a sampling rate of 100 Hz via Class 2 Bluetooth Radio, and optionally serve to close the VR simulation loop. Optionally, sensors 420 include an external dock 426, a reset button 424 and/or indicators, such as LED indicators 422. In an exemplary embodiment of the invention, data from the Shimmer sensors is channeled to Matlab software, running on a laptop computer (e.g., 412), that performs real-time synchronization between the 2 shimmers (on both ankles) and runs an algorithm for detecting FOGs, based on, for example, the FOG Index (FI), described below. Optionally, the laptop running the FI algorithm is connected to a computer running the virtual reality simulation using a network cable and TCP protocol. When a FOG is detected, a signal is sent to the virtual reality simulation, enabling the simulation to record the precise location and time of the detected event within the simulation. The system also records the leg on which the event was detected first (the sensor that detected the FOG threshold), the speed at which the patient was walking, the type of trail i.e., the conditions of the VR simulation, the type of obstacles used, if any, and/or the type of FOG provocations provided by the simulation at the time of the event.

Figure 4C:
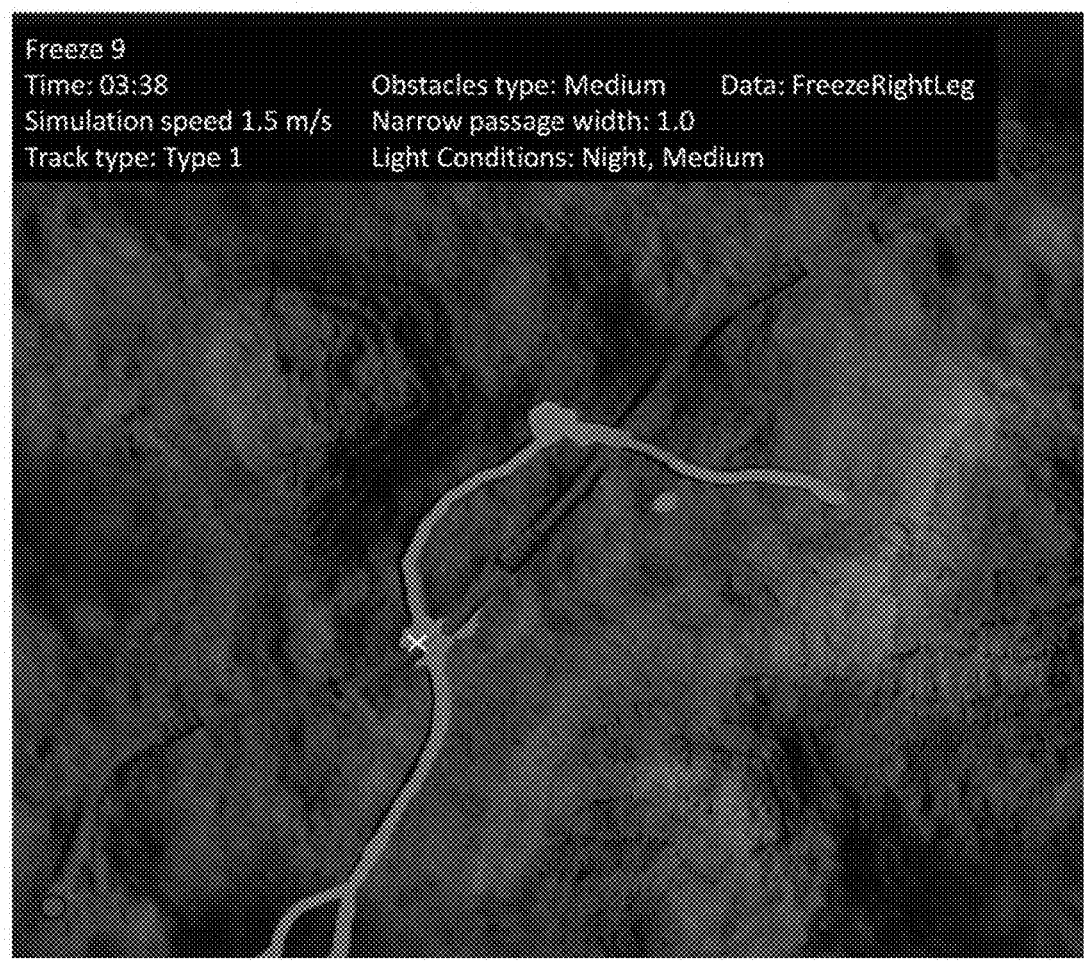
FIG. 4C is an aerial visual representation of the VR simulation trail and a recorded FOG event within the trail, in accordance with some embodiments of the invention.

FIG. 4C shows an aerial visual representation of a VR simulation trail and a recorded FOG event within the trail. The time of event within the session is recorded as well as the location on the path (represented by the white x, in this case on the narrow bridge over the virtual river), the type of trail used and the challenges provided (in this case, night condition and narrow pathways) and the first leg the event was detected by the shimmer sensors (in this case the right leg).

While this implementation may use a dedicated VR simulation, in other embodiments, the VR simulation is part of a commercial game. Optionally, the game is modified to generate a desired rate of challenges, for example, by creating narrowings in pathways. Alternatively, a game is selected with sufficient challenges and the patient simply plays the game, while the system tracks which challenges affected the patient and in what manner.

As noted above, for validation and/or other uses, additional sensors may be used, for example, miniaturized physiological sensors (NeXus MindMedia BV the Netherlands) may be attached to the patient's chest to monitor the patient's heart rate during different scenarios and walking conditions and physical and mental stress. Wireless Functional Near Infrared Spectroscropy sensors (fNIRS—PortaLite, Artinis, The Netherlands) may be placed on the patients forehead to assess blood oxygenation in the frontal lobe during the test. These signals may reflect frontal lobe activation in response to different stimulations and/or allow the assessment of cognitive function during FOG. Optionally, these two modalities are used for validation of the FOG events. Optionally or alternatively, they can be used as an option in the diagnostic system to provide additional information to the clinician. In an exemplary embodiment of the invention, all systems and sub-systems are synchronized and the sessions are videotaped to allow for further analyses of the FOG events.

The VR Simulation

Figure 4D:
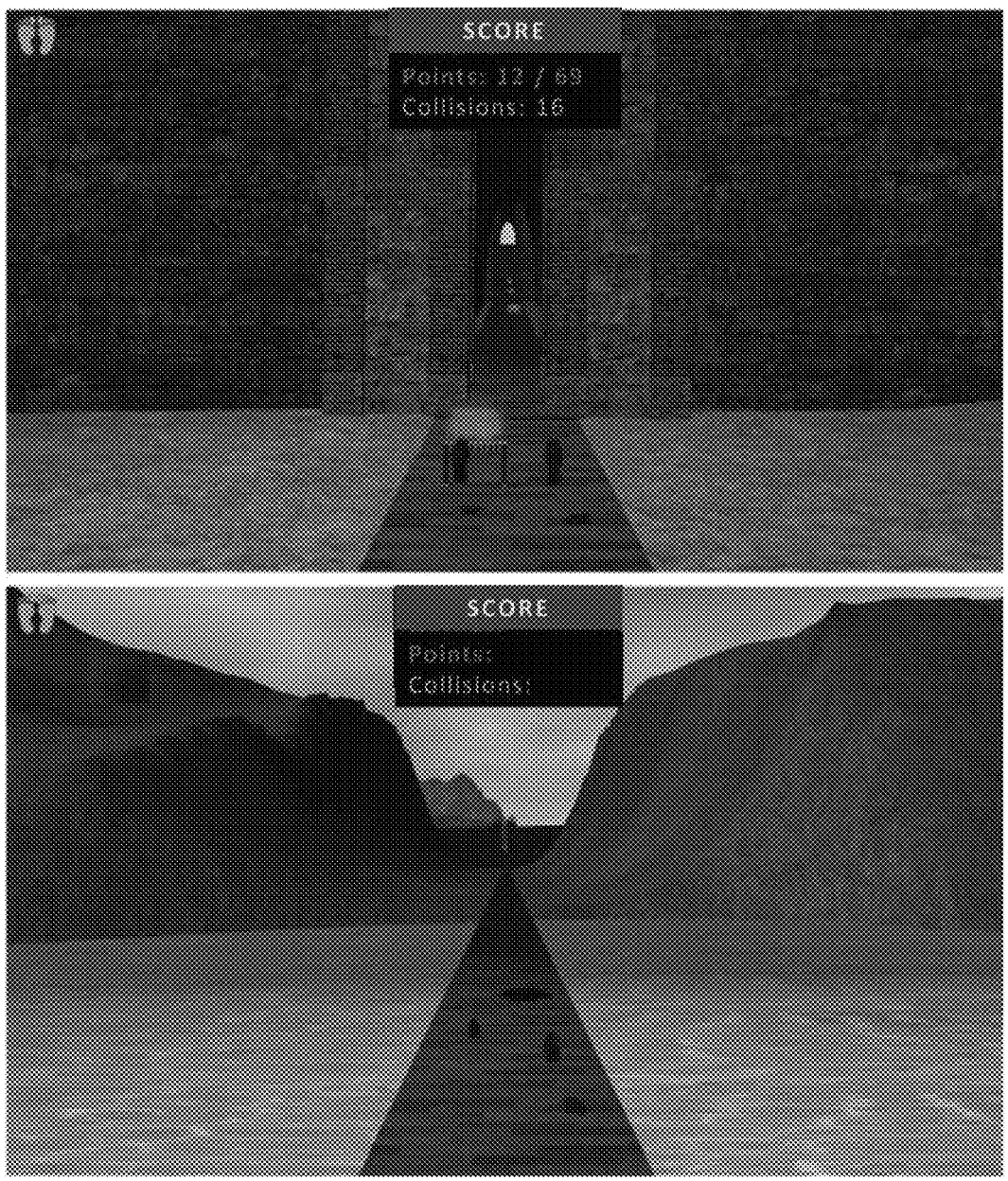
FIG. 4D shows two examples of virtual scenes designed to provoke FOG, in accordance with some embodiments of the invention.

In an exemplary embodiment of the invention, the VR simulation is designed specifically for this use and written in OGRE (Object-Oriented Graphics Rendering Engine) which is a scene-oriented, real-time, flexible 3D rendering engine, programmed in C# using Direct3D and OpenGL as the graphic libraries. The simulation optionally requires processing of multiple stimuli simultaneously. The VR scene consisted of an outdoor boardwalk on which different obstacles were placed. The patients were required to walk on the treadmill while negotiating the obstacles without hitting them. These mobility skills required decisions about step amplitude in two planes (vertical obstacles that required a high step and horizontal obstacles which required long steps) coordinated with walking behavior. See, for example, FIG. 4D which shows two examples of virtual scenes designed to provoke FOG. The patient's movement is represented by the shoes on the screen. These provide feedback as to movement, success or failure in negotiating the obstacles and a sense of presence within the VR simulation. A more complete avatar may be used as well. Obstacles presented were either vertical (top represented as a hurdle) requiring high clearance, or horizontal (bottom represented by a black muddy spot) requiring a long step. In order to successfully negotiate the obstacles, patients need to plan the correct response, plan the timing of passage and anticipate the speed required for performance. If successful they receive points on the score board shown on the top of the screen. If an error occurs and the patient touches the obstacle, a red light appears and the attempt is scored as collision. The amount of obstacles changes depending on the difficulty level of the trial and the speed at which they were walking at. The decision as to the side of appearance (right or left leg) is optionally chosen based on the more impaired side of PD symptoms (e.g., with 75% of the obstacles presented to the more affected side).

Figure 5:
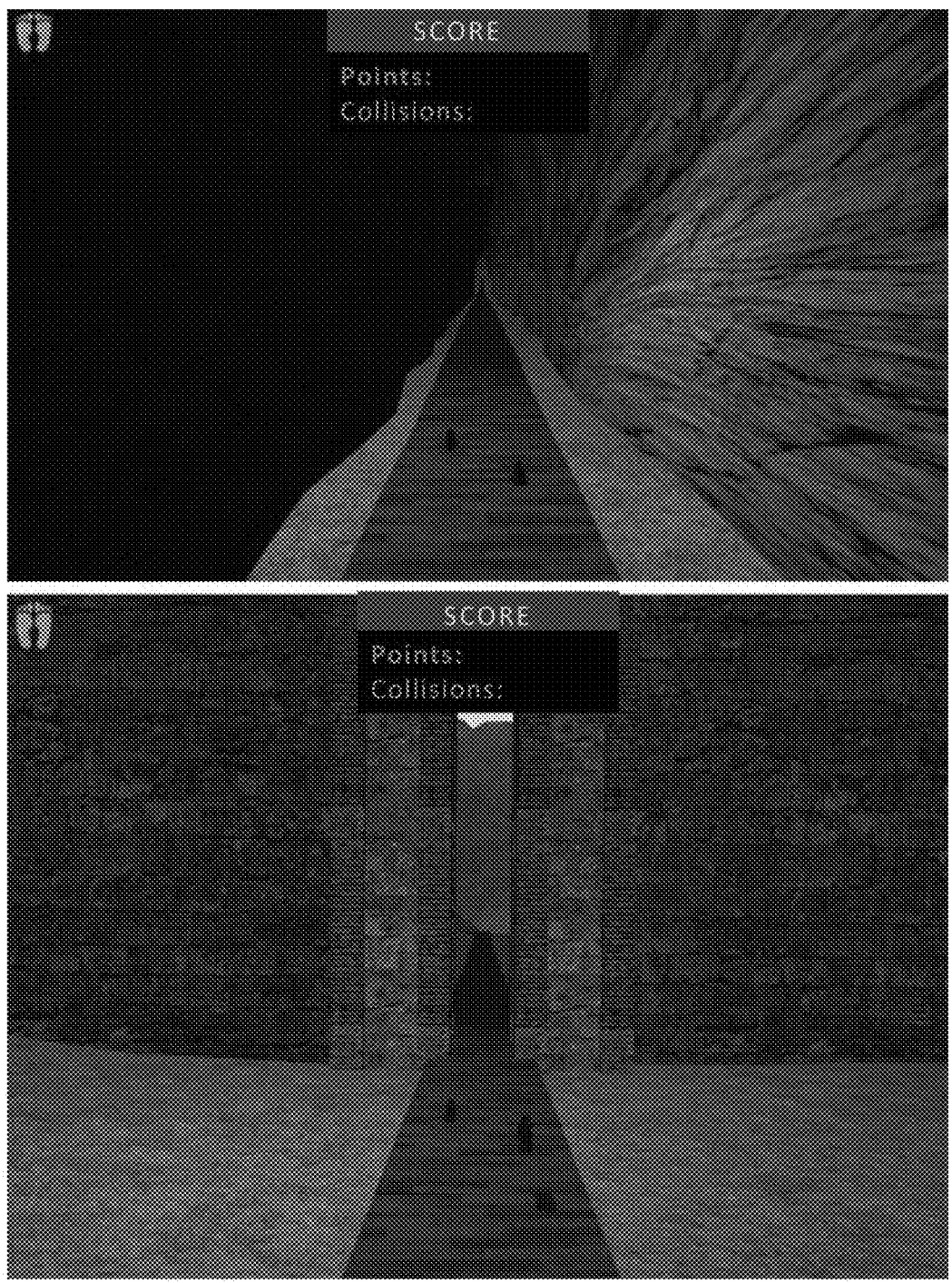
FIG. 5 is two examples of virtual freeze provoking scenarios, in accordance with an exemplary embodiment of the invention.

These decisions are optionally made more difficult using distracters such as changes in lighting and moving objects in the simulation and/or by adjustment of the frequency and/or size of the virtual obstacles. This allows varying the cognitive load independently of the gait complexity and/or potential FOG triggers. Optionally, the scene includes freeze provoking features such as bridges over rivers, narrow passages, tunnels, a cave, distracters and/or lighting effects. FIG. 5 shows two examples of virtual freeze provoking scenarios. These provocations included features such as bridges over rivers (see also FIG. 4D), tunnels or a cave (top), narrow passages (bottom) distracters and lighting effects (e.g., walking in diminished lighting conditions or in a bright sunny day). In an exemplary embodiment of the invention, such features are manipulated with respect to, for example, one or more of their frequency of appearance, size and/or location according to the individual patient's need and/or the difficulty level desired for a trial.

In an exemplary embodiment of the invention, the environment imposes a cognitive load requiring attention, planning and response selection as well as processing of rich visual stimuli involving several perceptual processes that have been associated with FOG. The VR provides visual and/or auditory feedback upon success or error of crossing the obstacles and/or if a FOG occurs; this feedback is optionally used as part of the therapeutic option. The system optionally provides information as to the location of the FOG, the timing of it, the leg on which it was first detected, and/or the duration of the event.

Data Processing and Extraction

As noted the system as described herein is optionally used for 1) assessing the possibility of detecting FOG using the system, 2) validating the FOG detection algorithms against physiological measures, and/or 3) quantifying the severity of FOG by combining different parameters of performance. Below is a description of exemplary methods used for data processing usable for these aims.

Gait Data

Gait data is optionally extracted from the accelerometers in the shimmer sensors. Average gait speed and stride time are optionally evaluated for walking trials. Data collected by the accelerometer are also optionally used to assess measures of rhythmicity and/or stability known to be impaired in patients with FOG. These included, for example, one or more of measures of variability, consistency and symmetry.

Spectral analysis of the calibrated acceleration signal in the locomotion band (0.5-3.0 Hz) is optionally used to assess measures of variability of the signals during gait on the treadmill without obstacles. The peak amplitude the width and the slope of the dominant frequency in the anterior-posterior direction are extracted from the raw signal; a sharper and narrower peak may reflect a more consistent, rhythmic, and healthier gait pattern, e.g., reduced gait variability and/or lower stride-to-stride fluctuations.

A symmetry ratio is optionally calculated based on the difference between acceleration of the right and left sensors during the no obstacle condition.

A Phase Coordination Index (PCI) is optionally calculated from the acceleration signal by determining the stride duration of one foot in the gait cycle (defined as) 360°, where the relative timing of the contra-lateral heel-strikes defined the phase which is represented by $\varphi$ (ideally, $\varphi=180$ for every step). The sum of the coefficient of variation and the mean absolute difference between $\varphi$ and 180° is defined as the PCI, representing variability and inaccuracy, respectively.

FOG Index

In an exemplary embodiment of the invention, a FOG Index (FI) is calculated from spectral considerations. In an exemplary embodiment of the invention, the FI reflects a ratio between the power in gait frequencies (e.g., 0.5-3.0 Hz) and the FOG frequencies (3-8 Hz). In an exemplary embodiment of the invention, calculation of these two measures is performed continuously and/or for each leg separately. In an exemplary embodiment of the invention, a real-time running window is applied to the data from the vertical axis (perpendicular axis to the ground). The size of the chosen window is optionally 1.2 seconds, as an example of a tradeoff between better frequency analysis and minimal latency, but smaller windows sizes (e.g., 0.6 seconds or less) may be used. The information from each window is transformed using, a spectral transform, such as Fast Fourier Transform (FFT) and the distribution of the signal, in the frequency domain, is calculated.

In an exemplary embodiment of the invention, a low FI is taken to reflect strong gait while a high FI suggests the present of a FOG. Optionally, the decision that a FOG occurred is done by comparing the FI, from each leg, to a pre-defined threshold. More formally, the calculation of the FI assesses each window, where N is the number of samples in each window and $X_k$ is the FFT of the data in the signal x within that window:

$$X_k = \Sigma_{i=1}^{N} x(i) e^{-2\pi i/N}$$

The spectrums in the Gait and FOG frequencies are optionally calculated from the FFT as follows:

$$\text{Spectrum}(k) = X_k * \text{conj}(X_k / N)$$

$$\text{Spectrum}_{Gait} = \sum_{k \in Gait\ frequencies} \text{Spectrum}(k)$$

$$\text{Spectrum}_{FoG} = \sum_{k \in FoG\ frequencies} \text{Spectrum}(k)$$

FI may then be calculated from the spectrum in gait and FOG:

$$FI = \frac{\text{Spectrum}_{Gait}}{\text{Spectrum}_{FoG}}$$

Optionally or alternatively, a calculation method may be used, as described in, for example, Moore S T, Macdougall H G, Ondo W G. "Ambulatory monitoring of freezing of gait in Parkinson's disease". J. Neurosci. Methods 2008; 167(2): 340-8; and/or J. M. Hausdorff, J. Balash, N. Giladi "Time series analysis of leg movements during freezing of gait in Parkinson's disease: akinesia, rhyme or reason?" Physica A: Stat Mechanics & Appl 2003; 321: 565-570.

In an exemplary embodiment of the invention, when a FOG is detected, a signal is sent to the virtual reality simulation. One or more of the precise location and time of the occurred event within the simulation, the leg on which the event was detected first, the speed at which the patient was walking in, the type of trail, obstacles and provocation provided by the simulation at the time of event are optionally recorded by the VR simulation. Data on FOG detection are optionally extracted from both the sensors and the VR simulation for further analysis.

In an exemplary embodiment of the invention, a FOG severity score is used, which is a composite measure based on the number of FOG events detected during the test, gait parameters reflecting abnormal patterns (e.g., stride time variability (CV), PCI, symmetry), the response to the VR provocations, number of errors on obstacle crossing, the cost of environmental features (determined as the stride time in trial 3-stride time in trial 4) and/or the cost of cognitive load on performance (stride time in trial 5-stride time in trial 4). Table 1 (FIG. 14) shows that a patient receives an overall, composite score, based on the combination of multiple components. In addition to this single summary measure, a clinician can receive more detailed information that describes FOG propensity based on performance in the VR system. In an exemplary embodiment of the invention, using a weighted analysis based upon all of the relevant components, a score is provided on a 4 point Likert scale. Optionally, the weighting is updated, for example, per patient clinical background and/or as more patients are diagnosed and treated.

Exemplary Detection and/or Prediction Using k-Means

In an exemplary embodiment of the invention, a machine learning method (e.g., k-means or other supervised or unsupervised or semi-supervised learning method) is used to identify and/or predict FOG events, of a single type and/or of several types.

In one example, using FOG annotations of data, extracted from a video by a physiologist, each window is given a label as "During FOG", "Pre FOG" and "Other". Optionally, a period of time prior to a beginning of FOG, labeled as "Pre FOG", is of 2 second, though other lengths may be used. "Other" labels are used, for example, while the patient was sitting, getting up from the chair, or otherwise not engaged in normal gait. In an exemplary embodiment of the invention, as a training set for the K-means algorithm only the signals labeled as "Other" and as "Pre FOG" are used and the remaining samples are considered as a test group. In one example, a learning set contained 15 FOGs out of 32 which were recorded during a training practice. Other, for example, greater, numbers may be used. K-means is used to automatically divide the inputted data into 80 clusters. Then, using the label, assigned to each signal section, the probability for each cluster to be predictive for a FOG is calculated. In one example, a subject was asked to walk in different conditions in the lab for 30 minutes and a total of 32 freezing episodes were identified in a post hoc video analysis. The data were halved and the first walking period that included 15 freezing episodes used for learning. The results indicate that some clusters tend to appear before FOG events and can give a prediction from 20% and up to almost 60%. It is also noted that the spectrum of the predictive clusters are somewhat similar to each other and different form non-predictive clusters. More specifically, time series of acclamation data were parsed to 1 s windows and FFT was run. All windows were sorted to 80 clusters based on frequency domain characteristics resemblance. In a post hoc analysis each cluster was assigned with its probability of being predictive for the occurrence of FOG episode within the "next 2 seconds". Most of the clusters have less of 10% predictive power, and that about 5-10 clusters have increasing predictive power. One cluster was found with a predictive power of almost 60%.

Figure 15A:
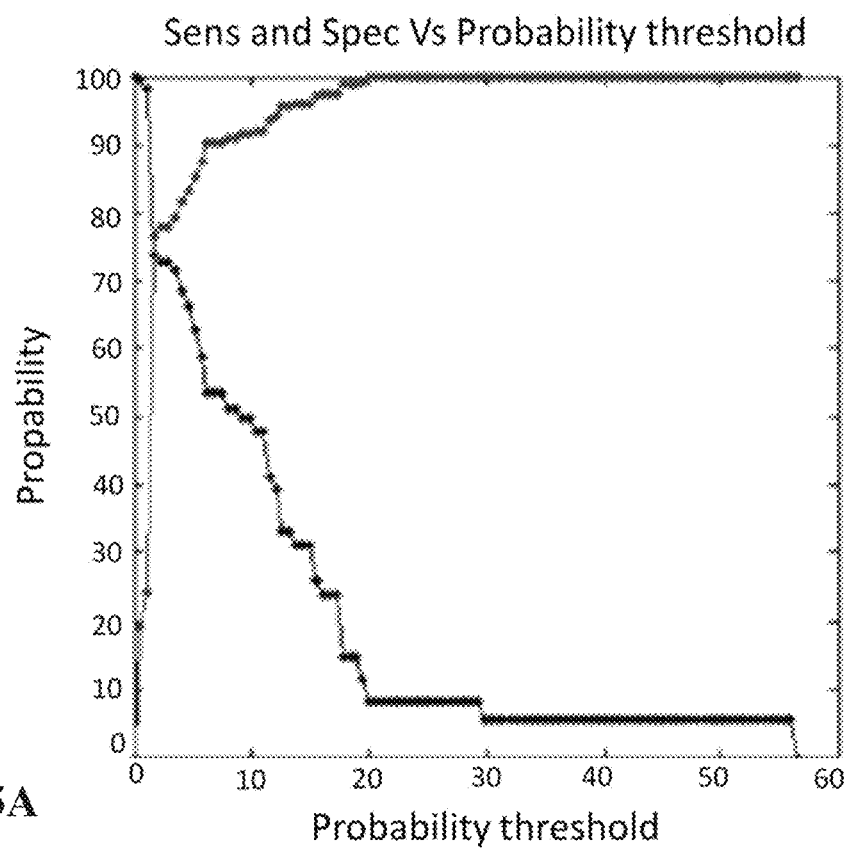
FIGS. 15A-15D are graphs showing results of a k-means FOG detection method, in accordance with an exemplary embodiment of the invention.
Figure 15B:
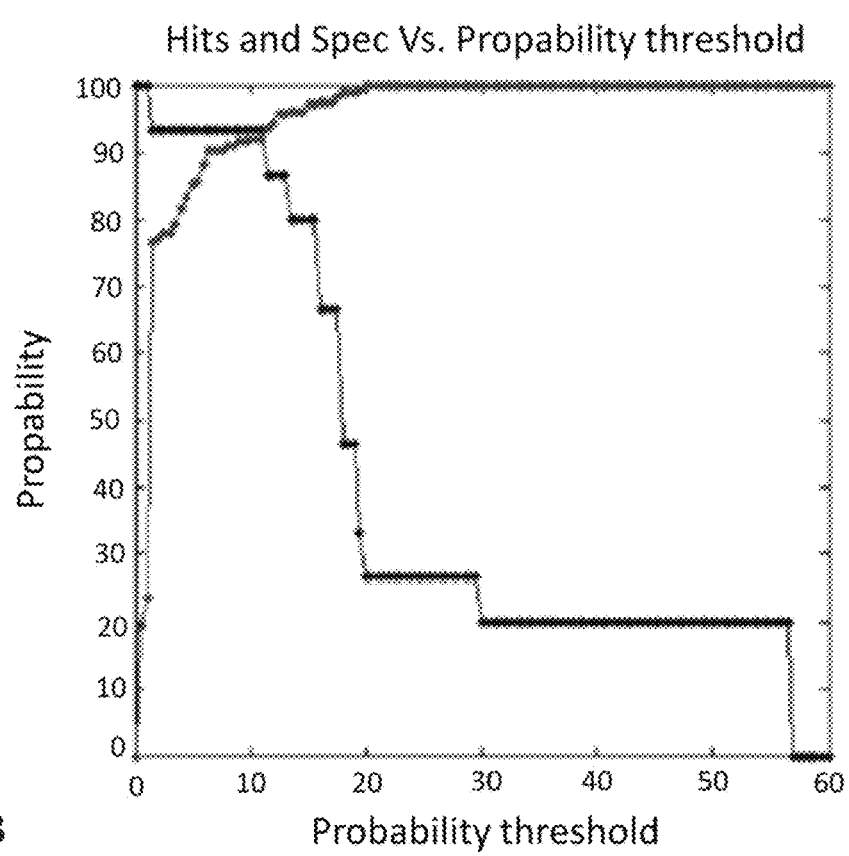
Figure 15C:
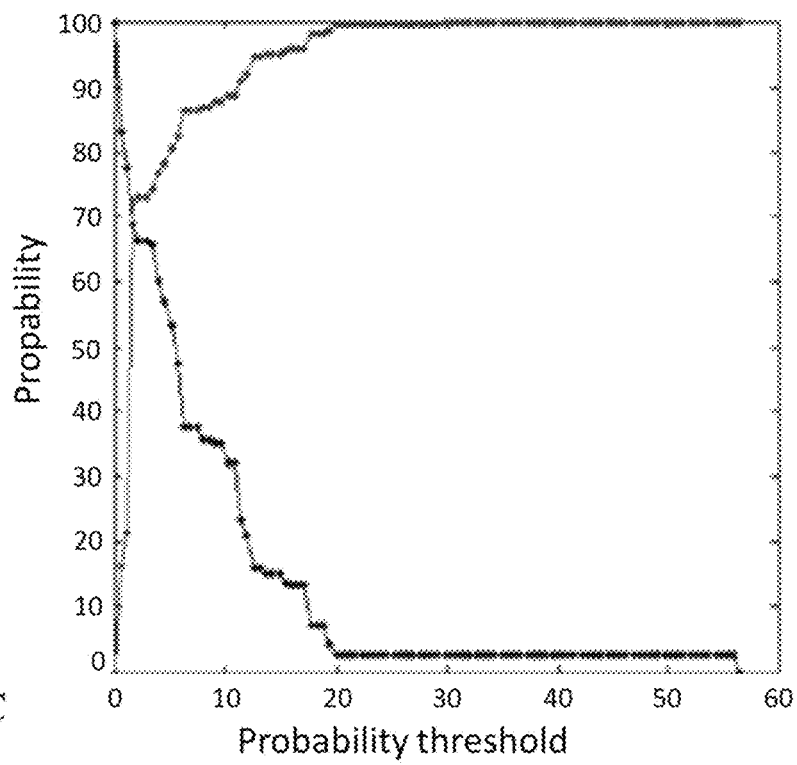
Figure 15D:
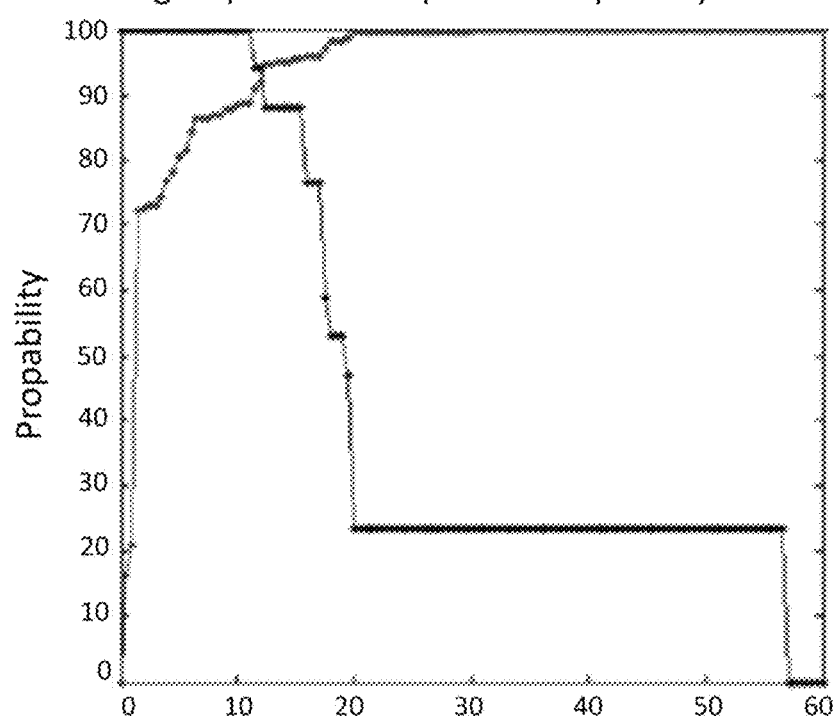

In an exemplary embodiment of the invention, a determination is made as to which of the clusters that were defined by the K-means algorithm should be chosen as predictors for FOG episodes. By applying a probability threshold and using only clusters with a probability higher than this threshold it is possible to calculate the sensitivity and specificity of such prediction. FIGS. 15A-15D describe this process. Technological sensitivity and specificity values (e.g., examining if the clusters will define every 0.5 s of the trace as predicting or not predicting FOG within the following 2 seconds), were calculated (panels 15A and 15C). In addition a prediction of a FOG is defined if at least one prediction was done at the pre FOG time (2 s). If a FOG was predicted then "Hit"=1 for it and otherwise "Hit=0". Specificity was calculated in a similar manner (panels 15B and 15D). It can be seen that for the training period (panels A and B) the chosen probability threshold for optimizing the benefits of high sensitivity (high percentage of "hits") and high specificity (low percentage of "false alarms") is between 10% and 20% probability (the intersection between the traces). Hits rate was 93.3% (14/15 FOGs, predicted correctly) and Specificity was around 92% (FIG. 15B). Using the same clusters that were defined for the learning data, and choosing the same probability threshold, on the testing data yields prediction of 100% (17/17 fogs are predicted) and Specificity of 88.7% (panels 15C and 15D). In all the panels, sensitivity (of the FOG prediction algorithm (ordinates)) is the decreasing line and specificity is the increasing line. These are plotted against the probability threshold (abscissas).

In an exemplary embodiment of the invention, this process is used to adapt the detection and/or prediction for specific subjects. In some embodiments, for each subject the system has to "learn" the specific algorithm characteristics that will be used. The results may then be programmed into, for example, the shimmer sensors. Optionally, by detecting pre-FOG events, a patient can be treated in time even if the FOG event determination time is longer than a few milliseconds, for example, being between 0.5 or 1 second and 2-3 seconds.

In an exemplary embodiment of the invention, a similar method is used to label FOG events, rather than pre-FOG events.

Experiment

The above-described implementation was used in an experimental study, as described below and show the ability of the proposed VR system, in accordance with some embodiments of the invention (e.g., FIGS. 4A-FIG. 5) to provoke and detect FOG episodes under safe environmental conditions. The system is able to provoke FOG episodes on the treadmill, which until recently was considered rare. The system is able to sensitively detect these FOG episodes, and using the system features is able to quantify and/or configure a severity score that can be used to diagnose and later provide care to patients experiencing FOG. It is noted that features described with the experiment may be used or not with other embodiments of the invention form the one used in the experiment.

Participants

The developed system was tested on 4 patients with PD (mean age 63.75±7.36 yrs) who suffer from FOG. Patients were included if they were diagnosed with PD (based on the UK brain bank criteria), reported experiencing FOG episodes (more than 5 on the new FOG questionnaire) and were able to walk unsupported for at least 10 minutes. Patients were excluded if they had substantial cognitive deficits (scored <21 on the Montreal Cognitive Assessment scale), unstable heart disease or suffered from severe depression. FOG can occur in other patient populations, e.g., patients with a higher-level gait disorder may also be diagnosed and/or treated using methods and/or systems as described herein.

Procedures

After signing an informed consent, demographic information and medical history were collected by a researcher. All testing for validation of diagnostic properties occurred in the "wearing off" state (approximately 3 hours after intake of medications). Prior to testing the system, a baseline assessment was conducted to evaluate gait over ground. Gait speed was measured over 10 meters. This information was imperative as the treadmill speed during the system's evaluation was set for each patient based on their over ground walking speed. In other embodiments, speed may be set during trial and/or matched to an actual walking speed on a continuous and/or semi-continuous basis. Patients were then fitted with the sensors (Shimmer, Nexus and fNIRS) for testing with the system. The test included 5 walking conditions each of 4 minutes for a total of 20 minutes of walking. This is comparable in time to a typical cardiac stress test. It could be shortened or lengthened, depending on the response of the patient to initial stress conditions. For example, a stress tests can include between 1 and 10 conditions, each applied for between 0.5 and 10 minutes. A total length, including breaks, can be, for example, between 5 and 60 minutes, for example, between 15 and 45 minutes. Rest breaks of 5 minutes were given between the trials, during which the patients were seated. The trials varied with each walking condition focusing on a different component that may influence FOG events:

Trial 1—Difficult: high level of difficulty, maximum amount of obstacles, maximum amount of freeze provoking challenges (tunnels, cave, bridges, and narrow passages)

Trial 2—Moderate: medium level of difficulty, moderate amount of obstacles, minimal amount of freeze provoking challenges, low environmental complexity Trial 3—Environment: high level of difficulty, moderate amount of obstacles, minimal freeze provoking challenges, high environmental complexity (obstructed visibility, night)

Trial 4—FOG challenges: low level of difficulty, no obstacles, maximum freeze provoking challenges (tunnels, caves, bridges and narrow passages)

Trial 5—Cognitive: high level of difficulty, moderate amount of obstacles, low amount of freeze provoking challenges, additional cognitive task (on top of walking with the VR simulation, the patients were asked to perform a verbal fluency task).

While other trials/levels may be selected, these represent the most common causes for FOG.

Validation of FOG Detection

In order to validate FOG detection, multiple methods were used.
  a. During the tests, an experienced clinician observed the patients and annotated any FOG episodes that occurred. The report included both descriptive measures of severity and time of event. In addition, all trials were videotaped. Another experienced researcher was asked to review the recorded videos and annotate time of FOG events based on the video recordings. These were then compared to the FOG events detected by the system and by the researcher who attended the tests.
  b. Miniaturized physiological sensors (NeXus MindMedia BV the Netherlands) were attached to the patient's chest to monitor the patient's heart rate (HR) during different scenarios and walking conditions and physical and mental stress to try and identify if any changes occurred that could indicate an event. As noted, optionally, these sensors can also be used to aid the clinician in the diagnosis and evaluation of the possible causes of FOG in a particular patient; for example, heart rate increases occur just prior to and/or during an episode; such an observation supports the idea that any detected event is indeed a FOG episode. The wireless NeXus sensors transmitted data in real-time to a computer using Bluetooth technology. Using designated software, heart rate and inter-bit-intervals were extracted from the data collected by the sensors in all gait trials.
  c. Wireless functional Near Infrared Spectroscopy (PortaLite, Artinis, The Netherlands) was used to assess changes in frontal lobe blood flow during gait and specifically during FOG events. The system uses Near Infrared Spectroscopy to measure local tissue saturation as well as oxy, deoxy and total hemoglobin concentrations in the frontal lobe during activity. Oxy and deoxy hemoglobin data (in units of micromol/liter) during all gait trials were extracted using Matlab software. As noted, optionally, these sensors can also be used to aid the clinician in the diagnosis and evaluation of the possible causes of FOG in a particular patient. It may, for example, indicate inadequate shifting of cognitive resources that lead to a FOG episode. Cognitive training, via the system or otherwise, may help to alleviate this problem.

Data from both HR and FNIRS were examined throughout the gait trials and changes and events were assessed and verified according to the video recordings. The signals were then examined for an interval of 10 seconds before and after a FOG event (as detected by the system) to observe any changes in activation. The signals were then compared to no-event and no-obstacle trials.

Data Analysis

Data was examined for normalcy and descriptive statistics were extracted for all gait measures. FOG detection data were compared across and within all subjects. Validation data were analyzed based on time series across all FOG events. Quantification data were analyzed for each patient as a case study.

Results

Diagnostic Capabilities

Four patients with PD participate in this study designed to demonstrate diagnostic capabilities. Disease severity of all 4 patients was 3 on the Hohen and Yahr scale with an average disease duration of 10.2±6.7 years. All patients reported experiencing FOG in the home and community environment and filled out the New FOG questionnaire (NFOG-Q). The NFOG-Q defines severe FOG condition as patients who score >15 on the questionnaire. Three of the patients participating in this study scored more than 15 on the NFOG-Q and were considered to have severe FOG. All patients were functionally active and living in the community. Table 2 (FIG. 15E) provides the patient's descriptive characteristics.

Gait Data

Figure 6:
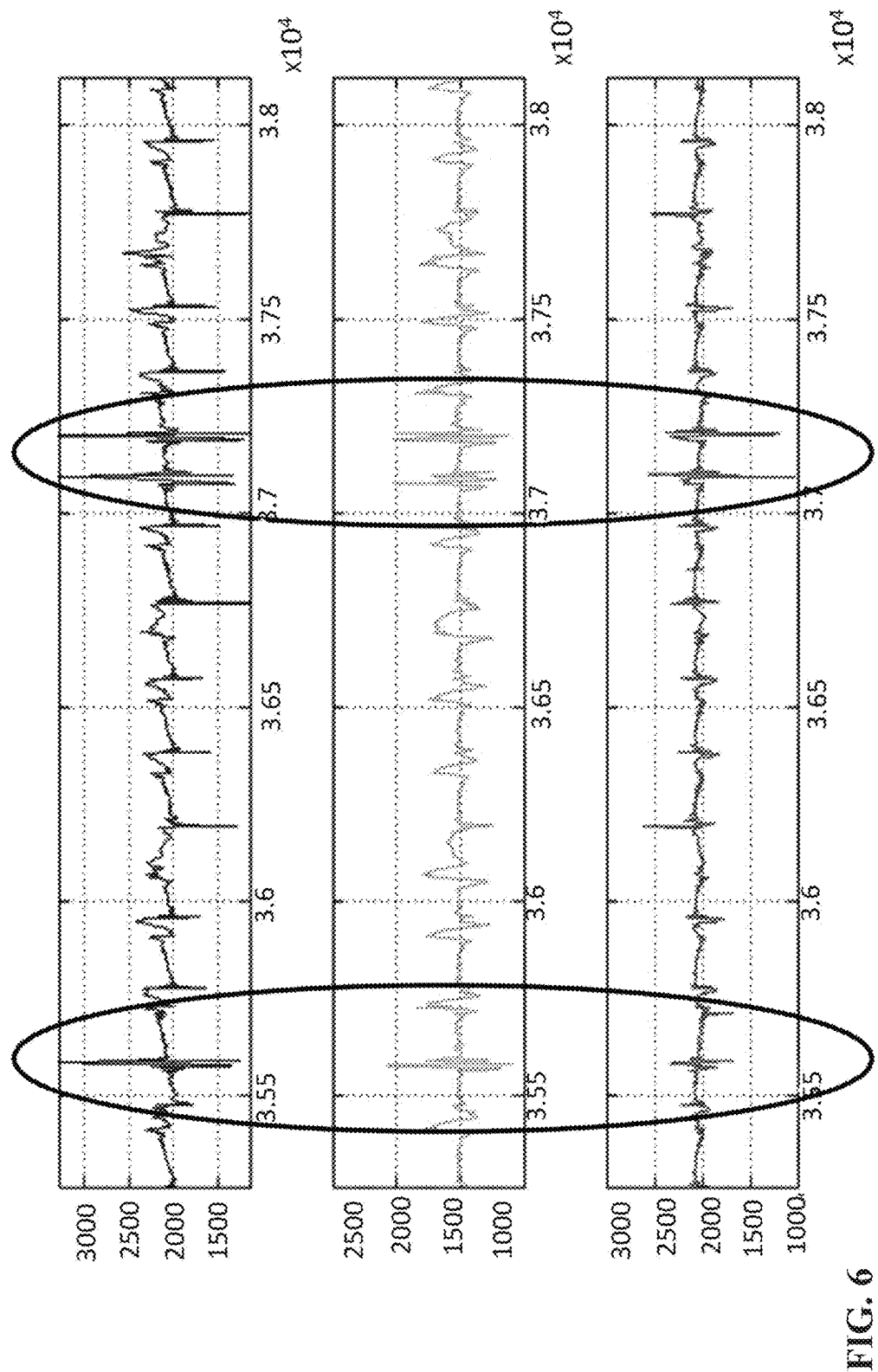
FIG. 6 shows the acceleration signal of the gait of patient 2 during the obstacle condition (trial 1), in an example according to an exemplary embodiment of the invention.

Mean gait speed during over-ground walking was 1.17±0.1 m/s. Gait speeds on the treadmill were set 20% slower to allow for obstacle negotiation as well as try to induce FOG events. Treadmill speeds ranged between 1-1.2 m/s and were not changed between the different trials, to maintain consistency of gait and evaluate strategies of walking in the different conditions. FIG. 6 demonstrates the acceleration signal of the walk of patient 2 in trial 1 (with obstacles). The top graph represents the signal collected in the anterior-posterior axis (AP), the middle signal represents the movement in the vertical axis (V) and the bottom signal represent movement in the medio-lateral direction (ML). The ellipses indicate the location of obstacles within this time frame. It may be noted that the acceleration increases when patient attempted to cross the obstacle. The Y axis is arbitrary (voltage units) and the X-axis is in samples (i.e., time).

Average stride time in the no-obstacle condition was 1.52±0.88 sec. During the obstacle conditions, stride time was shorter (1.15±0.66 sec and 1.35±0.74 sec). Shorter stride time was also apparent during the cognitive condition (1.42±0.68 sec) reflecting shorter steps in the more complex conditions.

The costs of adding obstacles, environmental features or a cognitive task were calculated as the difference in stride time from that observed in the no-obstacle conditions. Not surprisingly, patients demonstrated the highest difference in stride time in the obstacle condition (0.37 sec), as compared to no-obstacle condition. The cost of adding environmental or cognitive challenges were still considerable but not as robust (0.17 sec and 0.09 sec).

A symmetry ratio was calculated as the difference in stride time between the sensors worn on the right and left legs during the no obstacle condition and reflected as percent. This ratio reflects a difficulty in controlling gait evenly on both legs. Patients 1 and 2 showed almost perfect symmetry (99% and 98% respectively). Patient 4 had a low symmetry value of 64%, whereas patient 3 demonstrated the highest between leg inconsistency with a ratio of only 33%. This possibly reflects dis-coordination which could result in the increased risk of FOG.

Measures of consistency in walking were also evaluated. Coefficient of variation (CV) and PCI were calculated from the gait during the no-obstacle condition. For both measures, the closer the values were to zero, the more consistent the gait rhythm, suggesting a less impaired gait pattern with more intact bilateral coordination. In addition, the amplitude and width of the dominant frequency throughout the 4 minute no-obstacle walk were examined using spectral analysis. In table 3 (FIG. 16), are shown the results of the 4 subjects compared to a male control subject (67 years of age). A sharper and narrower peak reflects a more consistent, rhythmic, and healthier gait pattern, i.e., reduced gait variability and lower stride-to-stride fluctuations.

FIG. 7 shows the raw acceleration signal and spectral density of the frequency band of gait of a patient (patient 4) over 10 seconds during a no-obstacle trial. The width and the amplitude of the power spectral density (e.g., as measured by units of power per radians per second) are measures that reflect consistency; higher and narrower signals correspond to more consistent and less variable gait and vise versa. In the example in FIG. 7 the patient is walking on a treadmill that, on its own provides an external cue for consistency, and yet the signal produced by the accelerometer reflects high variability of gait, which could account to a higher risk for FOG's. Optionally, such variability in face of the external signal is used as a risk indicator even if no FOG (or other gait disorder) are detected. The effects of the various challenging conditions on these measures can also be included as another measure of FOG propensity. For example, similar to what was shown in FIG. 3, if the patient has difficulty negotiation obstacles and alters his/her gait pattern to bring it closer to the FOG zone, it will increase the patient's score and the likelihood that they have FOG, in general.

FOG Detection

A total of 77 FOG events were detected by the shimmer sensors; 45 of those were also identified by the therapist observing the gait as a FOG episode or abnormal stepping, shuffling or incorrect corrective attempt. These events reflected changes in frequency of the signal during walking within the window stipulated by the FFT. All events lasted less than 2 seconds except 7 which were longer (between 3-6 seconds). These longer events were all experienced by patient 4. Because of the use of the treadmill, the FOG events were relatively short as the treadmill belt continued to move and this contributed to the ability of the patients to eventually take a step forward and recover. Nonetheless, on the treadmill, good success was had at provoking FOG. Because of the movement of the treadmill, 3 of the longer events resulted in a complete cessation of walking and the researcher had to stop the treadmill as the patient was not able to take one step forward. This can be implemented as an automated feature activated in real-time, by a different embodiment of the invention.

Figure 8:
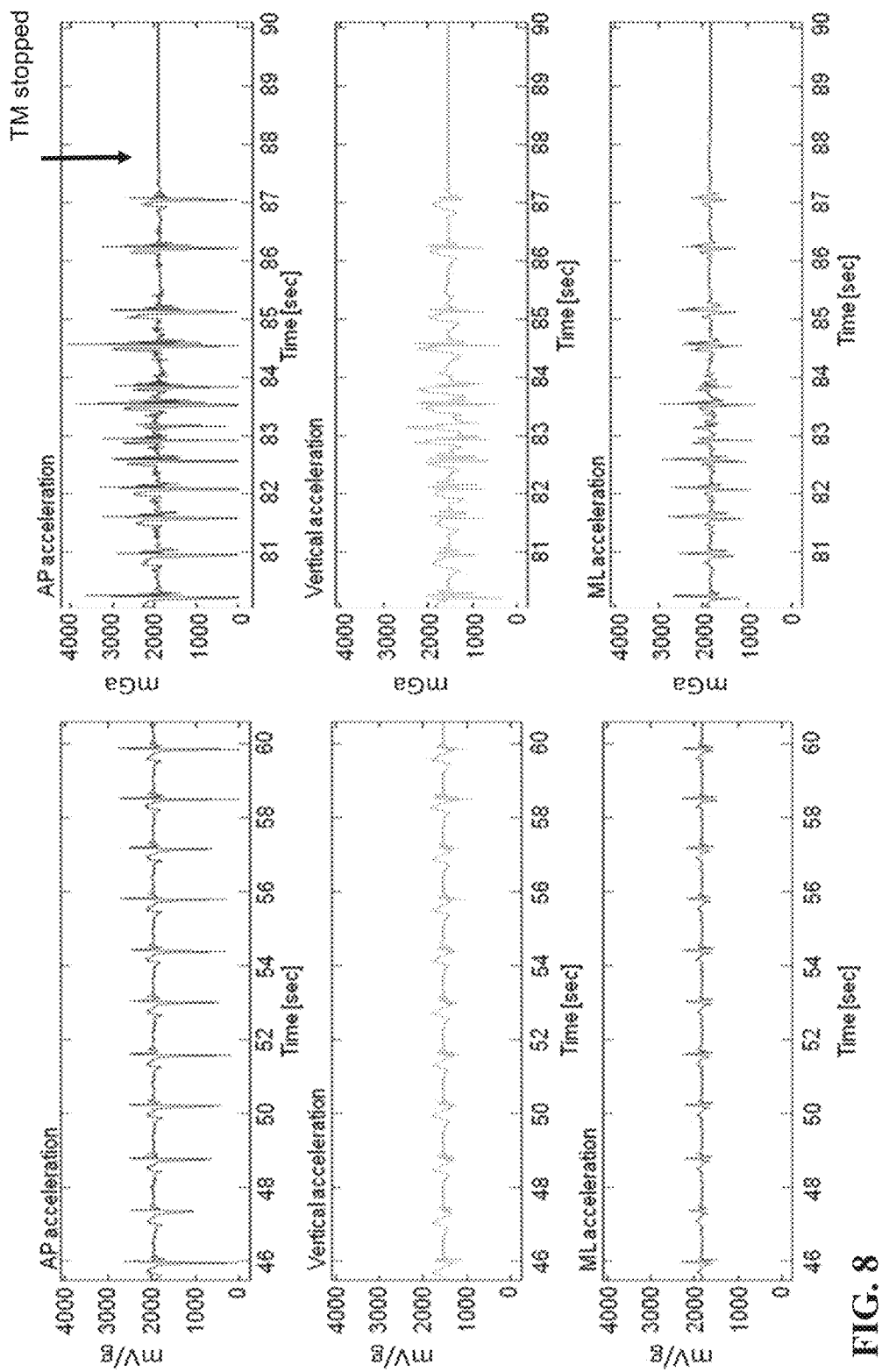
FIG. 8 shows a comparison between the acceleration signal of a regular gait and the signal during a FOG episode, in accordance with an exemplary embodiment of the invention.

FIG. 8 shows a comparison between the acceleration signal of a regular gait and the signal during a FOG episode. The acceleration signal on the left demonstrates relative consistency in strides as well as power of stepping. On the right is the gait of the same patient during a FOG event. The rapid jerkiness of the movement, the irregularity of the signal and the increased power are apparent. The FOG event lasted 5 seconds, after which the treadmill was stopped to prevent the patient from falling. Algorithms mentioned above (e.g., machine learning, K-means, wavelets and others) can be applied to automate this task, for example, by automatically detected FOG and then slowing or stopping the treadmill. Optionally, if it is determined that the treadmill was stopped at a non-FOG event, then the treadmill stoppage and its consequences are treated as a challenge and patient response thereto is optionally evaluated.

Validation

FOG detection by the sensors was compared against the recordings done by the researcher in the test and the identification of FOG events using video recordings. There were 77 events detected by the system, 45 of these were corroborated by the researcher observing the tests. From the videos, only 35 events were detected. Although this agreement is not high, it is important to note that since the events were very short, some of them were not observed by the researchers or easily observed on the video. In addition, there were no FOG events detected (or rated in the video) that were not detected by the system, hence the system shows high sensitivity but possibly moderate specificity. The system deemed some of the corrective patterns of walking (before obstacles) as FOG because they required a higher (faster pattern of walking). This indicates that perhaps the threshold window of detection should be increased and/or other detection parameters changed, optionally before and/or after obstacles and/or otherwise as a function of temporal and/or spatial relationship to an obstacle and/or other trigger. Optionally or alternatively, such corrective patterns are learned by the system and/or provided as preset patterns.

Figure 9:
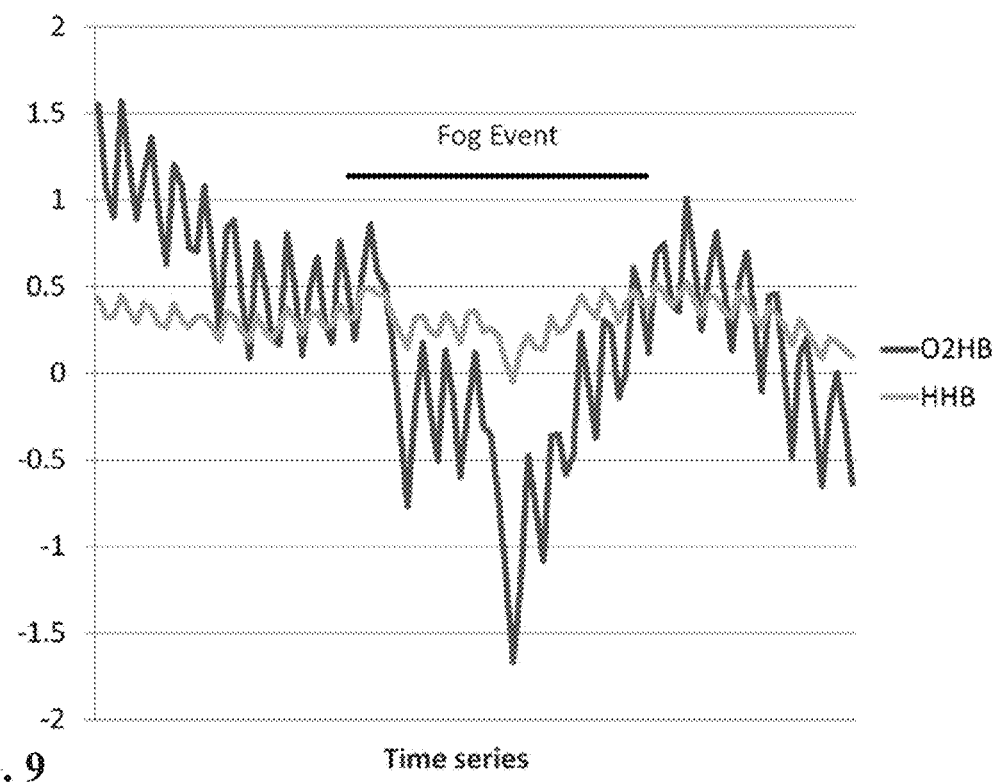
FIG. 9 shows the raw signal from the fNIRS (functional near-infrared spectroscopy), in accordance with an exemplary embodiment of the invention.

To further validate the system, physiological measures (fNIRS and HR) we used as well. FIG. 9 demonstrates the raw signal from the fNIRS during a FOG event. It is clear that there is a large change in the blood flow in the frontal lobe during the FOG event. This change was observed in all the long duration FOG events (more than 3 seconds). The light line represents de-oxy hemoglobin and the dark line represents oxy hemoglobin. The time series reflects 5 seconds prior to the event and 5 seconds after the event. The decrease in oxy hemoglobin in the frontal lobe during the event may suggest that the brain is circumventing blood flow to motor areas to compensate and in order to terminate the FOG episode.

Figure 10:
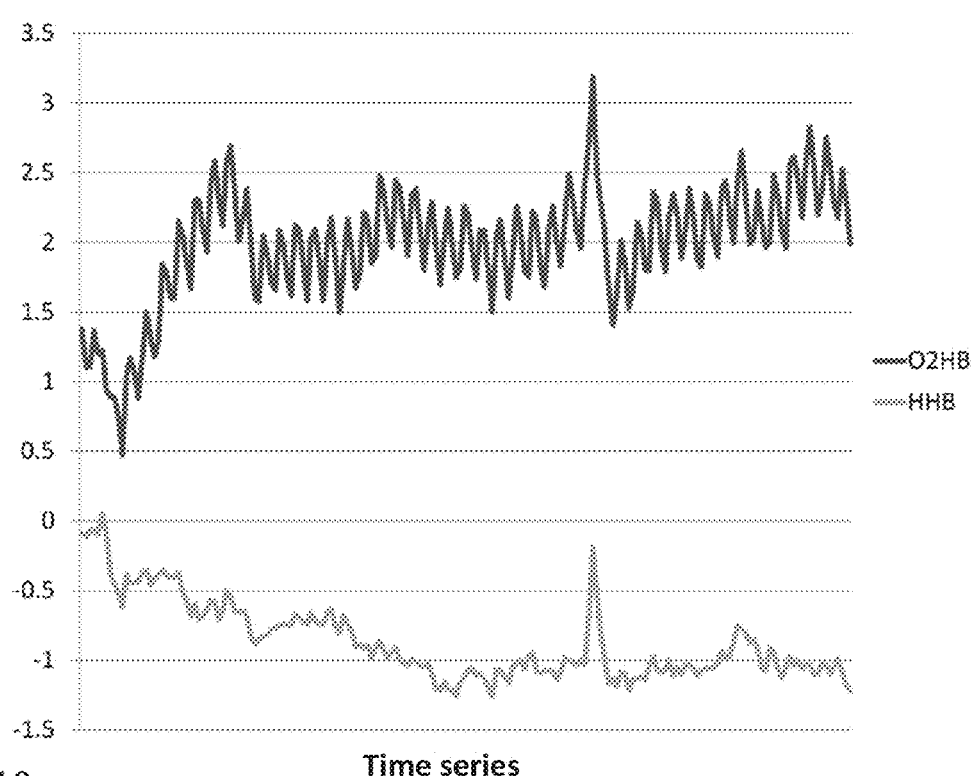
FIG. 10 shows the raw signal from the fNIRS during a trial (1) with obstacles with no FOG detected, in accordance with an exemplary embodiment of the invention.

This pattern was completely different when no FOG occurred. FIG. 10 shows an example of the fNIRS raw signal during the obstacle condition when no FOG occurred. The light line represents de-oxy hemoglobin and the dark lie represents oxy hemoglobin. The time series is 15 seconds long. As compared to the blood flow in FIG. 9, during the obstacle negotiation task the oxy hemoglobin did not increase during the trial, and demonstrated a stable consistent signal.

Figure 11:
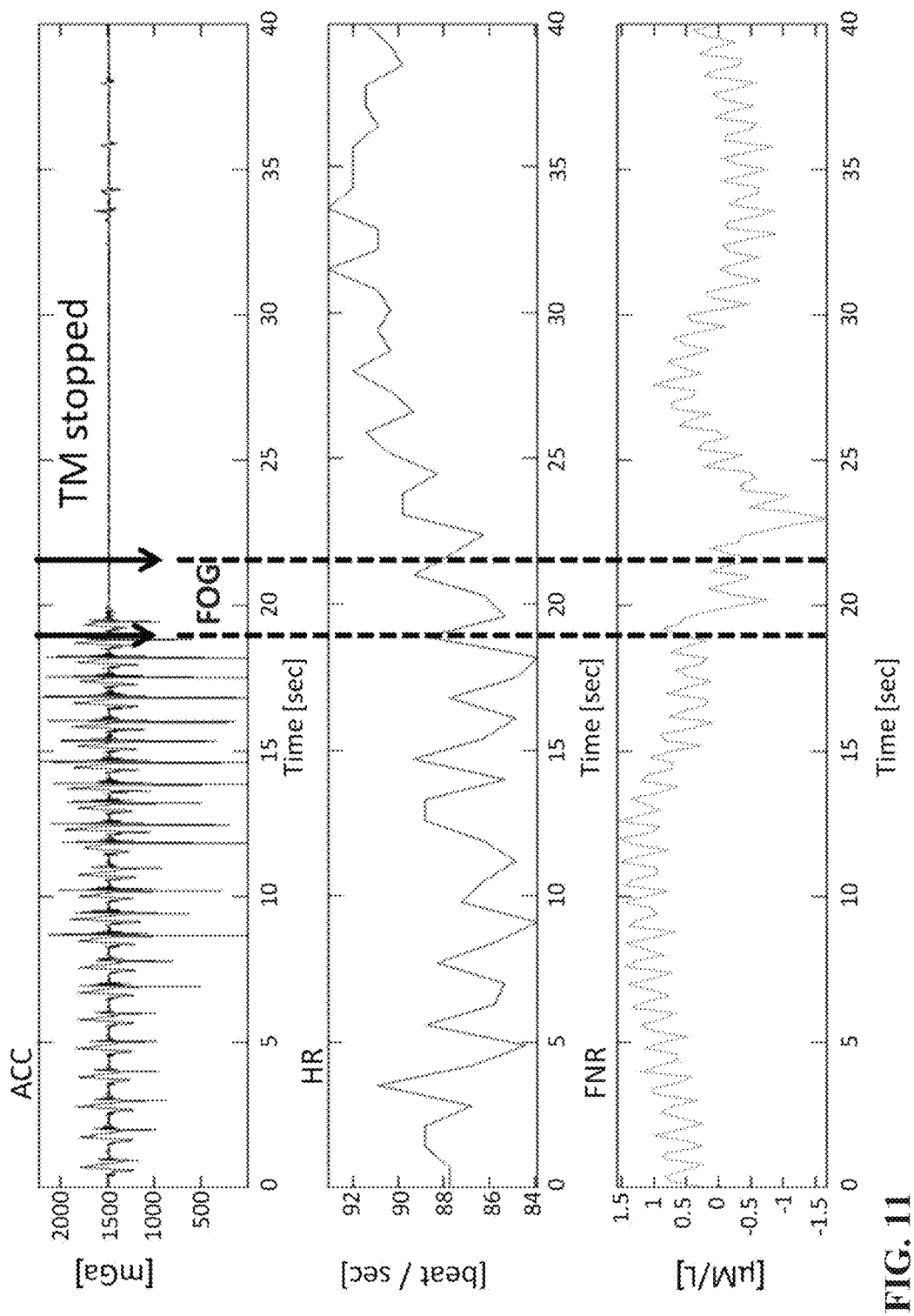
FIG. 11 shows signals from three physiological sensors, in accordance with an exemplary embodiment of the invention.

A relationship between changes in acceleration signal and changes in physiological measures is also investigated. FIG. 11 combines all 3 measures and provides for the first time an indication that changes in gait during FOG can be reflected in physiological measures even when the event is short in duration and the gait is performed on a treadmill. The top signal is the acceleration. The first vertical dashed line reflects the time the system detected the FOG. The middle signal reflects the heart rate extracted from the NeXus and the bottom signal shows the oxy-hemoglobin signal from the fNIRS. Note the changes in all 3 signals during and/or after the FOG event. The treadmill was stopped (second vertical line) after 4.2 seconds to allow the patient to recover from this event. After the cessation of walking, the signals start to recover.

Quantification

In an exemplary embodiment of the invention, a FOG severity score is a composite measure based on the number of FOG events detected during the test, gait parameters reflecting abnormal patterns (e.g., CV, PCI, symmetry) associated with FOG, the response to the VR provocations, number of errors on obstacle crossing, the cost of environmental features (e.g., determined as the average stride time in trial 3–average stride time in trial 4) and the cost of cognitive load on performance (e.g., average stride time in trial 5–average stride time in trial 4) (see table 2, FIG. 15). Using a weighted analysis, a score was provided on a 4 point Likert scale. The FOG score as determined using the system for each patient, is as follows.

Patient 1—

ED is a 64 year old male with PD with disease duration of 5 years. ED reported suffering from FOG episodes that occur almost exclusively during turns. A total of 28 FOG episodes were detected by the system during walking on the treadmill in all of trials, however, only 14 events were validated by the researchers as either FOG episodes or shuffling and abnormal gait patterns. It is believed that some of this discrepancy may be due to the high sensitivity of the system compared to the clinicians view. The system as describe herein, in accordance with some embodiments of the invention is able to detect even patterns of 'pre-FOG', short minimal episodes that do not turn into full FOG episodes. The freezing episodes mainly occurred during the difficult trial and while environmental challenges were added. ED walks with a very low clearance gait and often his gait appears as shuffling. 67% of the errors made on obstacle crossing were secondary to low clearance which increases the risk for FOG and falls. Table 4 (FIG. 17) summarizes the results of his tests.

Patient 2—

SC is a 73 year old man who was diagnosed with PD 15 years ago. He complains of occasional freezing mostly during turns and when going into tight occluded places. A total of 20 FOG episodes were detected by the system with 6 verified by video and an expert. 5 of the 6 events were caused by provocation within the VR scene of narrow passages and a tunnel. SC has relatively low gait variability but high bilateral dis-coordination (i.e., high PCI values). Table 5 (FIG. 18) shows the test parameters that contributed to the patients FOG severity score.

For this and other patients, the score, combined with the detailed explanation about the circumstances that provoke FOG are optionally used to understand and/or treat the problem, e.g., tailoring the prognosis and therapy. For example, evaluation of the aerial maps will show precisely what environmental properties triggered freezing in this patient, in combination, with which other provocations and VR features. Since this data can be reviewed simultaneously with the movement sensor data and gait properties, this may enable more precise identification of the particular circumstances (e.g., internal and/or external) that trigger freezing.

Patient 3—

MB is a 55 year old male who was diagnosed with PD 17 years ago. MB reports freezing on occasion that appear mostly when he is tired or during turns. Eleven FOG events were detected by the system, 7 of them were also detected by the researchers. Five of these 7 events occurred after provocations were added. MB's gait is fairly irregular with high asymmetry between the more affected (right) and less affected sides and high CV and PCI. This may also make FOG detection more difficult and/or less reliable, due to increase in background noise. Additional features such as environmental changes and a secondary cognitive task further deteriorate his gait and increase the risk for FOG's and consequently falls.

In an exemplary embodiment of the invention, in such patients with variable gait, training includes two components. A first component to reduce gait variability (e.g., desirably reducing risk for FOG in general) and a second component on dealing with specific FOG events.

In an exemplary embodiment of the invention, the methods and/or systems described herein are configured to be sensitive enough to detect FOG or future FOG risk even if no FOG symptoms are seen.

In some embodiments of the invention, the FOG detection mechanism is adapted to the patient. For example, a short monitoring period may be carried out during which the algorithm learns the patient's normal (e.g., variable or not) gait as well as freezing episodes. Then, for example, in a semi-automatic fashion, a user can tag suspected FOG events and these can be used to subsequently teach the algorithm.

Patient 4—

DT is a 63 year old male who has been diagnosed only 4 years ago. DT reports suffering from FOG especially during the evening when he is tired. He does not see a specific pattern to the events of FOG. During the test the system detected 17 events and the researchers detected 16. The FOG events for the most part were long considering he was walking on a treadmill. FOG events were observed as mostly the result of planning and negotiating the obstacles and during the cognitive condition. DT demonstrated more difficulty in negotiating the hurdles (vertical) obstacles then the puddles (horizontal). The frequency of the FOG events was high (2 in 30 seconds on the cognitive trial). DT's gait is highly variable and asymmetrical which further increases the risk for FOG. The longer FOG episodes gave the opportunity not only to detect the FOG but also to observe what would enable to recover from the FOG.

Results on Therapeutic Application

Further experimentation tested the idea of treatment based on diagnosis and/or controlled level of challenges. Without being limited to a specific hypothesis, it is possible that that motor learning principles and/or bio-feedback can modify the locomotion strategies employed by subjects with PD who are otherwise prone to FOG so that they will now be able to avert/reduce/recover from and/or otherwise assist approaching and/or ongoing FOG episodes. Possibly, the central nervous system (CNS) will be trained to modify the gait pattern in situations that typically cause FOG and/or generally increase risk of FOG (e.g., variability and/or lack of symmetry).

The paradigm used to assess this hypothesis applies rhythmic auditory stimulation (RAS) in an open-loop, feed-forward manner whenever a subject makes a turn, one of the most common FOG-provoking tasks. It is hypothesized: i) that external cueing can alter the gait pattern in such a way that the patho-physiological processes that typically lead to FOG will be averted. ii) Following repeated training with RAS, patients will learn to turn in a manner that does not provoke FOG, even in the absence of external cueing. Similarly, RAS can be administered just prior to other FOG provoking conditions. For example, if there is a change in rhythmicity and/or BCG when the patient approaches narrow passageways, RAS can be administered just before this to teach the patient how to more appropriately cross through these FOG provoking environments.

Given these hypotheses, the effects on FOG (frequency and duration) after a 6 week long intervention in which cueing was applied in a feed-forward, open-loop manner to enhance CNS pacing during turns and implicitly teach the patient's motor control system to minimize the propensity to FOG, were evaluated. In this pilot study, 11 patients with PD were assessed.

Figure 12:
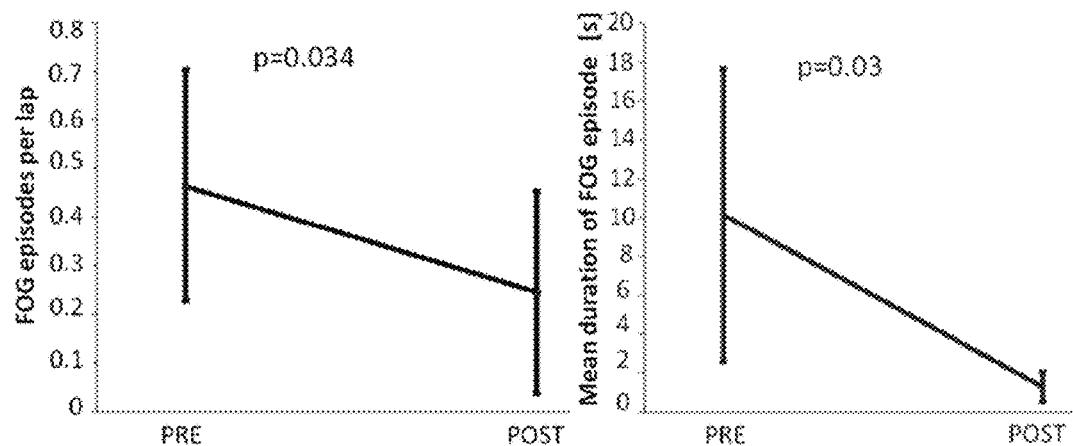
FIG. 12 shows an effect of intervention on FOG burden during figure 8 shaped paths, in accordance with an exemplary embodiment of the invention.

FIG. 12 depicts changes in group average of the number of FOG episodes (produced during figure 8 shaped trials (carried out on the ground, not a treadmill) which was the primary outcome measure) in response to the intervention. Within subject, the number of laps in the 'post' testing was identical to the number of laps that had been performed in the 'pre' testing. Chart A shows the number of FOG episodes during the figure 8 shaped paths. Mean values (±SE) for number of FOG episodes pre lap, which were 0.5±0.2 and 0.2±0.2 episodes/lap for the pre and post testing respectively. Chart B shows the mean (±SE) duration of FOG episodes, which were 10.1±7.5 s and 1.3±0.8 s for the pre and post testing respectively.

Figure 13:
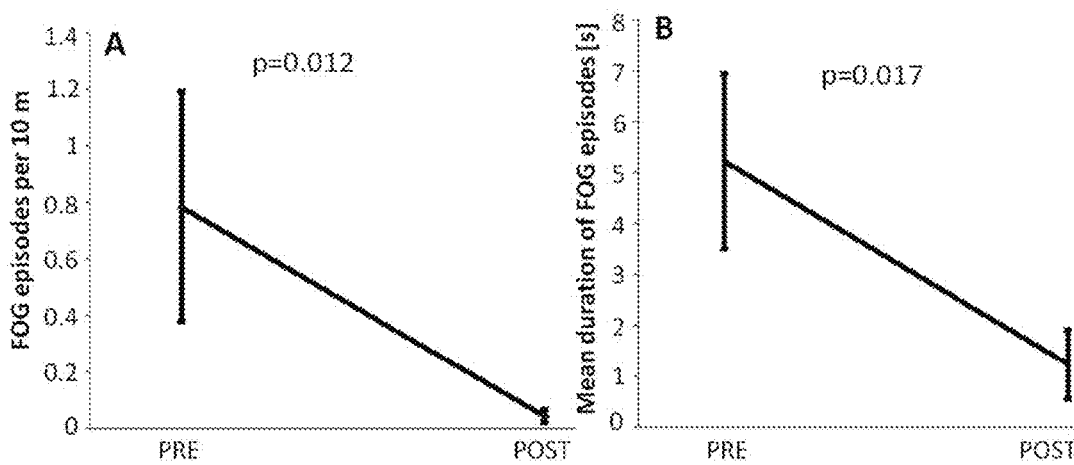
FIG. 13 shows the effect of intervention on FOG burden during straight line corridor walking, in accordance with an exemplary embodiment of the invention.

A somewhat stronger effect is shown during corridor walking which primarily consists of straight line walking (with a 180° turn at the edge of the corridor). FIG. 13 depicts this effect. Chart A shows the number of FOG episodes. Mean values (±SE) for number of FOG episodes pre 10 m were 0.78±0.40 and 0.05±0.02 for the pre and post testing, respectively. Chart B shows The mean (±SE) duration of FOG episodes which were 5.2±1.7 s and 1.2±0.7 s for the pre and post testing, respectively.

These results also indicate that training on a treadmill can transfer to a non-treadmill situation.

General

It is expected that during the life of a patent maturing from this application many relevant display technologies will be developed and the scope of the term virtual reality is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method to train a subject diagnosed with freezing of gait (FOG), comprising:
   assessing FOG in a subject by presenting freezing provoking stimuli to said subject on a display of a training system, and wherein said display is fixed relative to a surface on which said subject walks;
   identifying one or more freezing provoking stimuli from said presented stimuli, that increase a likelihood of FOG in said subject;
   generating a training program by a controller of said training system comprising one or more tasks stored in a memory of said training system based on results of said assessing, wherein each of said tasks comprises one or both of cognitive or motor tasks;
   and
   training said subject to change said subject response to said freezing provoking stimuli using said one or more tasks.

2. The method according to claim 1, comprising measuring a status of said subject following said training and adjusting at least one parameter of said one or more tasks of said training program based on said status.

3. The method according to claim 1, wherein said assessing comprises assessing said FOG by performing a FOG stress test by said subject and wherein said identifying comprises evaluating a response of said subject to said FOG stress test.

4. The method according to claim 3, wherein said FOG stress test comprises presentation of scenarios designed to stress a cognitive ability and/or a perceptual ability of said subject related to FOG events in said subject.

5. The method according to claim 1, wherein said assessing comprises identifying FOG subtypes.

6. The method according to claim 5, wherein said FOG subtypes comprise start hesitation and/or turning hesitation.

7. The method according to claim 5, wherein said FOG subtypes comprise narrow passage freezing and/or open runway freezing.

8. The method according to claim 5, wherein said FOG subtypes comprise reaching destination freezing.

9. The method according to claim 1, wherein said training comprises presenting virtual scenarios to said subject using a VR system or on said display.

10. The method according to claim 9, wherein said training comprises presenting virtual obstacles to said subject using said VR system or on said display.

11. The method according to claim 10, wherein said display is a fixed display located at a distance from said subject position, and wherein said virtual scenarios and/or said virtual obstacles are presented on said fixed display.

12. The method according to claim 11, wherein said virtual scenarios and/or said virtual obstacles are presented to a virtual representation of said subject on said fixed display.

13. The method according to claim 11, wherein said one or more tasks of said training program comprise dual tasking.

14. The method according to claim 1, wherein said one or more tasks of said training program comprise walking while dual tasking.

15. The method according to claim 2, wherein said one or more tasks of said training program comprise reaction to one or more virtual obstacles presented to said subject.

16. The method according to claim 15, wherein said adjusting comprises adjusting the number of said one or more virtual obstacles presented to said subject and/or the appearance frequency of said obstacles.

17. The method according to claim 2, wherein said training program comprises presenting a virtual walking path to said subject.

18. The method according to claim 17, wherein said adjusting comprises adjusting a width of said virtual walking path based on said status of said subject following said training.

19. The method according to claim 18, wherein said virtual walking path comprises one or more turns, and wherein adjusting comprises adjusting the number of said one or more turns in said virtual walking path based on said status of said subject following said training.

20. The method according to claim 17, wherein said virtual walking path comprises one or more bifurcations, and wherein said adjusting comprises changing the number of said one or more bifurcations in said walking path based on said status of said subject following said training.

21. The method according to claim 15, wherein said adjusting comprises adjusting the size of said one or more virtual obstacles.

22. The method according to claim 1, wherein said assessing FOG in a subject is performed at least partially manually by an expert.

23. The method according to claim 1, wherein said assessing FOG in a subject is performed at least partially automatically by an assessing system.

* * * * *